(12) United States Patent
Elliott et al.

(10) Patent No.: US 7,169,924 B2
(45) Date of Patent: Jan. 30, 2007

(54) PYRIMIDINONE DERIVATIVES AND THEIR USE IN THE TREATMENT OF ATHEROSCLEROSIS

(75) Inventors: Richard Leonard Elliott, Harlow (GB); Deirdre Mary Bernadette Hickey, Stevenage (GB); Robert John Ife, Stevenage (GB); Colin Andrew Leach, King of Prussia, PA (US); Ivan Leo Pinto, Stevenage (GB); Stephen Allan Smith, Stevenage (GB)

(73) Assignee: SmithKline Beecham plc, Brentford (GB)

( * ) Notice: Subject to any disclaimer, the term of this patent is extended or adjusted under 35 U.S.C. 154(b) by 343 days.

(21) Appl. No.: 10/398,977

(22) PCT Filed: Oct. 5, 2001

(86) PCT No.: PCT/EP01/11562

§ 371 (c)(1),
(2), (4) Date: Sep. 2, 2003

(87) PCT Pub. No.: WO02/30911

PCT Pub. Date: Apr. 18, 2002

(65) Prior Publication Data
US 2004/0058941 A1    Mar. 25, 2004

(30) Foreign Application Priority Data
Oct. 10, 2000    (GB)    ................... 0024807.0

(51) Int. Cl.
C07D 239/70    (2006.01)
A61K 31/517    (2006.01)
A61P 9/01    (2006.01)

(52) U.S. Cl. .................. 544/253; 514/258.1
(58) Field of Classification Search ............. 514/260.1, 514/262.1, 264.1, 266.3, 269, 258.1; 544/262, 544/278, 279, 287, 319, 253
See application file for complete search history.

(56) References Cited

U.S. PATENT DOCUMENTS 6,649,619 B1 * 11/2003 Hickey et al. ............ 514/258.1
2004/0097525 A1    5/2004 Hickey et al. ............ 514/260.1

FOREIGN PATENT DOCUMENTS

WO    WO 99/24420    5/1999
WO    WO 01/60805    8/2001

OTHER PUBLICATIONS

Michael Lam, "Magic Molecules", Pharmaceutical Executive, [online] Dec. 1, 2004, [retrieved on Jun. 9, 2005]. Retrieved from the internet, <http://www.pharmexec.com/pharmexec/article/articleDetail.jsp?id=140635&pageID=6>.*

Keith E Suckling et al, Expert Opinion on Therapeutic Targets, Jun. 2002, vol. 6, No. 3, pp. 309-314.*
James D Clark, Steve Tam, Expert Opinion on Therapeutic Patents, Jul. 2004, vol. 14, No. 7, pp. 937-950.*
Wolff, Manfred E. "Burger's Medicinal Chemistry, 4ed, Part III", John Wiley & Sons, 1981, pp. 514-515.*

* cited by examiner

Primary Examiner—Thomas C. McKenzie
(74) Attorney, Agent, or Firm—James M. Kanagy; Stephen Venetianer; Charles M. Kinzig

(57) ABSTRACT

Compound of formula (I):

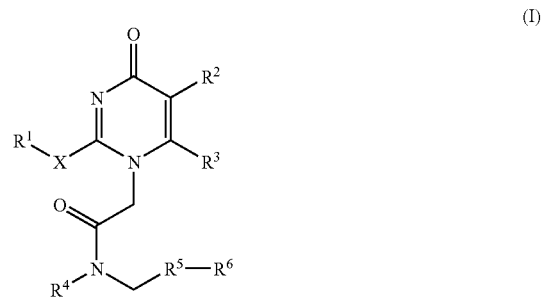

are disclosed in which:

$R^1$ is an aryl group, optionally substituted by 1, 2, 3 or 4 substituents which may be the same or different selected from $C_{(1-6)}$alkyl, $C_{(1-6)}$alkoxy, $C_{(1-6)}$alkylthio, hydroxy, halogen, CN, and mono to perfluoro-$C_{(1-4)}$alkyl;

$R^2$ is halogen, $C_{(1-3)}$alkyl, $C_{(1-3)}$alkoxy, hydroxy$C_{(1-3)}$alkyl, $C_{(1-3)}$alkylthio, $C_{(1-3)}$alkylsulphinyl, amino$C_{(1-3)}$alkyl, mono- or di-$C_{(1-3)}$alkylamino$C_{(1-3)}$alkyl, $C_{(1-3)}$alkylcarbonylamino$C_{(1-3)}$alkyl, $C_{(1-3)}$alkoxy$C_{(1-3)}$alkylcarbonylamino$C_{(1-3)}$alkyl, $C_{(1-3)}$alkylsulphonylamino$C_{(1-3)}$alkyl, $C_{(1-3)}$alkylcarboxy, $C_{(1-3)}$alkylcarboxy$C_{(1-3)}$alkyl, and $R^3$ is hydrogen, halogen, $C_{(1-3)}$alkyl, or hydroxy$C_{(1-3)}$alkcyl; or $R^2$ and $R^3$ together with the pyrimidone ring carbon atoms to which they are attached form a fused 5-or 6-membered carbocyclic ring; or $R^2$ and $R^3$ together with the pyrimidone ring carbon atoms to which they are attached form a fused benzo or heteroaryl ring ring optionally substituted by 1, 2, 3 or 4 substituents which may be the same or different selected from halogen, $C_{(1-4)}$alkyl, cyano, $C_{(1-6)}$alkoxy, $C_{(1-6)}$alkylthio or mono to perfluoro-$C_{(1-4)}$alkyl;

$R^4$ is hydrogen, $C_{(1-6)}$alkyl which may be unsubstituted or substituted by 1, 2 or 3 substituents selected from hydroxy, halogen, $OR^7$, $COR^7$, carboxy, $COOR^7$, $CONR^9R^{10}$, $NR^9R^{10}$, $NR^7COR^8$, mono- or di-(hydroxy$C_{(1-6)}$alkyl) amino and N-hydroxy$C_{(1-6)}$alkyl-N—$C_{(1-6)}$allkylamino; or $R^4$ is Het-$C_{(0-4)}$alkyl in which Het is a 5- to 7- membered heterocyclyl ring comprising N and optionally O or S, and in which N may be substituted by $COR^7$, $COOR^7$, $CONR^9R^{10}$, or $C_{(1-6)}$alkyl optionally substituted by 1, 2 or 3 substituents selected from hydroxy, halogen, $OR^7$, $COR^7$, carboxy, $COOR^7$, $CONR^9R^{10}$ or $NR^9R^{10}$, for instance, piperidinyl-4-yl, pyrrolidin-3-yl;

$R^5$ is an aryl or a heteroaryl ring optionally substituted by 1, 2, 3 or 4 substituents which may be the same or different selectd from $C_{(1-6)}$alkyl, $C_{(1-6)}$alkoxy, $C_{(1-6)}$alkylthio, aryl$C_{(1-6)}$alkoxy, hydroxy, halogen, CN, $COR^7$, carboxy, $COOR^7$, $NR^7COR^8$, $CONR^9R^{10}$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy;

$R^6$ is an aryl or a heteroaryl ring which is further optionally substituted by 1, 2, 3 or 4 substituents which may be the same or different selected from $C_{(1-18)}$alkyl, $C_{(1-18)}$alkoxy, $C_{(1-6)}$alkylthio, $C_{(1-6)}$alkylsulfonyl, aryl$C_{(1-6)}$alkoxy, hydroxy, halogen, CN, $COR^7$, carboxy, $COOR^7$, $CONR^9R^{10}$, $NR^7COR^8$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy, or $C_{(5-10)}$alkyl; These compound are useful for treating diseases associated with abnormal activity of the phospholipase $A_2$ enzyme, for example athereosclosis.

10 Claims, No Drawings

PYRIMIDINONE DERIVATIVES AND THEIR USE IN THE TREATMENT OF ATHEROSCLEROSIS

The present invention relates to certain novel pyrimidinone compounds, processes for their preparation, intermediates useful in their preparation, pharmaceutical compositions containing them and their use in therapy, in particular in the treatment of atherosclerosis.

WO 95/00649 (SmithKline Beecham plc) describes the phospholipase $A_2$ enzyme Lipoprotein Associated Phospholipase $A_2$ (Lp-PLA$_2$), the sequence, isolation and purification thereof, isolated nucleic acids encoding the enzyme, and recombinant host cells transformed with DNA encoding the enzyme. Suggested therapeutic uses for inhibitors of the enzyme included atherosclerosis, diabetes, rheumatoid arthritis, stroke, myocardial infarction, reperfusion injury and acute and chronic inflammation. A subsequent publication from the same group further describes this enzyme (Tew D et al, Arterioscler Thromb Vas Biol 1996:16;591–9) wherein it is referred to as LDL-PLA$_2$. A later patent application (WO 95/09921, Icos Corporation) and a related publication in Nature (Tjoelker et at, vol 374, Apr. 6, 1995, 549) describe the enzyme PAF-AH which has essentially the same sequence as Lp-PLA$_2$ and suggest that it may have potential as a therapeutic protein for regulating pathological inflammatory events.

It has been shown that Lp-PLA$_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-PLA$_2$ action are biologically active with lysophosphatidylcholine in particular having several pro-atherogenic activities ascribed to it, including monocyte chemotaxis and induction of endothelial dysfunction, both of which facilitate monocyte-derived macrophage accumulation within the artery wall. Inhibition of the Lp-PLA$_2$ enzyme would therefore be expected to stop the build up of these macrophage enriched lesions (by inhibition of the formation of lysophosphatidylcholine and oxidised free fatty acids) and so be useful in the treatment of atherosclerosis.

A recently published study (WOSCOPS-Packard et al, *N. Engl. J. Med.* 343 (2000) 1148–1155) has shown that the level of the enzyme Lp-PLA$_2$ is an independent risk factor in coronary artery disease.

The increased lysophosphatidylcholine content of oxidatively modified LDL is also thought to be responsible for the endothelial dysfunction-observed in patients with atherosclerosis. Inhibitors of Lp-PLA$_2$ could therefore prove beneficial in the treatment of this phenomenon. An Lp-PLA$_2$ inhibitor could also find utility in other disease states that exhibit endothelial dysfunction including diabetes, hypertension, angina pectoris and after ischaemia and reperfusion.

In addition, Lp-PLA$_2$ inhibitors may also have a general application in any disorder that involves activated monocytes, macrophages or lymphocytes, as all of these cell types express Lp-PLA$_2$. Examples of such disorders include psoriasis.

Furthermore, Lp-PLA$_2$ inhibitors may also have a general application in any disorder that involves lipid oxidation in conjunction with Lp-PLA$_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, ischaemia, reperfusion injury and acute and chronic inflammation.

Patent applications WO 96/12963, WO 96/13484, WO96/19451, WO 97/02242, WO97/217675, WO 97/217676, WO 96/41098, and WO 97/41099 (SmithKline Beecham plc) disclose inter alia various series of 4-thionyl/sulfinyl/sulfonyl azetidinone compounds which are inhibitors of the enzyme Lp-PLA$_2$. These are irreversible, acylating inhibitors (Tew et al, Biochemistry, 37, 10087, 1998).

A further class of compounds has now been identified which are non-acylating inhibitors of the enzyme Lp-PLA$_2$. Thus, WO 99/24420, WO 00/10980, WO 00/66566, WO 00/66567 and WO 00/68208 (SmithKline Beecham plc) disclose a class of pyrimidone compounds which are exemplified by an optionally substituted 2-benzylthio or 2-benzyloxy substituent. We have now found that this may be replaced by a carbon linker, to give compounds having good activity as inhibitors of the enzyme Lp-PLA$_2$.

Accordingly, the present invention provides a compound of formula (I):

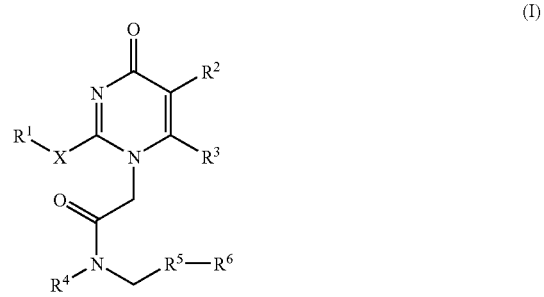

in which:

$R^1$ is an aryl group, optionally substituted by 1, 2, 3 or 4 substituents which may be the same or different selected from $C_{(1-6)}$alkyl, $C_{(1-6)}$alkoxy, $C_{(1-6)}$alkylthio, hydroxy, halogen, CN, and mono to perfluoro-$C_{(1-4)}$alkyl;

$R^2$ is halogen, $C_{(1-3)}$alkyl, $C_{(1-3)}$alkoxy, hydroxy$C_{(1-3)}$alkyl, $C_{(1-3)}$alkylthio, $C_{(1-3)}$alkylsulphinyl, amino$C_{(1-3)}$alkyl, mono- or di-$C_{(1-3)}$alkylamino$C_{(1-3)}$alkyl, $C_{(1-3)}$alkylcarbonylamino$C_{(1-3)}$alkyl, $C_{(1-3)}$alkoxy$C_{(1-3)}$alkylcarbonylamino$C_{(1-3)}$alkyl, $C_{(1-3)}$alkylsulphonylamino$C_{(1-3)}$alkyl, $C_{(1-3)}$alkylcarboxy, $C_{(1-3)}$alkylcarboxy$C_{(1-3)}$alkyl, and $R^3$ is hydrogen, halogen, $C_{(1-3)}$alkyl, or hydroxy$C_{(1-3)}$alkyl; or $R^2$ and $R^3$ together with the pyrimidone ring carbon atoms to which they are attached form a fused 5- or 6-membered carbocyclic ring; or $R^2$ and $R^3$ together with the pyrimidone ring carbon atoms to which they are attached form a fused benzo or heteroaryl ring ring optionally substituted by 1, 2, 3 or 4 substituents which may be the same or different selected from halogen, $C_{(1-4)}$alkyl, cyano, $C_{(1-6)}$alkoxy, $C_{(1-6)}$alkylthio or mono to perfluoro-$C_{(1-4)}$alkyl;

$R^4$ is hydrogen, $C_{(1-6)}$alkyl which may be unsubstituted or substituted by 1, 2 or 3 substituents selected from hydroxy, halogen, $OR^7$, $COR^7$, carboxy, $COOR^7$, $CONR^9R^{10}$, $NR^9R^{10}$, $NR^7COR^8$, mono- or di-(hydroxy$C_{(1-6)}$alkyl) amino and N-hydroxy$C_{(1-6)}$alkyl-N—$C_{(1-6)}$alkylamino; or $R^4$ is Het-$C_{(0-4)}$alkyl in which Het is a 5- to 7- membered heterocyclyl ring comprising N and optionally O or S, and in which N may be substituted by $COR^7$, $COOR^7$, $CONR^9R^{10}$, or $C_{(1-6)}$alkyl optionally substituted by 1, 2 or 3 substituents selected from hydroxy, halogen, $OR^7$, $COR^7$, carboxy, $COOR^7$, $CONR^9R^{10}$ or $NR^9R^{10}$, for instance, piperidin-4-yl, pyrrolidin-3-yl;

$R^5$ is an aryl or a heteroaryl ring optionally substituted by 1, 2, 3 or 4 substituents which may be the same or different selected from $C_{(1-6)}$alkyl, $C_{(1-6)}$alkoxy, $C_{(1-6)}$alkylthio, aryl$C_{(1-6)}$alkoxy, hydroxy, halogen, CN, $COR^7$, carboxy, $COOR^7$, $NR^7COR^8$, $CONR^9R^{10}$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy;

$R^6$ is an aryl or a heteroaryl ring which is further optionally substituted by 1, 2, 3 or 4 substituents which may be the same or different selected from $C_{(1-18)}$alyl, $C_{(1-18)}$alkoxy, $C_{(1-6)}$alkylthio, $C_{(1-6)}$alkylsulfonyl, aryl$C_{(1-6)}$alkoxy, hydroxy, halogen, CN, $COR^7$, carboxy, $COOR^7$, $CONR^9R^{10}$, $NR^7COR^8$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy, or $C_{(5-10)}$alkyl;

$R^7$ is hydrogen or $C_{(1-12)}$alkyl, for instance $C_{(1-4)}$alyl (e.g. methyl or ethyl);

$R^8$ is hydrogen, $OC_{(1-6)}$alkyl, or $C_{(1-12)}$alkyl, for instance $C_{(1-4)}$alkyl (e.g. methyl or ethyl);

$R^9$ and $R^{10}$ which may be the same or different is each selected from hydrogen, or $C_{(1-12)}$alkyl, or $R^9$ and $R^{10}$ together with the nitrogen to which they are attached form a 5- to 7 membered ring optionally containing one or more further heteroatoms selected from oxygen, nitrogen and sulphur, and optionally substituted by one or two substituents selected from hydroxy, oxo, $C_{(1-4)}$ alkyl, $C_{(1-4)}$alkylcarboxy, aryl, e.g. phenyl, or araaayi, e.g benzyl, for instance morpholine or piperazine; and X is $C_{(2-4)}$alkylene, optionally substituted by 1,2 or 3 substituents selected from methyl and ethyl, or CH=CH.

Representative examples of $R^1$ when an aryl group include phenyl and naphthyl. Preferably, $R^1$ is phenyl optionally substituted by halogen, $C_{(1-6)}$alkyl, trifluoromethyl, $C_{(1-6)}$alkoxy, preferably, from 1 to 3 fluoro, more preferably, 2,3-ifluoro.

Further representative examples of $R^1$ include phenyl substituted by trifluoromethoxy or cyano.

Representative examples of $R^2$ include methyl, ethyl, and trifluoroethyl when $R^3$ is hydrogen.

Representative examples of $R^3$ include methyl when $R^2$ is methyl.

Preferably $R^2$ is ethyl when $R^3$ is hydrogen.

Further representative examples of $R^2$ and $R^3$ include when $R^2$ and $R^3$ together with the pyrimidine ring carbon atoms to which they are attached form a fused 5-membered carbocyclic (cyclopentenyl) ring, or a fused benzo, pyrido, pyrazolo or thieno ring.

Further representative examples of $R^2$ and $R^3$ include when $R^2$ and $R^3$, together with the pyrimidine ring carbon atoms to which they are attached, form a fused benzo ring substituted by $C_{(1-4)}$alkyl, trifluoromethyl, or 1 or 2 halogen atoms; and when $R^2$ and $R^3$, together with the pyrimidine ring carbon atoms to which they are attached, form a fused thieno ring substituted by methyl.

Preferably, $R^2$ and $R^3$ together with the pyrimidine ring carbon atoms to which they are attached form a fused 5-membered carbocyclic (cyclopentenyl) ring or a fused benzo, pyrido, thieno or pyrazolo ring.

Representative examples of $R^4$ include hydrogen, methyl, 2-(diethylamino)ethyl, 2-(piperidin-1-yl)ethyl, 2-(pyrrolidin-1-yl)ethyl, 3-(morpholin-4-yl)propyl, 1-ethyl-piperidin-4-yl and 1-ethyl-pyrrolidin-2-ylmethyl. Preferably $R^4$ is 2-(diethylamino)ethyl or 1-ethyl-piperidinyl-4-yl.

Further representative examples of $R^4$ include piperidin-4-yl substituted at the 1-position by methyl, 2-methoxyethyl, isopropyl, 1-ethoxycarbonylmethyl or t-butoxycarbonyl; ethyl substituted at the 2-position by ethylamino, t-butylamino or morpholin-4-yl; 2-methylpropyl substituted in the 2-position by dimethylamino, ethylamino, (morpholin-4-yl), (piperidin-1-yl), isopropylamino, diethylamino, dimethylamino, pyrrolidin-1-ylmethyl or pyrrolidin-1-yl; propyl substituted at the 3-position by piperidin-1-yl, pyrrolidin-1-yl, diethylamino; butyl substituted at the 4-position by pyrrolidin-1-yl; 1-ethylpiperidin-4-ylmethyl; 2-methoxyethyl; t-butoxycarbonylmethyl; 2-hydroxyethyl; hydroxycarbonylmethyl; and piperidin-4-yl. Preferably $R^4$ is 1-methylpiperidin-4-yl or 1-(2-methoxyethyl )piperidin-4-yl.

Representative examples of $R^5$ include phenyl and pyridyl. Preferably, $R^5$ is phenyl.

Further representative examples of $R^5$ include thienyl, pyrimidyl and furyl. Preferably, $R^5$ is thienyl.

Representative examples of $R^6$ include phenyl optionally substituted by halogen, or trifluoromethyl, preferably at the 4-position and hexyl. Preferably, $R^6$ is phenyl substituted by trifluoromethyl at the 4-position.

Further representative examples of $R^6$ include phenyl substituted by methylthio, $C_{(1-6)}$alkyl, cyano, methylsulfonyl, piperidin-1-ylsulfonyl or pentafluoroethyl; and thienyl optionally substituted by halogen or trifluoromethyl. Preferably, $R^6$ is thien-2-yl substituted by trifluoromethyl in the 5-position.

Preferably, $R^5$ and $R^6$ together form a 4-(phenyl)phenyl or a 2-(phenyl)pyridinyl substituent in which the remote phenyl ring may be optionally substituted by halogen or trifluoromethyl, preferably at the 4-position.

In a further aspect the present invention provides a compound of formula (I) in which:

$R^7$ and $R^8$ are independently hydrogen or $C_{(1-12)}$alkyl, for instance $C_{(1-4)}$allyl (e.g. methyl or ethyl).

Representative examples of X include $(CH_2)_3$, vinyl, $(CH_2)_2$ and $(CH_2)_2$ substituted by one or more methyl. Preferably X is $C_{(2-4)}$alkylene, more preferably $C_{(2-3)}$ alkylene, most preferably, $(CH_2)_2$.

It will be appreciated that within the compounds of formula (I) there is a sub-group of compounds (group A) in which:

$R^1$ is phenyl substituted by 1 to 3 fluoro;
$R^2$ is ethyl when $R^3$ is hydrogen;
$R^4$ is 2-(diethylamino)ethyl, 1-ethyl-piperidin-4-yl, 1-methylpiperidin-4-yl or 1-(2-methoxyethyl)piperidin-4-yl;
$R^5$ is phenyl, thienyl or pyridyl;
$R^6$ is phenyl substituted by trifluoromethyl at the 4-position, or thien-2-yl substituted by trifluoromethyl in the 5-position; and
X is $(CH_2)_2$.

It will be appreciated that within the compounds of formula (I) there is a further sub-group of compounds (group B) in which:

$R^1$ is phenyl substituted by 2,3 difluoro;
$R^2$ and $R^3$, together with the pyrimidine ring carbon atoms to which they are attached, form a fused 5-membered carbocyclic (cyclopentenyl) ring or a fused benzo, pyrido, thieno or pyrazolo ring;
$R^4$ is 2-(diethylamino)ethyl, 1-ethyl-piperidin-4-yl, 1-methylpiperidin-4-yl or 1-(2-methoxyethyl)piperidin-4-yl;

$R^5$ is phenyl, thienyl or pyridyl;
$R^6$ is phenyl substituted by trifluoromethyl at the 4-position, or thien-2-yl substituted by trifluoromethyl in the 5-position; and
X is $(CH_2)_2$.

It will be appreciated that within the compounds of formula (I) there is a further sub-group of compounds (group C) in which:
$R^1$ is phenyl substituted by 2,3 difluoro;
$R^2$ and $R^3$, together with the pyrimidine ring carbon atoms to which they are attached, form a fused pyrido ring;
$R^4$ is 1-methylpiperidin-4-yl or 1-(2-methoxyethyl)piperidin-4-yl;
$R^5$ and $R^6$ together form a 4-(phenyl)phenyl in which the remote phenyl ring is substituted by trifluoromethyl, preferably at the 4-position; and
X is $(CH_2)_2$.

It will be appreciated that compounds of the present invention may comprise one or more chiral centres so that stereoisomers may be formed. The present invention covers all such stereoisomers, including individual diastereoisomers and enantiomers, and mixtures thereof.

It will be appreciated that in some instances, compounds of the present invention may include a basic function such as an amino group as a substituent. Such basic functions may be used to form acid addition salts, in particular pharmaceutically acceptable salts. Pharmaceutically acceptable salts include those described by Berge, Bighley, and Monkhouse, *J. Pharm. Sci.*, 1977, 66, 1–19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, taurocholic acid, benzenesulfonic, p-toluenesulfonic, hydrochloric, hydrobromic, sulfuiric, cyclohexylsulfamic, phosphoric and nitric acids.

It will be appreciated that in some instances, compounds of the present invention may include a carboxy group as a substituent. Such carboxy groups may be used to form salts, in particular pharmaceutically acceptable salts. Pharmaceutically acceptable salts include those described by Berge, Bighley, and Monkhouse, *J. Pharm. Sci.*, 1977, 66, 1–19. Preferred salts include alkali metal salts such as the sodium and potassium salts.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the term "aryl" refers to, unless otherwise defined, a mono- or bicyclic aromatic ring system containing up to 10 carbon atoms in the ring system, for instance phenyl or naphthyl.

When used herein, the term "heteroaryl" refers to a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When used herein, the terms "halogen" and "halo" include fluorine, chlorine, bromine and iodine and fluoro, chloro, bromo and iodo, respectively.

Most preferred compounds of formula (I) are:
N-(1-Methylpiperidin-4-yl)-2-(2-(2,3-difluorophenyl)ethyl)-4-oxo-4H-pyrido[2,3-d]pyrimidin-1-yl)-N-(4-(4-trifluoromethylphenyl)phenyl)methylacetamide;

N-(1-(2-Methoxyethyl)pipezidin-4-yl)-(2-(2-(2,3-difluorophenyl)ethyl)-4-oxo-4H-pyrido[2,3-d]pyrimidin-1-yl)-N-(4-(4-trifluoromethylphenyl)phenyl)methylacetamide;

or a pharmaceutically acceptable salt thereof, in particular the bitartate salt.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are re-crystallised from organic solvents, solvent of crystallisation may be present in the crystalline product. This invention includes within its scope such solvates. Similarly, some of the compounds of this invention may be crystallised or re-crystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase $A_2$ (Lp-PLA$_2$) and as such are expected to be of use in therapy, in particular in the treatment of atherosclerosis. In a further aspect therefore the present invention provides a compound of formula (I) for use in therapy.

The compounds of formula (I) are inhibitors of lysophosphatidylcholine production by Lp-PLA$_2$ and may therefore also have a general application in any disorder that involves endothelial dysfunction, for example atherosclerosis, diabetes, hypertension, angina pectoris and after ischaemia and reperfusion. In addition, compounds of formula (I) may have a general application in any disorder that involves lipid oxidation in conjunction with enzyme activity, for example in addition to conditions such as atherosclerosis and diabetes, other conditions such as rheumatoid arthritis, stroke, inflammatory conditions of the brain such as Alzheimer's Disease, myocardial infarction, reperfusion injury, sepsis, and acute and chronic inflamnmation.

Further applications include any disorder that involves activated monocytes, macrophages or lymphocytes, as all of these cell types express Lp-PLA$_2$. Examples of such disorders include psoriasis.

Accordingly, in a further aspect, the present invention provides for a method of treating a disease state associated with activity of the enzyme Lp-PLA$_2$ which method involves treating a patient in need thereof with a therapeutically effective amount of an inhibitor of the enzyme. The disease state may be associated with the increased involvement of monocytes, macrophages or lymphocytes; with the formation of lysophosphatidylcholine and oxidised free fatty acids; with lipid oxidation in conjunction with Lp PLA$_2$ activity; with ischemia and reperfusion; or with endothelial dysfunction.

Compounds of the present invention may also be of use in treating the above mentioned disease states in combination with an anti-hyperlipidaemic, anti-atherosclerotic, anti-diabetic, anti-anginal, anti-inflammatory, or anti-hypertension agent or an agent for lowering Lp(a). Examples of the above include cholesterol synthesis inhibitors such as statins, antioxidants such as probucol, insulin sensitisers, calcium channel antagonists, and anti-inflammatory drugs such as NSAIDs. Examples of agents for lowering Lp(a) include the aminophosphonates described in WO 97/02037, WO 98/28310, WO 98/28311 and WO 98/28312 (Symphar S A and SmithKline Beecham).

A preferred combination therapy will be the use of a compound of the present invention and a statin. The statins are a well known class of cholesterol lowering agents and include atorvastatin, simvarstatin, pravastatin, cerivastatin, fluvastatin, lovastatin and rosuvastatin (also referred to as S-4522 or ZD 4522, Astra Zeneca). The two agents may be administered at substantially the same time or at different times, according to the discretion of the physician.

A further preferred combination therapy will be the use of a compound of the present invention and an anti-diabetic agent or an insulin sensitiser, as coronary heart disease is a major cause of death for diabetics. Within this class, preferred compounds for use with a compound of the present invention include the PPARgamma activators, for instance GI262570 (GlaxoSmithKline) and the glitazone class of compounds such as rosiglitazone (Avandia, GlaxoSmithKline), troglitazone and pioglitazone.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier.

Suitable pharmaceutical compositions include those which are adapted for oral or parenteral administration or as a suppository.

Suitable pharmaceutical compositions include those which are adapted for oral or parenteral administration or as a suppository. Compounds of formula (I) which are active when given orally can be formulated as liquids, for example syrups, suspensions or emulsions, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule. Each dosage unit for oral administration contains preferably from 1 to 500 mg (and for parenteral administration contains preferably from 0.1 to 25 mg) of a compound of the formula (I). The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

A compound of formula (I) may be prepared by reacting an acid compound of formula (II):

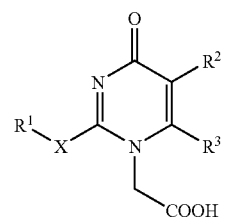

(II)

in which X, R$^1$, R$^2$ and R$^3$ are as hereinbefore defined, with an amine compound of formula (III):

(III)

in which R$^4$, R$^5$ and R$^6$ are as hereinbefore defined; under amide forming conditions.

Suitable amide forming conditions are well known in the art and include treating the acid of formula (II) with the amine of formula (III) in the presence of a coupling agent such as 1-(3-dimethyl-aminopropyl)-3-ethylcarbodiimide (DEC), or O-(7-azabenzotriazol-1-yl)-N,N,N',N'-tetramethyluronium hexafluorophosphate (HATU), preferably in the presence of di-isopropylethylamine.

A compound of formula (II) may be readily prepared from a corresponding unsubstituted pyrimidone compound of formula (IV):

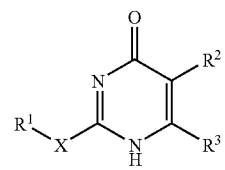

(IV)

in which X, R$^1$, R$^2$ and R$^3$ are as hereinbefore defined, by reaction with a compound of formula (V):

(V)

in which L is a leaving group such as halo, for example, iodo, and $R^{11}$ is $C_{(1-6)}$alkyl, for example t-butyl, in the presence of a base such as a tertiary amine, for example di-isopropylethylamine; to form an intermediate ester (VI),

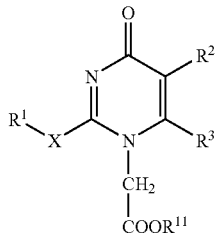

(VI)

in which X, $R^1$, $R^2$, $R^3$ and $R^{11}$ are as hereinbefore defined, and thereafter, removing $R^{11}$, by treating with a de-esterifying agent, for instance, for t-butyl, trifluoroacetic acid.

It will be appreciated that removal of $R^{11}$ may be carried out as a separate step, so that an acid of formula (II) is isolated or, alternatively, that the acid of formula (II) is formed from the intermediate ester (VI) as a preliminary first step, prior to reaction with an amme of formula (III).

The pyrimidone of formula (IV) may be readily prepared by adapting a standard pyrimidone synthesis involving an amidine and a 1,3-dicarbonyl compound, by reacting an amidine of formula (VII):

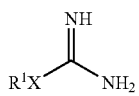

(VII)

in which $R^1$ and X are as hereinbefore defined, preferably as a salt thereof, for instance the hydrochloride salt, with a compound of formula (VIII):

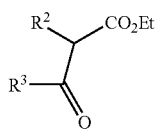

(VIII)

in which $R^2$ and $R^3$ are as hereinbefore defined.

It will be appreciated that in the compound of formula (IV), when $R^3$, is hydrogen, the compound of formula (VIII) is a 1,3-aldehyde ester and further, that in the compound of formula (IV), when $R^3$ is other than hydrogen, the compound of formula (VIII) is a 1,3-keto ester.

For compounds of formula (II) in which $R^2$ and $R^3$ together with the pyrimidone ring carbon atoms to which they are attached form a fused benzo or heteroaryl ring optionally substituted by halogen, $C_{(1-6)}$alkyl, cyano, mono to perfluoro-$C_{(1-4)}$alkyl, it is found more convenient to adopt a slightly different strategy whereby the amidine of formula (VII) is reacted with a compound of the formula (IX):

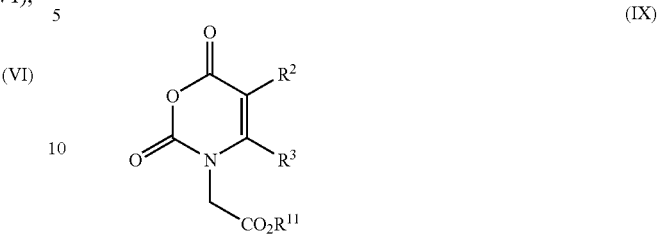

(IX)

in which $R^2$ and $R^3$ together with the pyrimidone ring carbon atoms to which they are attached form a fused benzo or heteroaryl ring optionally substituted by halogen, $C_{(1-6)}$alkyl, cyano, mono to perfluoro-$C_{(1-4)}$alkyl, and $R^{11}$ is as hereinbefore defined, for example ethyl, under standard pyrimidone ring forming conditions, in the presence of a base such as pyridine, to give an intermediate ester (VI) which can then be converted into a compound of formula (II), for instance by treatment with aqueous sodium hydroxide.

Alternatively, for compounds of formula (II) in which $R^2$ and $R^3$ together with the pyrimidone ring carbon atoms to which they are attached form a fused benzo or heteroaryl ring optionally substituted by halogen, $C_{(1-6)}$alkyl, cyano, mono to perfluoro-$C_{(1-4)}$alkyl, the pyrimidone ring may be formed by reacting a compound of formula (X):

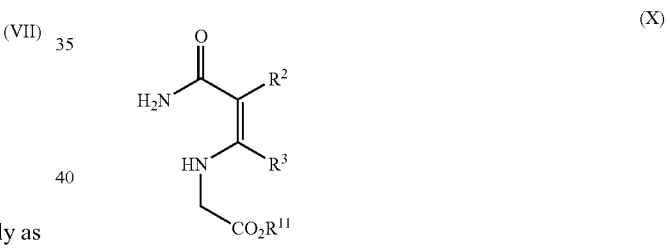

(X)

in which $R^2$ and $R^3$ together with the pyrimidone ring carbon atoms to which they are attached form a fused benzo or heteroaryl ring optionally substituted by halogen, $C_{(1-6)}$alkyl, cyano, mono to periluoro-$C_{(1-4)}$alkyl, and $R^{11}$ is as hereinbefore defined, for example ethyl, with an acyl chloride compound of the formula (XI):

(XI)

in which $R^1$ and X are as hereinbefore defined; under standard pyrimidone ring forming conditions, in a solvent such as benzene, or via a two step procedure by treatment with pyridine, followed by a suitable base e.g. NaH in DMF, followed by treatment of the intermediate so formed with an acid e.g. p-toluene sulfonic acid in refluxing toluene; to give an intermediate ester (VI) which can then be converted into a compound of formula (II), for instance by treatment with aqueous sodium hydroxide.

It will be appreciated by those skilled in the art that all other starting materials and intermediates are either known compounds or may be prepared by literature methods, such as those described in "Comprehensive Organic Transformations: a guide to functional group preparations" by Richard Larock (VCH, 1989), incorporated herein by reference.

The present invention will now be illustrated by the following examples.

EXAMPLES

The structure and purity of the intermediates and examples was confirmed by 1H-NMR and (in nearly all cases) mass spectroscopy, even where not explicitly indicated below.

Intermediate A1—3-(2,3-Difluorophenyl)propionic acid

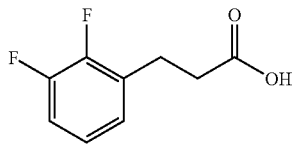

A solution of 2,3-difluorocinnamic acid (9.14 g) in ethanol (250 ml) with 10% palladium/carbon catalyst was hydrogenated for 5 h at room temperature and atmospheric pressure. The reaction mixture was filtered through celite and concentrated in vacuo to give the title compound as a colourless solid (9.05 g, quant.) $^1$H-NMR (CDCl$_3$) δ 2.70 (2H, t), 3.02 (2H, t) and 7.01 (3H, m).

Intermediate A2—3-(2,3-Difluorophenyl)propanenitrile

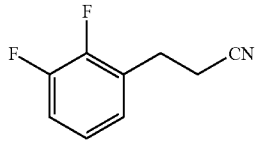

To a solution of 3-(2,3-difluorophenyl)-propionic acid (A1) (6.83 g, 36 mmol) in anhydrous dichloromethane (50 ml) containing a few drops of DMF was added oxalyl chloride (6.4 ml, 73 mmol) at 0° C. under argon. The solution was stirred at ambient temperature for 2 h and the solvent removed in vacuo. The residue was dissolved in sulfolane (30 ml) and added to sulfamide (4.23 g, 44 mmol) and the mixture heated at 120° C. for 3 h. The brown solution was cooled, poured into 2M sodium hydroxide solution (300 ml) and extracted with ether. The combined extracts were washed with water, dried (MgSO$_4$) and evaporated to give the title compound as a brown oil (6.04 g, 98%). $^1$H-NMR (CDCl$_3$) δ 2.68 (2H, t), 3.04 (2H, t), 7.01–7.15 (3H, m).

Intermediate A3—3-(2,3-Difluorophenyl)propionamidine hydrochloride

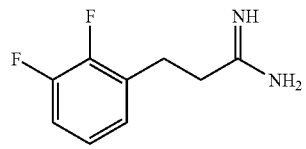

A solution of 3-(2,3-difluorophenyl)-propionitrile (Int A2) (6.04 g) in saturated ethanolic hydrogen chloride (30 ml) was stirred at ambient temperature overnight then concentrated to a brown solid. The residue was triturated with ether, dissolved in ethanol (50 ml) and the solution saturated with ammonia gas. The mixture was stirred at room temperature overnight, concentrated and the residue triturated with ether to give the title compound as a white solid (7.02 g, 88%). $^1$H-NMR (DMSO) δ 2.72 (2H, t), 3.06 (2H, t), 7.16–7.36 (3H, m), 8.77 (2H, s), 9.16 (2H, s).

Intermediate A4—4-(4Fluorophenyl)-butyramide

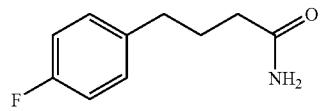

To a solution of 4-(4-fluorophenyl)-butyric acid (6.7 g) in chloroform (15 ml) at 0° C. was added 0.1 ml DMF followed by the addition of oxalyl chloride (3.35 ml) over 20 min. The solution was stirred for 2 h then concentrated. The crude acid chloride was dissolved in chloroform (150 ml) and cooled to 0° C., whereupon concentrated ammonia solution (6 ml) was added over 15 min and the resulting solution stirred for 2 h. The reaction mixture was washed with water and the organic phase dried (MgSO$_4$) and concentrated in vacuo. The crude product was chromatographed over silica using a gradient elution from ether to 2:1 acetone/ether to yield the title compound (2.86 g, 43%). $^1$H-NMR (CDCl$_3$) δ 1.96 (2H, app q), 2.21 (2H, t), 2.65 (2H, t), 5.41 (2H, br s), 6.96 (2H, m), 7.14 (2H, m). MS(APCI+)M+1=182, C$_{10}$H$_{12}$FNO requires 181.

Intermediate A5—4-(4-Fluorophenyl)-butyronitrile

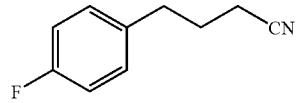

4(4-Fluorophenyl)-butyramide (Int. A4) (2.63 g) was dissolved in trifluoroacetic anhydride (10 ml) and stirred for 2 h. The solution was concentrated and then dissolved in dichloromethane and washed with 2N sodium hydroxide solution. The organics extracts were isolated, dried (MgSO$_4$) and concentrated to yield the product (2.3 g, 100%) which contained ~5% starting amide as an impurity. $^1$H-NMR (CDCl$_3$) δ 1.96 (2H, app q), 2.31 (2H, t), 2.75 (2H, t), 6.98 (2H, m), 7.14 (2H, m). MS (APCI+)M+1=164, C$_{10}$H$_{10}$FN requires 163.

Intermediate A6—Benzyl (E)-3-(3-cyano-4-fluorophenyl)-acrylate

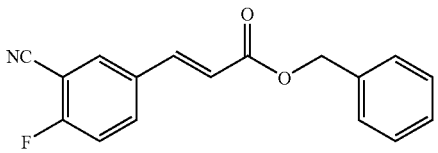

To a solution of 3-cyano-4-fluorobenzaldehyde (2.00 g, 13.4 mmol) in dichloromethane (50 ml) was added benzyl triphenylphosphoanylidene acetate (5.51 g, 13.4 mmol) portionwise over 15 min. The reaction mixture was stirred for 2 h, concentrated and the residues chromatographed over silica with a gradient elution using 1:1 hexane/dichloromethane to dichloromethane to yield product as a white solid (3.27 g, 87%). $^1$H-NMR (CDCl$_3$) δ 5.26 (2H, s), 6.08 (1H, d), 7.2–7.5 (6H, m), 7.6 (1H, d), 7.75 (2H, d).

Intermediate A7—3-(3-Cyano-4-fluorophenyl)-propionic acid

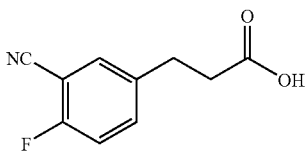

Benzyl (E)-3-(3-cyanofluorophenyl)-acrylate (Int. A6) (1.72 g, 6.1 mmol) was dissolved in 1:1 dichloromethane/ethanol (50 ml) and 10% palladium on charcoal (0.5 g) added. The mixture was hydrogenated for 2 h at ambient pressure, filtered and concentrated to provide the title compound as a white solid (1.2 g, 100%). $^1$H-NMR (CDCl$_3$) δ 2.69 (2H, t), 2.97 (2H, t), 7.11 (1H, m), 7.43 (3H, m).

Intermediate A8—3-(3-Cyano-4-fluorophenyl)-propionyl chloride

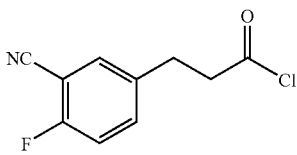

3-(3'-Cyano-4-fluorophenyl)-propionic acid (Int. A7) was dissolved in dichloromethane (30 ml) containing 0.1 ml DMF and oxalyl chloride (0.79 g, 6.2 mmol) added dropwise over 5 min. The reaction mixture was stirred for 2 h then concentrated in vacuo to yield the title compound as an oil (1.3 g, 100%). $^1$H-NMR (CDCl$_3$) δ 3.02 (2H, t), 3.21 (2H, t), 7.13 (1H, t), 7.45 (2H, m).

Intermediate A9—E-3-(4-Fluorophenyl)acrylonitrile

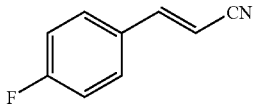

A suspension of 3-(4-fluorophenyl)acrylic acid (2.5 g, 15 mmol) in dry dichloromethane (50 ml) was treated with DMF (2 drops), oxalyl chloride (2.6 ml, 30 mmol) and the reaction was stirred at room temperature under argon for 3 h. The reaction mixture was evaporated to dryness and azeotroped with dichloromethane (25 ml×2) and evaporated to dryness giving a yellow oil. The acid chloride was mixed with sulfolane (15 ml) and treated with sulfamide (1.73 g, 0.018 moles) (A. Hulkenberg and J. J. Troost, Tetrahedron Letters Vol. 23, No. 14, 1505–1508, 1982) and the reaction mixture was heated to 120° C. for 3 h. The reaction mixture was cooled, poured into 1N NaOH (100 ml) and extracted with 1:1 diethyl ether:hexane (3×75 ml). The organic extracts were combined, washed with water (3×50 ml), dried (MgSO$_4$) and evaporated to dryness. Purification by flash column chromatography eluted with 2:1 hexane:ethyl acetate gave E-3-(4-fluorophenyl)acrylonitrile as a cream solid (2.12 g, 96%); $^1$H-NMR (CDCl$_3$) 5.77, 5.83 (1H, d), 7.16 (2H, m), 7.26, 7.40 (1H, d), 7.45 (2H, m). MS(APCI+) M+1=148, C$_9$H$_6$FN requires 147.

Intermediate A10—E-3-(4-Fluorophenyl)acrylamidine hydrochloride

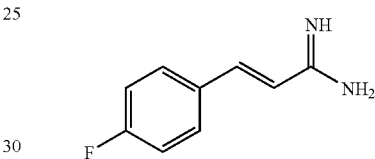

E-3-(4-fluorophenyl)acrylonitrile (Int. A9) (1.0 g, 6.8 mmol) in dry ethanol (35 ml) was cooled in an ice-bath and HCl (gas) was bubbled into the solution for 10 minutes. The mixture was allowed to stand at room temperature for 133 h. The reaction mixture was evaporated to dryness and the residue was suspended in diethyl ether (20 ml) and the yellow solid was collected by filtration and dried to give E-3-(4-fluorophenyl)acrylimidic acid ethyl ester hydrochloride (0.86 g, 55%); $^1$H-NMR (d$_6$-DMSO) 1.45 (3H, t,), 4.52 (2H, q), 6.94, 7.00 (1H, d), 7.36 (2H, m), 7.81 (2H, m), 7.92, 7.99 (1H, d), 11.5 (1H, bs); MS (APCI+)M+1=194, C$_{11}$H$_{12}$FNO requires 193.

A solution of E-3-(4-fluorophenyl)acrylimidic acid ethyl ester hyrochloride (0.86 g, 0.00374 moles) in dry methanol (20 ml) was treated with a solution of ammonia (0.064 g, 3.8 mmol) in dry methanol (0.51 ml) and the resulting solution was allowed to stand at room temperature for 48 h. The reaction mixture was evaporated to dryness, mixed with diethyl ether and evaporated to give E-3-(4-fluorophenyl) acrylamidine hydrochloride as a solid (0.75 g, 100%); $^1$H-NMR (d$_6$-DMSO) 6.72, 6.79 (1H, d) 7.35 (2H, m), 7.67 (2H, m), 7.87, 7.94 (1H, d), 8.8, 9.15 (2×bs). MS (APCl+) M+1=165, C$_9$H$_9$FN$_2$ requires 164.

Intermediate A14—(E/Z)-3-(2-(trifluoromethyl)-4-fluorophenyl)-acrylonitrile

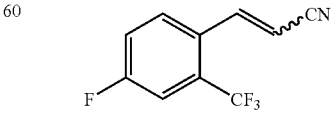

Diethyl cyanomethylphosphonate (9 ml) was added to a suspension of NaH (2.1 g) in THF (50 ml) and DMF (50 ml)

at 0° C., warmed to room temperature for 20 min and then cooled to 0° C. A solution of 2-(trifluoromethyl)-4-fluorobenzaldehyde (10 g) in TBIF (50 ml) was added and the reaction mixture allowed to warm to room temperature and stirred for 3 h. The mixture was diluted with saturated aq. NH$_4$Cl solution and extracted with diethyl ether. The organic extracts were washed with water, dried, and evaporated to give an oil. This oil was chromatographed (silica, dichloromethane/hexane) to give the title compound (1:1 E/Z mixture) as a semi-solid (8.5 g). $^1$H-NMR (CDCl$_3$) 5.67 (0.5H, dd), 5.86 (0.5H, d), 7.3–7.4 (2.5H, m), 7.4, 7.5 (1H, d), 8.0–8.1 (0.5H, m).

Intermediate A15—3-(2-(trifluoromethyl)-4-fluorophenyl)-propionitrile

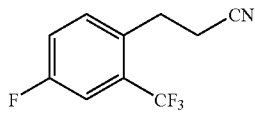

(E/Z)-3-(2-(trifluoromethyl)-4-fluorophenyl)-acrylonitrile (Int. A14) (7.5 g) in methanol (300 ml) was treated with Pd/C (100 mg) and hydrogenated for 6 h. The mixture was filtered and the filtrate evaporated to give the title compound as a oil (6 g). $^1$H-NMR (CDCl$_3$) δ 2.64 (2H, t), 3.12 (2H, t), 7.22–7.30 (1H, m), 7.36–7.46 (2H, m).

The following intermediates were made by the method of Intermediate A1:

| No. | Precursor | Name |
| --- | --- | --- |
| A20 | 3-(2,4-Difluorophenyl)acrylic acid | 3-(2,4-Difluorophenyl)propionic acid |
| A21 | 3-(2,5-Difluorophenyl)acrylic acid | 3-(2,5-Difluorophenyl)propionic acid |
| A22 | 3-(2,6-Difluorophenyl)acrylic acid | 3-(2,6-Difluorophenyl)propionic acid |
| A23 | 3-(3,5-Difluorophenyl)acrylic acid | 3-(3,5-Difluorophenyl)propionic acid |
| A24 | 3-(2-Fluorophenyl)acrylic acid | 3-(2-Fluorophenyl)propionic acid |
| A25 | 3-(3-Fluorophenyl)acrylic acid | 3-(3-Fluorophenyl)propionic acid |
| A26 | 3-(2,3,4-Trifluorophenyl)acrylic acid | 3-(2,3,4-Trifluorophenyl)propionic acid |
| A27 | 3-(2,3,5-Trifluorophenyl)acrylic acid | 3-(2,3,5-Trifluorophenyl)propionic acid |
| A28 | 3-(2,4,5-Trifluorophenyl)acrylic acid | 3-(2,4,5-Trifluorophenyl)propionic acid |
| A29 | 3-(3,4,5-Trifluorophenyl)acrylic acid | 3-(3,4,5-Trifluorophenyl)propionic acid |
| A30 | 3-(3-Cyanophenyl)acrylic acid | 3-(3-Cyanophenyl)propionic acid |

The following intermediates were made by the method of Intermediate A6:

| No. | Precursor | Name |
| --- | --- | --- |
| A31 | 2,3,6-trifluoro-benzaldehyde | Benzyl (E)-3-(2,3,6-trifluorophenyl)-acrylate |
| A32 | 2,4,6-trifluoro-benzaldehyde | Benzyl (E)-3-(2,4,6-trifluorophenyl)-acrylate |

The following intermediates were made by the method of Intermediate A7:

| No. | Precursor | Name |
| --- | --- | --- |
| A33 | Benzyl (E)-3-(2,3,6-trifluorophenyl)-acrylate (A31) | 3-(2,3,6-Trifluorophenyl)propionic acid |
| A34 | Benzyl (E)-3-(2,4,6-trifluorophenyl)-acrylate (A32) | 3-(2,4,6-Trifluorophenyl)propionic acid |

The following intermediates were made by the method of Intermediate A14:

| No. | Precursor | Name |
| --- | --- | --- |
| A36 | 3-(trifluoromethyl)-4-fluoro-benzaldehyde | (E/Z)-3-(3-(trifluoromethyl)-4-fluorophenyl)-acrylonitrile |
| A37 | 3-chloro-4-fluoro-benzaldehyde | (E/Z)-3-(3-chloro-4-fluorophenyl)-acrylonitrile |

The following intermediates were made by the method of Intermediate A15:

| No. | Precursor | Name |
| --- | --- | --- |
| A38 | (E/Z)-3-(3-(trifluoromethyl)-4-fluoro phenyl)-acrylonitrile (A36) | 3-(3-(trifluoromethyl)-4-fluorophenyl)-propanenitrile |
| A39 | (E/Z)-3-(3-chloro-4-fluorophenyl)-acrylonitrile (A37) | 3-(3-chloro-4-fluorophenyl)- |

The following acid chloride intermediates were made from the corresponding acids by the method of Intermediate A8:

| No. | Precursor | Name |
| --- | --- | --- |
| A51 | A20 | 3-(2,4-Difluorophenyl)propionyl chloride |
| A52 | A22 | 3-(2,6-Difluorophenyl)propionyl chloride |
| A53 | A23 | 3-(3,5-Difluorophenyl)propionyl chloride |
| A54 | A1 | 3-(2,3-Difluorophenyl)propionyl chloride |
| A55 | 3-(3,4-Difluorophenyl)propionic acid | 3-(3,4-Difluorophenyl)propionyl chloride |
| A56 | A24 | 3-(2-Fluorophenyl)propionyl chloride |
| A57 | A25 | 3-(3-Fluorophenyl)propionyl chloride |
| A59 | A26 | 3-(2,3,4-Trifluorophenyl)propionyl chloride |
| A60 | A27 | 3-(2,3,5-Trifluorophenyl)propionyl chloride |
| A61 | A28 | 3-(2,4,5-Trifluorophenyl)propionyl chloride |
| A62 | A29 | 3-(3,4,5-Trifluorophenyl)propionyl chloride |
| A63 | A30 | 3-(3-Cyanophenyl)propionyl chloride |
| A64 | A33 | 3-(2,3,6-Trifluorophenyl)propionyl chloride |
| A65 | A34 | 3-(2,4,6-Trifluorophenyl)propionyl chloride |

-continued

| No. | Precursor | Name |
|---|---|---|
| A66 | 3-methyl-3-phenylbutyric acid | 3-methyl-3-phenylbutyryl chloride |
| A67 | 2-methyl-3-phenylprioponic acid | 2-methyl-3-phenylpropionyl chloride |

The following nitrile intermediates were made from the corresponding acids by the method of Intermediate A2:

| No. | Precursor | Name |
|---|---|---|
| A71 | 3-phenyl-butyric acid | 3-phenyl-butyronitrile |
| A72 | A20 | 3-(2,4-Difluorophenyl)propanenitrile |
| A73 | A21 | 3-(2,5-Difluorophenyl)propanenitrile |
| A74 | 3-(3,4-Difluorophenyl)propionic acid | 3-(3,4-Difluorophenyl)propanenitrile |
| A75 | A24 | 3-(2-fluorophenyl)propanenitrile |
| A76 | A25 | 3-(3-fluorophenyl)propanenitrile |
| A77 | 3-(3-chlorophenyl)propionic acid | 3-(3-chlorophenyl)propanenitrile |
| A78 | 3-(4-chlorophenyl)propionic acid | 3-(4-chlorophenyl)propanenitrile |
| A79 | 3-(4-methylphenyl)propionic acid | 3-(4-methylphenyl)propanenitrile |
| A80 | 3-(4-(trifluoromethyl)phenyl)propionic acid | 3-(4-(trifluoromethyl)phenyl)propanenitrile |
| A81 | 3-(4-methoxyphenyl)propionic acid | 3-(4-methoxyphenyl)propanenitrile |
| A82 | 3-(4-(trifluoromethoxy)phenyl)propionic acid | 3-(4-(trifluoromethyl)phenyl)propanenitrile |
| A85 | A26 | 3-(2,3,4-Difluorophenyl)propanenitrile |

The following intermediate was made by the method of Intermediate A4:

| No. | Precursor | Name |
|---|---|---|
| A83 | 3-(4-fluorophenyl)propionic acid | 3-(4-fluorophenyl)propanamide |

The following intermediate was made by the method of Intermediate A5:

| No. | Precursor | Name |
|---|---|---|
| A84 | 3-(4-fluorophenyl)propanamide (A83) | 3-(4-fluorophenyl)propanenitrile |

The following amidine intermediates were made from the corresponding nitriles by the method of Intermediate A3:

| No. | Precursor | Name |
|---|---|---|
| A91 | A15 | 3-(2-(trifluoromethyl)-4-fluorophenyl)-propionamidine hydrochloride |
| A93 | A38 | 3-(3-(trifluoromethyl)-4-fluorophenyl)-propionamidine hydrochloride |

-continued

| No. | Precursor | Name |
|---|---|---|
| A94 | A39 | 3-(3-chloro-4-fluorophenyl)-propionamidine hydrochloride |
| A95 | A71 | 3-phenyl-butyramidine hydrochloride |
| A97 | A72 | 3-(2,4-Difluorophenyl)-propionamidine hydrochloride |
| A98 | A73 | 3-(2,5-Difluorophenyl)-propionamidine hydrochloride |
| A99 | A74 | 3-(3,4-Difluorophenyl)-propionamidine hydrochloride |
| A100 | A75 | 3-(2-fluorophenyl)-propionamidine hydrochloride |
| A101 | A76 | 3-(3-fluorophenyl)-propionamidine hydrochloride |
| A102 | A77 | 3-(3-chlorophenyl)-propionamidine hydrochloride |
| A103 | A78 | 3-(4-chlorophenyl)-propionamidine hydrochloride |
| A104 | A79 | 3-(4-methylphenyl)-propionamidine hydrochloride |
| A105 | A80 | 3-(4-(trifluoromethyl)phenyl)-propionamidine hydrochloride |
| A106 | A81 | 3-(4-methoxyphenyl)-propionamidine hydrochloride |
| A107 | A82 | 3-(4-(trifluoromethoxy)phenyl)-propionamidine hydrochloride |

| No. | Precursor | Name |
|---|---|---|
| A108 | A84 | 3-(4-fluorophenyl)-propionamidine hydrochloride |
| A110 | 3-phenyl-propanenitrile | 3-phenyl-propionamidine hydrochloride |
| A111 | 3-(2-chlorophenyl)-propanenitrile | 3-(2-chlorophenyl)-propionamidine hydrochloride |
| A112 | A5 | 4-(4-fluorophenyl)-butyramidine propionamidine hydrochloride |
| A113 | A85 | 3-(2,3,4-trifluorophenyl)-propionamidine hydrochloride |

Intermediate B1—2-[2-(2,3-Difluorophenyl)ethyl]-1,5,6,7-tetrahydrocyclopentapyrimidin-4-one

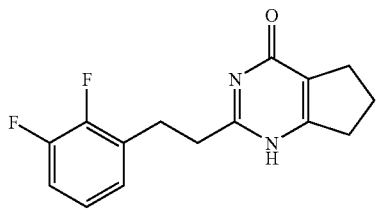

To a solution of 3-(2,3-difluorophenyl)-propionamidine hydrochloride (Int. A3) (3.90 g, 17.7 mmol) in ethanol (80 ml) was added sodium ethoxide (1.44 g, 21.2 mmol) in portions and resulting slurry stirred at ambient temperature for 1 h. 2-Oxo-cyclopentanecarboxylic acid ethyl ester (3.09 ml, 21.2 mmol) was then added and the mixture refluxed for 2 days. Evaporation of the reaction mixture followed by chromatography (silica, dichloromethane-acetone) gave the title compound (2.76 g, 56%) as a cream solid. $^1$H-NMR (DMSO) δ 1.94 (2H, m), 2.59 (2H, t), 2.72 (2H, t), 2.82 (2H, t), 3.05 (2H, t), 7.07–7.29 (3H, m), 12.20 (1H, s); MS (APCI+) found (M+1)=277; $C_{15}H_{14}F_2N_2O$ requires 276.

The following intermediates were made by the method of Intermediate B1:

| No. | Precursors | Name |
|---|---|---|
| B2 | A91 | 2-[2-(2-trifluoromethyl-4-fluorophenyl)-ethyl]-1,5,6,7-tetrahydro-cyclopentapyrimidin-4-one |
| B3 | A93 | 2-[2-(3-trifluoromethyl-4-fluorophenyl)-ethyl]-1,5,6,7-tetrahydro-cyclopentapyrimidin-4-one |
| B4 | A94 | 2-[2-(3-chloro-4-fluorophenyl)-ethyl]-1,5,6,7-tetrahydro-cyclopentapyrimidin-4-one |
| B5 | A95 | 2-[2-phenyl-prop-1-yl]-1,5,6,7-tetrahydro-cyclopentapyrimidin-4-one |
| B6 | A97 | 2-[2-(2,4-Difluorophenyl)-ethyl]-1,5,6,7-tetrahydro-cyclopentapyrimidin-4-one |
| B7 | A98 | 2-[2-(2,5-Difluorophenyl)-ethyl]-1,5,6,7-tetrahydro-cyclopentapyrimidin-4-one |
| B8 | A99 | 2-[2-(3,4-Difluorophenyl)-ethyl]-1,5,6,7-tetrahydro-cyclopentapyrimidin-4-one |
| B9 | A100 | 2-[2-(2-Fluorophenyl)-ethyl]-1,5,6,7-tetrahydro-cyclopentapyrimidin-4-one |
| B10 | A101 | 2-[2-(3-Fluorophenyl)-ethyl]-1,5,6,7-tetrahydro-cyclopentapyrimidin-4-one |
| B11 | A102 | 2-[2-(3-Chlorophenyl)-ethyl]-1,5,6,7-tetrahydro-cyclopentapyrimidin-4-one |
| B12 | A103 | 2-[2-(4-Chlorophenyl)-ethyl]-1,5,6,7-tetrahydro-cyclopentapyrimidin-4-one |
| B13 | A104 | 2-[2-(4-Methylphenyl)-ethyl]-1,5,6,7-tetrahydro-cyclopentapyrimidin-4-one |
| B14 | A105 | 2-[2-(4-(trifluoromethyl)phenyl)-ethyl]-1,5,6,7-tetrahydro-cyclopenta-pyrimidin-4-one |
| B15 | A106 | 2-[2-(4-Methoxyphenyl)-ethyl]-1,5,6,7-tetrahydro-cyclopentapyrimidin-4-one |
| B16 | A107 | 2-[2-(4-(trifluoromethoxy)phenyl)-ethyl]-1,5,6,7-tetrahydro-cyclopenta-pyrimidin-4-one |
| B17 | A108 | 2-[2-(4-fluorophenyl)-ethyl]-1,5,6,7-tetrahydro-cyclopentapyrimidin-4-one |
| B18 | A110 | 2-[2-phenyl-ethyl]-1,5,6,7-tetrahydro-cyclopentapyrimidin-4-one |
| B19 | A111 | 2-[2-(2-chlorophenyl)-ethyl]-1,5,6,7-tetrahydro-cyclopentapyrimidin-4-one |
| B20 | A112 | 2-[3-(4-fluorophenyl)-propyl]-1,5,6,7-tetrahydro-cyclopentapyrimidin-4-one |
| B21 | A10 | (E)-2-[2-(4-fluorophenyl)-vinyl]-1,5,6,7-tetrahydro-cyclopentapyrimidin-4-one |

Intermediate1 B40—5-Ethy-2-[2-(4-fluorophenyl)ethyl]-1H-pyrimidin-4-one.

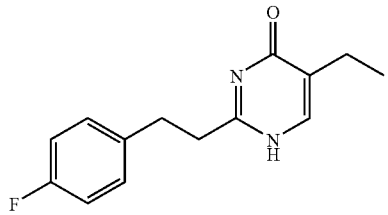

Sodium (0.23 g) in dry ethanol (10 ml) was treated with 3-(4-fluorophenyl) propionamidine hydrochloride (Int. A108) (1.02 g). Ethyl 2-formylbutyrate (0.72 g) was added and the mixture refluxed for 6 h then maintained at room temperature for a further 24 h. The reaction mixture was concentrated in vacuo, and the residue treated with water and acidified with conc. hydrochloric acid. The white precipitate was filtered off, washed with water and dried in vacuo at 40° C. overnight, to give the title compound, (982 mgs, 80%) $^1$H-NMR (CDCl$_3$) δ 1.22 (3H, t), 2.52 (2H, q), 2.94 (2H, m), 3.09 (2H, m), 6.96 (2H, m), 7.24 (2H, m), 7.84 (1H, s) and 13.06 (1H, br. s), (APCI+) Found (M+1)=247, $C_{14}H_{15}FN_2O$ requires 246.

| No. | Precursors | Name |
|---|---|---|
| B41 | A110<br>Methyl 2-formylpropionate | 2-(2-phenylethyl)-5-methyl-1H-pyrimidin-4-one |
| B42 | A112<br>Ethyl 2-formylbutyrate | 5-ethyl-2-[3-(4-fluorophenyl)propyl]-1H-pyrimidin-4-one |
| B43 | A108<br>Ethyl 4,4,4-Trifluoro-2-formylbutyrate | 2-[2-(4-fluorophenyl)ethyl]-5-(2,2,2-trifluoroethyl)-1H-pyrimidin-4-one |
| B44 | A108<br>Ethyl 2-acetylpropionate | 5,6-dimethyl-2-[2-(4-fluorophenyl)ethyl]-1H-pyrimidin-4-one |

Intermediate B50—2-(2-[2-(2,3-Difluorophenyl)-ethyl]-4-oxo-4,5,6,7-tetrahydro-cyclopentapyrimidin-1-yl)-acetic acid ethyl ester

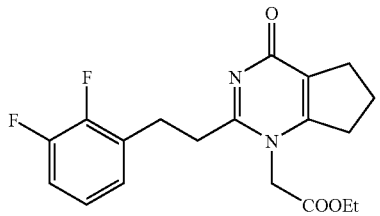

A mixture of Intermediate B1 (2.76 g, 10.0 mmol), ethyl iodoacetate (3.55 ml, 30.0 mmol) and N,N-diisopropylethylamine (5.22 ml, 30.0 mmol) in dichloromethane (40 ml) was stirred at 30° C. for 3 days. Further ethyl iodoacetate (3.55 ml, 30.0 mmol) and N,N-diisopropylethylamine (5.22 ml, 30.0 mmol), was added, the mixture stirred for 10 days and then washed with water, dried (MgSO$_4$) and evaporated. The residue was purified by chromatography (silica, ethyl acetate/acetone) to give the title compound as a brown solid (0.67 g, 19%). $^1$H-NMR (DMSO) δ 1.21 (3H, t), 1.96 (2H, m), 2.59 (2H, t), 2.83–3.01 (4H, m), 3.04 (2H, t), 4.20 (2H, q), 4.92 (2H, s), 7.10–7.30 (3H, m); MS (APCI+) found (M+1)=363; C$_{19}$H$_{20}$F$_2$N$_2$O$_3$ requires 362.

Intermediate B51—t-Butyl 2-(5-ethyl-2-(2-4-fluorophenyl)ethyl)-4-oxo-4H-pyrimidin-1-yl)-acetate

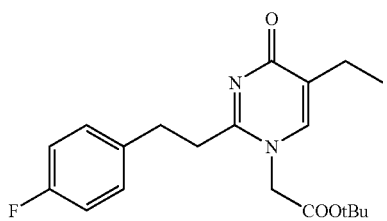

5-Ethyl-2-[2-(4-fluorophenyl)ethyl]-1H-pyrimidin-4-one (B40) (955 mgs) in dichloromethane (20 mls) was treated with t-butyl iodoacetate, (2.82 g) and diisopropylethylamine (2.03 mls) at room temperature for 3 days. The solution was washed with saturated sodium bicarbonate, brine and dried over anhydrous magnesium sulphate. The solution was concentrated to give a semi-solid which was triturated with ether:dichloromethane, 5:1, giving the title compound as a white solid, (1.101 g, 79%), $^1$H-NMR (CDCl$_3$) δ 1.16 (3H, t), 1.47 (9H, s), 2.47 (2H, q), 2.74 (2H, t), 3.14 (2H, t), 4.27 (2H, s), 6.90 (1H, s), 6.98 (2H, m) and 7.17 (2H, m). (APCI+) Found (M+1)=361, C$_{20}$H$_{25}$FN$_2$O$_3$ requires 360.

Intermediate B52—Ethyl (2,4-dioxo-4H-pyrido[2,3-d][1,3]oxazin-1-yl)acetate

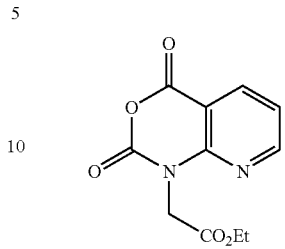

A 2:1 mixture of 3- and 6-azaisatoic anhydride (3.55 g, 21.6 mmol) (*Synthesis* 1982, 11, 972) was added portionwise to a suspension of sodium hydride (0.95 g, 60% in oil, 23.8 mmol) in DMF (40 ml). After stirring for 1 h, ethyl bromoacetate (2.64 ml, 23.8 mmol) was added. The reaction mixture was stirred overnight. The solvent was removed under reduced pressure. Ice/water was added to the residue and stirred for 1 h. The resulting pink solid was collected by filtration, washed with water and dried under vacuum at 40° C. The product was a 4:1 mixture of the [2,3-d] and the [3,2-d]isomers. $^1$H-NMR (d$_6$-DMSO) δ 1.21 (3H, t), 4.18 (2H, q), 4.92 (2H, s), 7.45 (1H, dd), 8.47 (1H, dd), 8.77 (1H, dd); MS (APCI+) found (M+1)=251; C$_{11}$H$_{10}$N$_2$O$_5$ requires 250.

Intermediate B53—Ethyl 2-(2-(2,3-difluorophenyl)ethyl-4-oxo-4H-pyrido[2,3-d]pyrimidin-1-yl)acetate

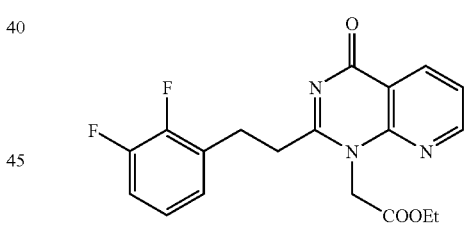

Intermediate B52 (as a 4:1 mixture of the [2,3-d] and the [3,2-d]isomers) (1.0 g, 3.99 mmol) and 3-(2,3-difluorophenyl)propionamidine hydrochloride (Int. A3) (1.0 g, 4.53mmol) were added to pyridine (25 ml) and heated under reflux for 16 h. The solvent was evaporated under reduced pressure. The residue was partitioned between dichloromethane and water and then filtered through a celite pad. The organic layer was separated, washed with water, dried (MgSO$_4$), filtered and concentrated. Purification by chromatography (silica gel, EtOAc) gave the title compound (0.885 g, 59%) as an orange gum. $^1$H-NMR (CDCl$_3$) δ 1.29 (3H, t), 3.05 (2H, t), 3.31 (2H, t), 4.26 (2H, q), 5.22 (2H, s), 7.01–7.09 (3H, m), 7.45 (1H, dd), 8.64 (1H, dd), 8.70 (1H, dd); MS (APCI+) found (M+1)=374; C$_{19}$H$_{17}$F$_2$N$_3$O$_3$ requires 373.

Intermediate B55—Ethyl 2-(2,4-dioxo-4H-thieno[3,2-d][1,3]oxazin-1-yl)acetate.

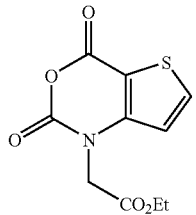

Sodium hydride (851 mg, 60% dispersion in oil) in dry N,N-dimethylformamide (DMF) (15 ml) was cooled under argon in an ice bath. A solution of 1H-thieno[3,2-d][1,3]oxazine-2,4-dione (3 g) in DMF (10 ml) was added over ca 20 min. The reaction mixture was stirred for 30 min at room temperature, then recooled in an ice bath. Ethyl iodoacetate (4.55 g) was added and the mixture stirred at room temperature for ca 2 h. The solution was concentrated to about half volume and cooled in an ice bath. Water was added (ca 200 ml). After 10 min the precipitate was filtered off and washed with water and hexane and dried at 40° C. in vacuo overnight. The title compound was obtained as a white solid (3.62 g, 80%). $^1$H-NMR (CDCl$_3$) δ 1.30 (3H, t), 4.28 (2H, q), 4.71 (2H, s), 6.77 (1H, d), 7.87 (1H, d). (APCI+) Found (M+1)=256, $C_{10}H_9NO_5S$ requires 255.

Intermediate B56—Ethyl 2-((2-Carbamoylthiophen-3-yl)-(3-(2,3-difluorophenyl)propanoyl)-amino)acetate.

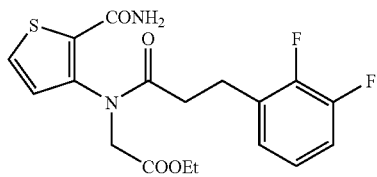

Ethyl 2-(2,4-dioxo-4H-thieno[3,2-d][1,3]oxazin-1-yl)acetate (B55) (1 g) in (THF) (20 ml) was cooled in an ice bath and treated with 0.880 aqueous ammonia (20 ml) for 30 min then stirred at room temperature for a further 30 min. The ThF was removed in vacuo and the aqueous solution treated with ethyl acetate and acidified with 5M hydrochloric acid. The aqueous solution was extracted with ethyl acetate. The combined organic phases were washed with brine, dried and concentrated to a solid. The crude amide as a suspension in dichloromethane (10 ml) was treated with diisopropylethylamine (0.82 ml) followed by a solution of 3-(2,3-difluorophenyl)propionoyl chloride (Int. A54) in dichloromethane (20 ml). After 1 h at room temperature, the dichloromethane was removed and replaced with ethyl acetate. The solution was washed with saturated sodium bicarbonate, brine and then dried and concentrated. After purification on a silica chromatography column eluting with 50% ethyl acetate/hexane, the title compound was obtained as a colourless solid (518 mgs, 33%); $^1$H-NMR (CDCl$_3$) δ 1.31 (3H, t), 2.46 (1H, m), 2.64 (1H, m), 2.95 (2H, t), 3.90 (1H, d), 4.24 (2H, m), 4.77 (1H, d), 5.69 (1H, br. s), 6.74 (1H, d), 6.86 (1H, m), 6.96 (2H, m), 7.52 (1H, d) and 8.60 (1H, br. s). (APCI+) Found (M+1)=397, $C_{18}H_{18}F_2N_2O_4S$ requires 396.

Intermediate B57—Ethyl 2-(2-(2-(2,3-Difluorophenyl)ethyl)-4-oxo-4H-thieno[3,2-d]pyrimidin-1-yl)acetate.

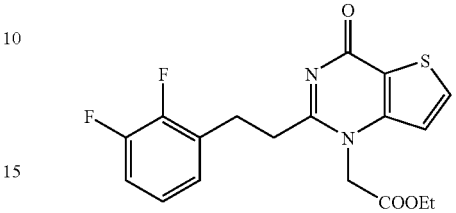

Ethyl 2-((2-carbamoylthiophen-3-yl)-(3-(2,3-difluorophenyl)propanoyl)anino)acetate (Int. B56) (500 mg) in dry DMF (3 ml) was cooled in an ice bath and treated portion wise with sodium hydride (50mg, 60% dispersion in oil). The reaction mixture was stirred at room temperature for 30 min to give an orange homogeneous solution. Excess IM hydrogen chloride in ether was added giving a pale yellow solution and a precipitate. The mixture was heated in an oil bath at 120° C. for 30 min. The solution was concentrated and re-dissolved in ethyl acetate. The solution was washed with saturated sodium bicarbonate, brine, dried and concentrated in vacuo to give a solid. Trituration with ether afforded the title compound as a white solid (375 mgs, 78%); $^1$H-NMR (CDCl$_3$) δ 1.29 (3H, t), 3.01 (2H, t), 3.30 (2H, t), 4.29 (2H, q), 4.84 (2H, s), 6.96 (1H, d), 7.03, (3H, m) and 7.77 (1H, d). (APCI+) Found (M+1)=379, $C_{18}H_{16}F_2N_2O_3S$ requires 378.

Intermediate B58—3-(3-(2,3-Difluorophenyl)-propanoylamino)-1-methyl-1H-pyrazole-4-carboxylic acid amide

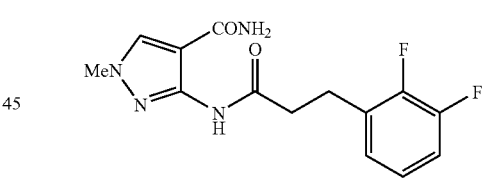

To a solution of 3-(2,3-difluorophenyl)-propionic acid (Int. A1) (6.83 g, 36.69 mmol) in anhydrous dichloromethane (50 ml) containing a few drops of DMF was added oxalyl chloride (6.4 ml, 73.38 mmol) at 0° C. under argon. The solution was then stirred at ambient temperature for 2 h and the solvent removed in vacuo. The residue was dissolved in dichloromethane (20 ml) and added to a slurry of 3-amino-1-methyl-1H-4-carboxylic acid amide (4.4 g, 23.66 mmol) (Patent to Ciba Ltd., GB 884851) in dichloromethane (30 ml) and pyridine (30 ml) at 0° C. under argon. The mixture was stirred at room temperature for 3 h, the solvent evaporated in vacuo and the solid residue washed aqueous sodium bicarbonate, water and dried in vacuo to yield the title compound (4.0 g, 55%) as a cream solid. $^1$H-NMR (DMSO) δ 2.56–3.00 (4H, m), 3.76 (3H, s), 7.08–7.28 (5H, m), 8.06 (1H, s), 9.92 (1H, s); MS (APCI+) found (M+1)=309; $C_{14}H_{14}F_2N_4O_2$ requires 308.

Intermediate B59—2-((4-Carbamoyl-1-methyl-1H-pyrazol-3-yl)-(3-(2,3-difluorophenyl) -propanoyl)-amino)-acetic acid ethyl ester

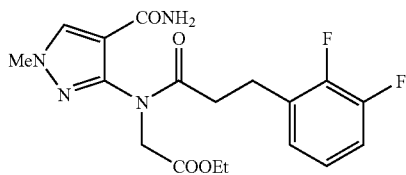

To a suspension of sodium hydride (60% dispersion in mineral oil, 260 mg, 6.5 mmol) in anhydrous DMF (5 ml) under argon at 0° C. was added a solution of 3-[3-(2,3-difluorophenyl)-propanoylamino]-1-methyl-1H-pyrazole-4-carboxylic acid amide (Int. B58) (2.0 g, 6.49mmol) in anhydrous DMF (5 ml). The reaction mixture was allowed to warm to room temperature over 30 min and then ethyl iodoacetate (0.15 ml, 1.27 mmol) was added at 0° C. The mixture was stirred at ambient temperature overnight, washed with brine, dried (MgSO$_4$) and evaporated. The residue was purified by flash chromatography (fine silica, dichloromethane-methanol) to give the title compound as a cream solid (1.4 g, 55%). $^1$H-NMR (DMSO) δ 1.18 (3H, t), 2.41 (2H, t), 2.87 (2H, t), 3.82 (3H, s), 4.10 (2H, q), 4.26 (2H, s), 6.99–7.24 (4H, m), 7.55 (1H, s), 8.16 (1H, s); MS (APCI+) found (M+1)=395; $C_{18}H_{20}F_2N_4O_4$ requires 394.

Intermediate B60—2-(4-(3-2,3-Difluorophenyl)-propanoyl-carbamoyl)-1-methyl-1H-pyrazol-3-ylamino)-acetic acid ethyl ester

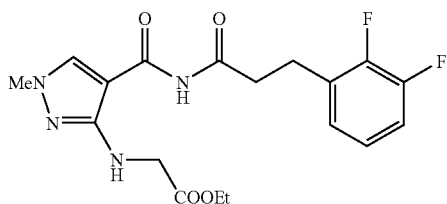

To a solution of 2-((4-carbamoyl-1-methyl-1H-pyrazol-3-yl)-[3-(2,3-difluorophenyl)-propanoyl]-amino)-acetic acid ethyl ester (Int. B59) (1.3 g, 3.3 mmol) in anhydrous DMF (12 ml) under argon was added sodium hydride (60% dispersion in mineral oil, 132 mg, 3.3 mmol) in one portion. The reaction mixture was stirred for 1 h at ambient temperature and then poured into saturated ammonium chloride solution and extracted with ethyl acetate. The combined extracts were washed with water, dried (MgSO$_4$) and evaporated to give the title compound as a cream solid (1.2 g, 92%). $^1$H-NMR (DMSO) δ 1.18 (3H, t), 2.95 (2H, t), 3.08 (2H, t), 3.63 (3H, s), 3.95 (2H, d), 4.10 (2H, q), 6.33 (1H, t), 7.03–7.27 (3H, m), 8.23 (1H, s), 10.45 (1H, s); MS (APCI+) found (M+1)=395; $C_{18}H_{20}F_2N_4O_4$ requires 394.

Intermediate B61—2-(6(-(2-(2,3-Difluorophenyl)-ethyl)-2-methyl-4-oxo-2,4-dihydro-pyrazolo[3,4-d]pyrimidin-7-yl)-acetic acid ethyl ester

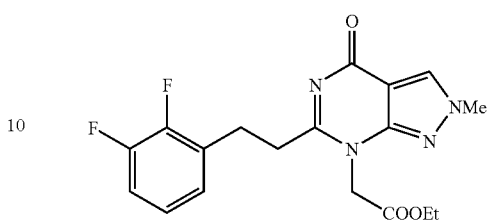

A suspension of p-toluenesulfonic acid monohydrate (200 mg) and 2-(4-(3-(2,3-difluorophenyl)-propanoylcarbamoyl)-1-methyl-1H-pyrazol-3-ylamino)-acetic acid ethyl ester (Int B60) (1.2 g, 3.04 mmol) in toluene (100 ml) was refluxed for 3 h. The mixture was cooled and dichloromethane (200 ml) was added. The resulting solution was washed with aqueous sodium bicarbonate solution, brine, dried (MgSO$_4$) and evaporated. The residue was purified by flash chromatography (silica, 5% methanol/dichloromethane) to give the title compound as a cream solid (650 mg, 57%). $^1$H-NMR (DMSO) δ 1.20 (3H, t), 2.94–3.09 (4H, m), 3.95 (3H, s), 4.18 (2H, q), 5.05 (2H, s), 7.11–7.29 (3H, m), 8.39 (1H, s); MS (APCI+) found (M+1)=377; $C_{18}H_{18}F_2N_4O_3$ requires 376.

Intermediate B65—Ethyl 2-(2-[2-(2,3-difluorophenyl)-ethyl]-4-oxo-4H-quinazolin-1-yl)-acetate

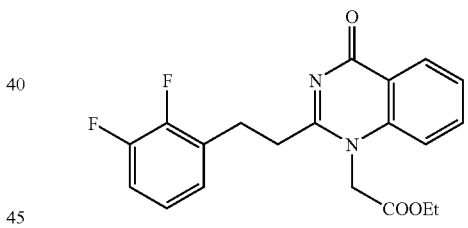

To a solution of 3-(2,3-difluorophenyl)-propionic acid (Int. A1) (5 g, 26.9 nmmol) in anhydrous dichloromethane (50 ml) containing a few drops of DMF was added oxalyl chloride (4.7 ml, 53.8 mmol) at 0° C. under argon. The solution was then stirred at ambient temperature for 2 h and the solvent removed in vacuo. The residue which contained the acid chloride (Int. A54) was dissoved in toluene (50 ml) and added to a slurry of (2-carbamoylphenylamino)-acetic acid ethyl ester (5.0 g, 22.5 mmol) in toluene (50 ml) containing pyridine (1 ml) and 4-dimethylaminopyridine (DMAP) (100 mg). After 16 h at 90° C. the solvent was evaporated and the solid residue washed with water, aqueous ammonia and ether to give the title compound (6.9 g, 82%) as a cream solid. $^1$H-NMR (DMSO) δ 1.24 (3H, t), 3.13 (2H, t), 3.34 (2H, m), 4.24 (2H, q), 5.48 (2H, s), 7.19 (1H, m), 7.29–7.35 (2H, m), 7.60–7.72 (2H, m), 7.94 (1H, t), 8.19 (1H, d); MS (APCI+) found (M+1)=373; $C_{20}H_{18}F_2N_2O_3$ requires 372.

Intermediate B66—5-Methyl-1-H-thieno[2,3-d][1,3]oxazine-2,4-dione

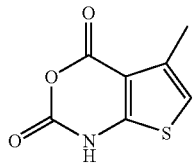

A mixture of ethyl 2-amino-4-methylthiophene-3-carboxylate (5 g, 0.03 mol) in methanol (25 ml) and aq. 2M sodium hydroxide (20.24 ml, 0.04 mol) was heated under reflux for 4 h. After cooling the solvents were evaporated, the residue dissolved in water (30 ml) and a 20% solution of phosgene in toluene (24 ml, 0.05 mol) added dropwise with ice cooling. After a further 30 miin the solid which had precipitated was filtered, washed with water then ether, and dried to give the tide compound 2.93 g (59%). $^1$H NMR (d$_6$-DMSO) δ 2.31 (3H, s), 6.78 (1H, s), 12.50 (1H, br. s).

Intermediate B67—2-(5-Methyl-2,4-dioxo-4H-thieno[2,3-d][1,3]oxazin-1-yl)-acetic Acid Ethyl Ester

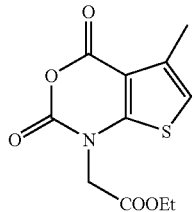

To a stirring suspension of sodium hydride (0.7 g, 17.6 mmol, 60% dispersion in oil) in dry DMF (30 ml) 5-methyl-1H-thieno[2,3-d][1,3]oxazine-2,4-dione (Int. B66) (2.93 g, 16 mmol) was added portionwise under argon. After 1 h, ethyl bromoacetate (1.95 ml, 17.6 mmol) was added dropwise with ice cooling. When addition was complete the reaction was allowed to warm to ambient temperature. After 16 h the solvent was evaporated and the residue treated with water. The precipitated solid was filtered, washed with water and dried, to give the title compound (4.18 g, 97%). $^1$H NMR (d6-DMSO) δ 1.22 (3H, t), 2.34 (3H, s), 4.15 (2H, q), 4.75 (2H, s), 6.95 (1H, s).

Intermediate B68—Ethyl 2-(2-[2-(4-Fluorophenyl)-ethyl]-4-oxo-4H-quinazolin-1-yl)-acetate

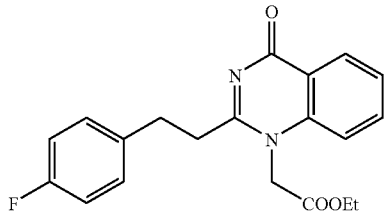

A solution of 3-(4-fluorophenyl)-propionamidine hydrochloride (Int. A108) (0.42 g, 2.05 mmol) and ethyl 2-(2,4-dioxo-4H-benzo[d][1,3]oxazin-1-yl)-acetate (0.51 g, 2.05 mmol) in pyridine (20ml) was heated at reflux for 16 h, allowed to cool then concentrated in vacuo. The residues were chromatographed over silica eluting with ethyl acetate to yield the product as a white solid (0.26 g, 36%). $^1$H-NMR (CDCl$_3$) δ 1.24 (3H, t,), 3.0 (2H, m), 3.17 (2H, m), 4.24 (2H, q), 5.29 (2H, s), 6.95 (2H, m), 7.2–7.3 (3H, m), 7,40 (1H, m), 7.67 (1H, m), 8.29 (1H, dd); MS (APCI+) found (M+1)= 355; $C_{20}H_{19}FN_2O_3$ requires 354.

Intermediate C1—2-(2-(2-(2,3-Difluorophenyl)-ethyl)-4-oxo-4,5,6,7-tetrahydro-cyclopenta-pyrimidin-1-yl)-acetic acid

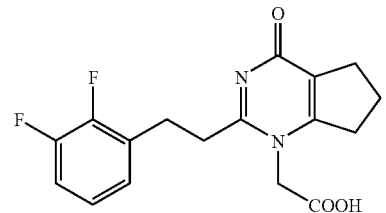

A solution of 2-2-[2-(2,3-difluorophenyl)-ethyl]-4-oxo-4,5,6,7-tetrahydro-cyclopentapyrimidin-1-yl)-acetic -yl)-acetic acid ethyl ester (B50) (0.66 g, 1.83 mmol), sodium hydroxide (0.15 g, 3.67 mmol) in methanol (6 ml) and water (2 ml) was stirred at ambient temperature overnight. The solvent was removed in vacuo and the residue dissolved in water (2 ml). Acidification to pH 1 with 2M hydrochloric acid gave a solid that was filtered, washed with water and dried in vacuo to give the desired product (0.50 g, 82%) as a cream solid. $^1$H-NMR (DMSO) δ 1.96 (2H, m), 2.63 (2H, t), 2.85–3.03 (6H, m), 4.91 (2H, s), 7.10–7.34 (3H, m); MS (APCI+) found (M+1)=335; $C_{17}H_{16}F_2N_2O_3$ requires 334.

Intermediate C2—2-(5-Ethyl-2-(2-(4-fluorophenyl)ethyl)-4-oxo-4H-pyrimidin-1-yl)acetic acid

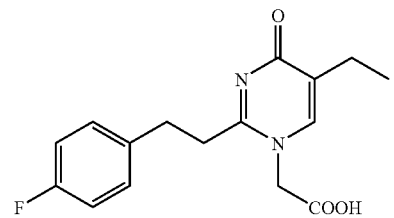

t-Butyl 2-(5-ethyl-2-[2-(4-fluorophenyl)ethyl]-4-oxo-4H-pyrimidin-1-yl)acetate (Int B51) (1 g) was dissolved in trifluoroacetic acid (10 ml) and stirred for 3 h at room temperature. The solution was concentrated under vacuum to a foam. Trituration with ether afforded the title compound as a colourless solid, (0.783 g, 93%), $^1$H-NMR (DMSO) δ 1.05 (3H, t, J=7.5 Hz), 2.24 (2H, q, J=7.5 Hz), 2.79 (2H, m), 2.93 (2H, m), 4.79 (2H, s), 7.11 (2H, m), 7.30 (2H, m), 7.53 (1H, s) and 13.48 (1H, br. s). (APCI−) Found (M−1)=303, $C_{16}H_{17}FN_2O_3$ requires 304.

The following 4-oxo-4H-pyrimidin-1-ylacetic acids were prepared from the corresponding 1H-pyrimidin-4-ones by alkylation with ethyl iodoacetate (as for Intermediate B50) followed by hydrolysis as for Intermediate C1, or by allylation with t-butyl iodoacetate (as for Intermediate B51) followed by hydrolysis as for Intermediate C2.

| No. | Precursor | Structure | Name |
|---|---|---|---|
| C3 | B2 | 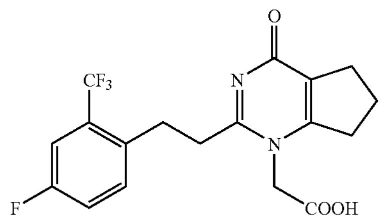 | 2-(2-(2-(2-trifluoromethyl-4-fluorophenyl)-ethyl)-4-oxo-4,5,6,7-tetrahydro-cyclopentapyrimidin-1-yl)-acetic acid |
| C4 | B3 | 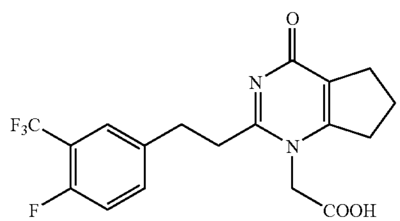 | 2-(2-(2-(3-trifluoromethyl-4-fluorophenyl)-ethyl)-4-oxo-4,5,6,7-tetrahydro-cyclopentapyrimidin-1-yl)-acetic acid |
| C5 | B4 | 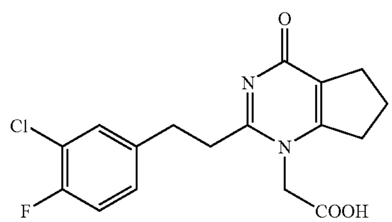 | 2-(2-(2-(3-chloro-4-fluorophenyl)-ethyl)-4-oxo-4,5,6,7-tetrahydro-cyclopentapyrimidin-1-yl)-acetic acid |
| C6 | B5 | 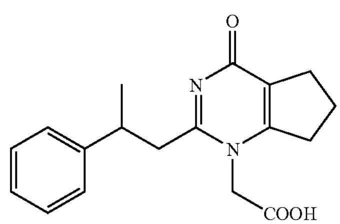 | (±)-2-(2-(2-phenyl-prop-1-yl)-4-oxo-4,5,6,7-tetrahydro-cyclopentapyrimidin-1-yl)-acetic acid |
| C7 | B6 | 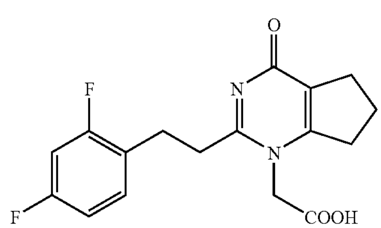 | 2-(2-(2-(2,4-difluorophenyl)-ethyl)-4-oxo-4,5,6,7-tetrahydro-cyclopentapyrimidin-1-yl)-acetic acid |
| C8 | B7 | 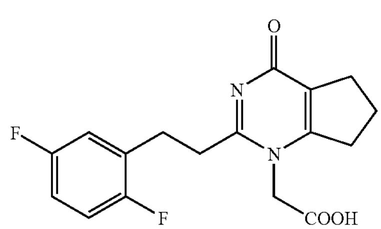 | 2-(2-(2-(2,5-difluorophenyl)-ethyl)-4-oxo-4,5,6,7-tetrahydro-cyclopentapyrimidin-1-yl)-acetic acid |
| C9 | B8 | 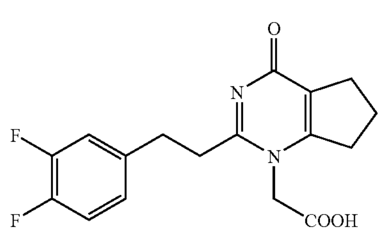 | 2-(2-(2-(3,4-difluorophenyl)-ethyl)-4-oxo-4,5,6,7-tetrahydro-cyclopentapyrimidin-1-yl)-acetic acid |

-continued

| No. | Precursor | Structure | Name |
|---|---|---|---|
| C10 | B9 | 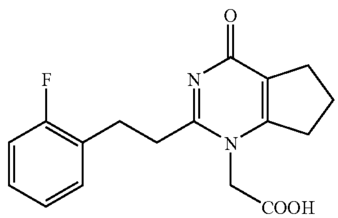 | 2-(2-(2-(2-fluorophenyl)-ethyl)-4-oxo-4,5,6,7-tetrahydro-cyclopentapyrimidin-1-yl)-acetic acid |
| C11 | B10 | 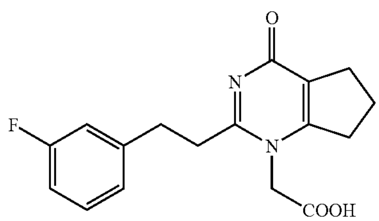 | 2-(2-(2-(3-fluorophenyl)-ethyl)-4-oxo-4,5,6,7-tetrahydro-cyclopentapyrimidin-1-yl)-acetic acid |
| C12 | B11 | 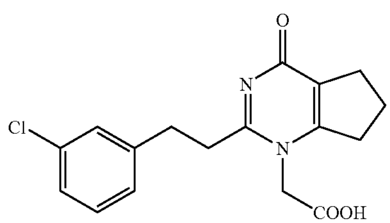 | 2-(2-(2-(3-chlorophenyl)-ethyl)-4-oxo-4,5,6,7-tetrahydro-cyclopentapyrimidin-1-yl)-acetic acid |
| C13 | B12 | 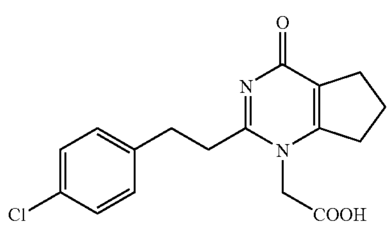 | 2-(2-(2-(4-chlorophenyl)-ethyl)-4-oxo-4,5,6,7-tetrahydro-cyclopentapyrimidin-1-yl)-acetic acid |
| C14 | B13 | 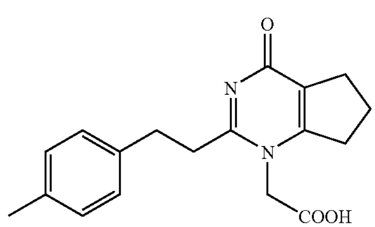 | 2-(2-(2-(4-methylphenyl)-ethyl)-4-oxo-4,5,6,7-tetrahydro-cyclopentapyrimidin-1-yl)-acetic acid |
| C15 | B14 | 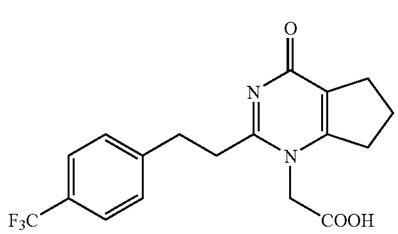 | 2-(2-(2-(4-(trifluoromethyl)phenyl)-ethyl)-4-oxo-4,5,6,7-tetrahydro-cyclopentapyrimidin-1-yl)-acetic acid |

-continued

| No. | Precursor | Structure | Name |
|---|---|---|---|
| C16 | B15 | 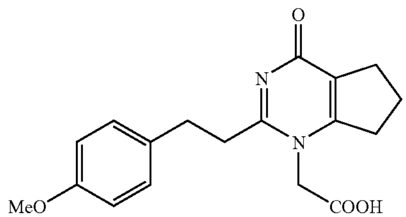 | 2-(2-(2-(4-methoxyphenyl)-ethyl)-4-oxo-4,5,6,7-tetrahydro-cyclopentapyrimidin-1-yl)-acetic acid |
| C17 | B16 | 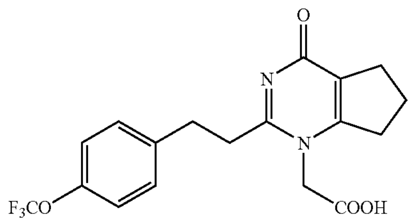 | 2-(2-(2-(4-(trifluoromethoxy)phenyl)-ethyl)-4-oxo-4,5,6,7-tetrahydro-cyclopentapyrimidin-1-yl)-acetic acid |
| C18 | B17 | 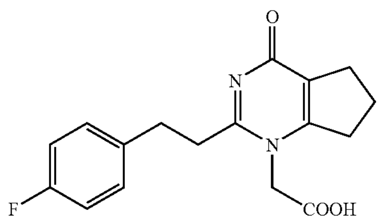 | 2-(2-(2-(4-fluorophenyl)-ethyl)-4-oxo-4,5,6,7-tetrahydro-cyclopentapyrimidin-1-yl)-acetic acid |
| C19 | B18 | 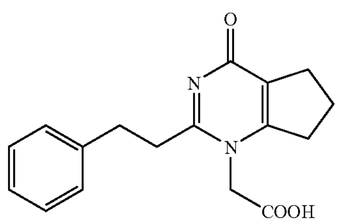 | 2-(2-(2-phenyl-ethyl)-4-oxo-4,5,6,7-tetrahydro-cyclopentapyrimidin-1-yl)-acetic acid |
| C20 | B19 | 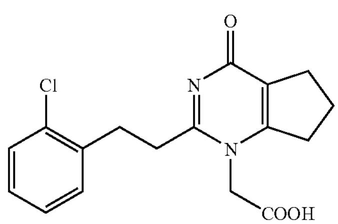 | 2-(2-(2-(2-chlorophenyl)-ethyl)-4-oxo-4,5,6,7-tetrahydro-cyclopentapyrimidin-1-yl)-acetic acid |
| C21 | B20 | 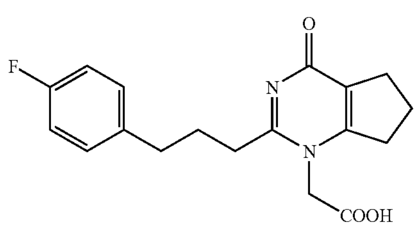 | 2-(2-(3-(4-fluorophenyl)-propyl)-4-oxo-4,5,6,7-tetrahydro-cyclopentapyrimidin-1-yl)-acetic acid |
| C22 | B21 | 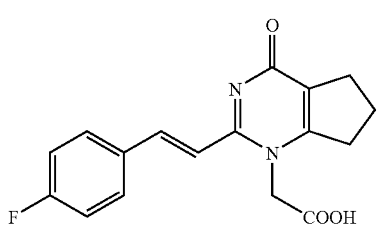 | (E)-2-(2-(2-(4-fluorophenyl)-vinyl)-4-oxo-4,5,6,7-tetrahydro-cyclopentapyrimidin-1-yl)-acetic acid |

| No. | Precursor | Structure | Name |
|---|---|---|---|
| C30 | B41 | 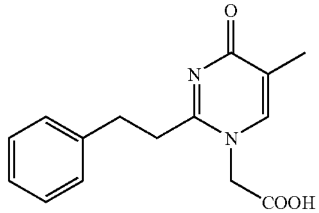 | 2-(2-(2-phenylethyl)-5-methyl-4-oxo-4H-pyrimidin-1-yl)acetic acid |
| C31 | B42 | 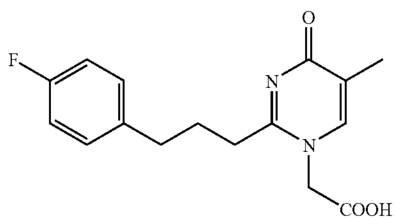 | 2-(5-ethyl-2-(3-(4-fluorophenyl)propyl)-4-oxo-4H-pyrimidin-1-yl)acetic acid |
| C32 | B43 | 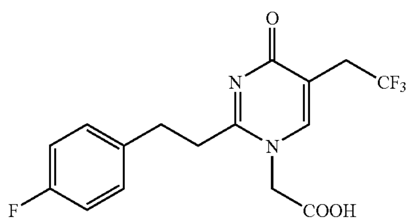 | 2-(2-(2-(4-fluorophenyl)ethyl)-5-(2,2,2-trifluoroethyl)-4-oxo-4H-pyrimidin-1-yl)acetic acid |
| C33 | B44 | 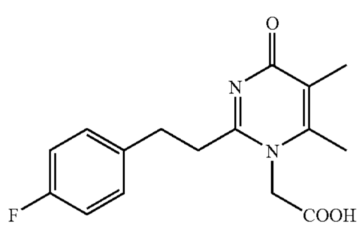 | 2-(4-fluorophenyl)ethyl)-5,6-dimethyl-4-oxo-4H-pyrimidin-1-yl)acetic acid |

Intermediate C35—2-(2-(2-(2,3-Difuorophenyl)ethyl-4-oxo-4H-pyrido[2,3-d]pyrimidin-1-yl)acetic acid

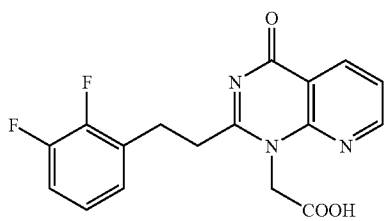

Example B53 (0.86 g, 2.3mmol) was dissolved in EtOH (10 ml). Water (3 ml) and 2M NaOH (1.38 ml, 2.76 mmol) were added and the mixture was stirred for 15 min. The reaction mixture was concentrated, then water and EtOAc added. The pH was adjusted to 3.0 by the addition of 2M HCl. The resulting solid was collected by filtration, washed with water and EtOAc, and dried under vacuum to give 0.464 g of a 1.8:1 mixture of the title compound and (3-arbamoylpyridin-2-ylamino) acetic acid. $^1$H-NMR data of the title compound. $^1$H-NMR (d$_6$-DMSO) δ 3.16 (4H, s), 5.25 (2H, s), 7.13–7.17 (1H, m), 7.24–7.30 (2H, m), 7.59 (1H, dd), 8.47 (1H, dd), 8.84 (1H, dd); MS (APCI$^-$) found (M-H$_3$O)$^-$=326; C$_{17}$H$_{13}$NF$_2$N$_3$O$_5$ requires 345.

The following intermediates were prepared from Intermediate B52 and the arnidines stated by the method of Intermediate B53 to give acetic acid derivatives after hydrolysis as for Intermediates C35 or C1.

| No. | Precursors | Structure | Name |
|---|---|---|---|
| C36 | B52 + A108 | 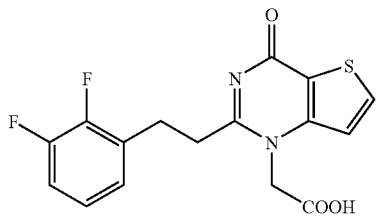 | 2-(2-(4-Fluorophenyl)ethyl-4-oxo-4H-pyrido[2,3-d]pyrimidin-1-yl)acetic acid |
| C37 | B52 + A113 | 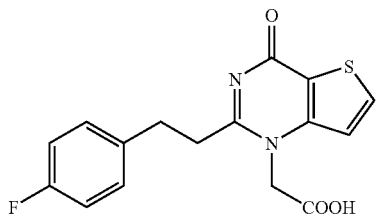 | 2-(2-(2,3,4-Trifluorophenyl)ethyl-4-oxo-4H-pyrido[2,3-d]pyrimidin-1-yl)acetic acid |

Intermediate C39—{2-[2-(2,3-Difluorophenyl)ethyl]-4-oxo-4H-thieno[3,2-d]pyrimidin-1y}acetic acid.

Ethyl 2-(2-[2-(2,3-difluoropbenyl)ethyl]-4-oxo-4H-thieno[3,2-d]pyrimidin-1-yl) acetate (Int B57) (375 mg) as a suspension in dioxan (2–3 ml) was treated with 0.5M solution of aqueous sodium hydroxide (1.98 ml) at room temperature. After 1 h the solution was concentrated to a small volume and acidified with 2M hydrochloric acid. The precipitate was filtered off, washed with water and dried in vacuo at 40° C. overnight. The title compound was obtained as a white solid (308 mgs, 89%); $^1$H-NMR (DMSO) δ 3.09 (4H, m), 5.19 (2H, s), 7.05–7.31 (3H, m), 7.49 (1H, d, J5.2 Hz) and 8.14 (1H, d, J5.2 Hz). (APCI+) Found (M+1)=351, $C_{16}H_{12}F_2N_2O_3S$ requires 350.

Intermediate C40—2-(2-[2-(4-Fluorophenyl)ethyl]-4-oxo-4H-thien [3,2-d]pyrimidin-1-yl)acetic acid.

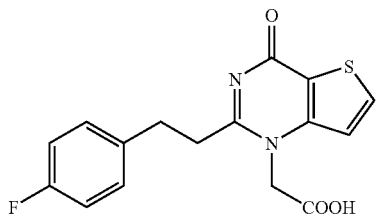

The above acetic acid derivative was prepared from Intermediates B55 and A108 by the procedures for Intermediates B56, B57 and C39.

Intermediate C41—(6-(2-(2,3-Difluorophenyl)-ethyl)-2-methyl-oxo-2,4-dihydro-pyrazolo-[3,4-d]pyrimidin-7-yl)-acetic acid

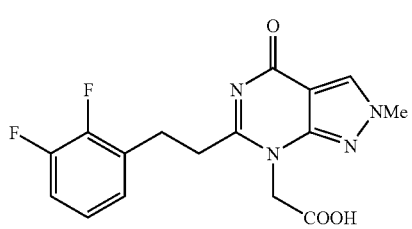

A solution of 2-(6-[2-(2,3-difluorophenyl)-ethyl]-2-methyl-4-oxo-2,4-dihydro-pyrazolo[3,4-d]pyrimidin-7-yl)-acetic acid ethyl ester (Int. B61) (600 mg, 1.6 mmol) in methanol (15 ml) and 2M sodium hydroxide solution (1.0 ml, 2 mmol) was stirred at ambient temperature overnight. The solvent was removed in vacuo and the residue dissolved in water (3 ml). Acidification to pH 1 with 2M hydrochloric acid gave a solid that was filtered, washed with water and dried in vacuo to give the title compound as a cream solid (0.54 g, 97%). $^1$H-NMR (DMSO) δ 2.83 (2H, t), 3.31 (2H, t), 4.06 (3H, s), 5.24 (2H, s), 6.99–7.36 (3H, m), 8.80 (1H, s).

Intermediate C43—2-(2-(2-(2,3-Difluorophenyl)-ethyl)-4-oxo-4H-uinazolin-1-yl)-acetic acid

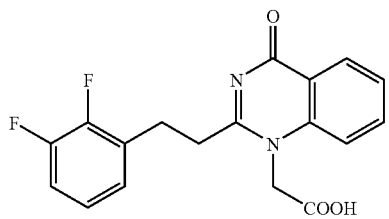

A solution of 2-(2-(2-(2,3-difluorophenyl)-ethyl)-4-oxo-4H-quinazolin-1-yl)-acetic acid ethyl ester (B65) (6.8 g, 18.3 mmol) in methanol (30 ml) and 2M sodium hydroxide solution (18.0 ml, 36 mmol) was stirred at ambient temperature overnight. The solvent was removed in vacuo and the residue dissolved in water (10 ml). Acidification to pH 1 with 2M hydrochloric acid gave a solid that was filtered, washed with water and dried in vacuo to give the desired product (5.9 g, 94%) as a white solid. $^1$H-NMR (DMSO) δ 3.11–3.30 (4H, m), 5.31 (2H, s), 7.16–7.33 (3H, m), 7.61 (1H, t), 7.68 (1H, d), 7.89 (1H, t), 8.18 (1H, d); MS (APCI+) found (M+1)=345; $C_{18}H_{14}F_2N_2O_3$ requires 344.

The following 4-oxo-4H-quinazolin-1-yl-acetic acids (C44-C68) were prepared from acid chlorides and (2-carbamoylphenylamino)-acetic acid ethyl ester (or simple substituted derivatives prepared by the general method of Monatsh. Chem. 1986, 117(4), 499–509) in a two step procedure by the methods used for Intermediates B65 and C43.

| No. | Precursors | Structure | Name |
|-----|-----------|-----------|------|
| C44 | A8 | 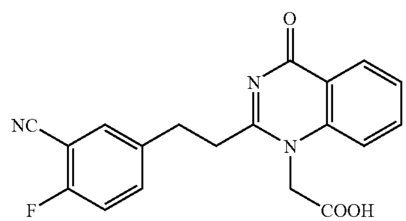 | 2-(2-(2-(3-Cyano-4-fluorophenyl)-ethyl)-4-oxo-4H-quinazolin-1-yl)-acetic acid |
| C45 | A51 | 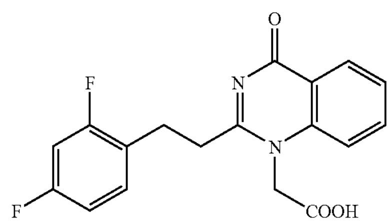 | 2-(2-(2-(2,4-Difluorophenyl)-ethyl)-4-oxo-4H-quinazolin-1-yl)-acetic acid |
| C46 | A52 | 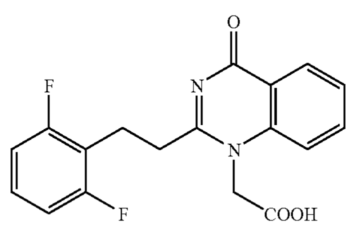 | 2-(2-(2-(2,6-Difluorophenyl)-ethyl)-4-oxo-4H-quinazolin-1-yl)-acetic acid |
| C47 | A53 | 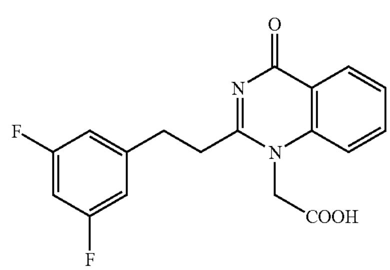 | 2-(2-(2-(3,5-Difluorophenyl)-ethyl)-4-oxo-4H-quinazolin-1-yl)-acetic acid |
| C48 | A55 | 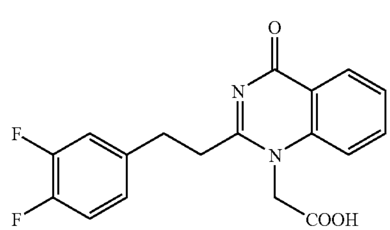 | 2-(2-(2-(3,4-Difluorophenyl)-ethyl)-4-oxo-4H-quinazolin-1-yl)-acetic acid |

| No. | Precursors | Structure | Name |
|---|---|---|---|
| C49 | A56 | 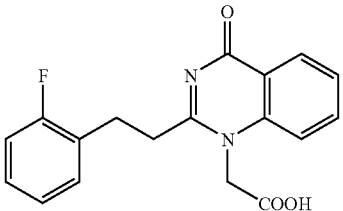 | 2-(2-(2-(2-Fluorophenyl)-ethyl)-4-oxo-4H-quinazolin-1-yl)-acetic acid |
| C50 | A57 | 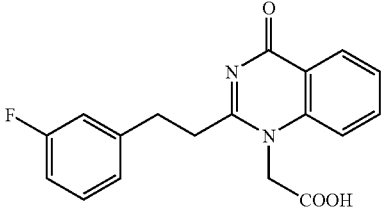 | 2-(2-(2-(3-Fluorophenyl)-ethyl)-4-oxo-4H-quinazolin-1-yl)-acetic acid |
| C52 | A59 | 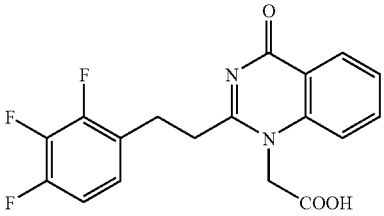 | 2-(2-(2-(2,3,4-Trifluorophenyl)-ethyl)-4-oxo-4H-quinazolin-1-yl)-acetic acid |
| C53 | A60 | 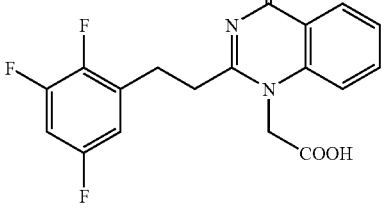 | 2-(2-(2-(2,3,5-Trifluorophenyl)-ethyl)-4-oxo-4H-quinazolin-1-yl)-acetic acid |
| C54 | A61 | 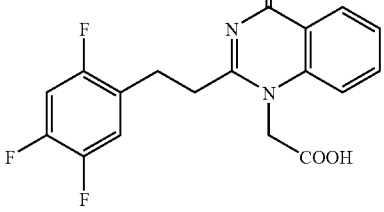 | 2-(2-(2-(2,4,5-Trifluorophenyl)-ethyl)-4-oxo-4H-quinazolin-1-yl)-acetic acid |
| C55 | A62 | 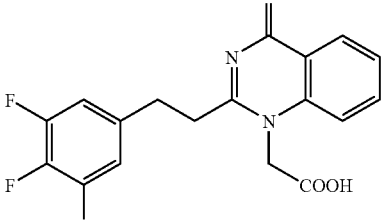 | 2-(2-(2-(3,4,5-Trifluorophenyl)-ethyl)-4-oxo-4H-quinazolin-1-yl)-acetic acid |

| No. | Precursors | Structure | Name |
|-----|------------|-----------|------|
| C56 | A63 | 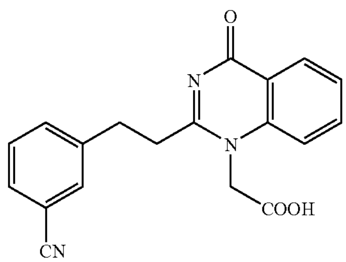 | 2-(2-(2-(3-Cyanophenyl)-ethyl)-4-oxo-4H-quinazolin-1-yl)-acetic acid |
| C57 | A64 | 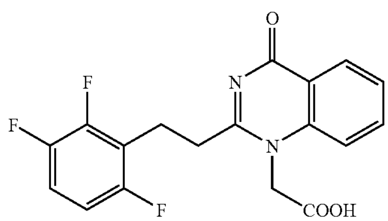 | 2-(2-(2-(2,3,6-Trifluorophenyl)-ethyl)-4-oxo-4H-quinazolin-1-yl)-acetic acid |
| C58 | A65 | 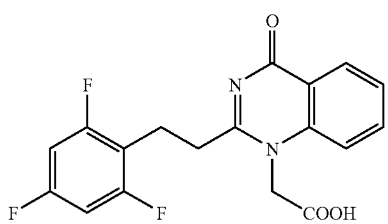 | 2-(2-(2-(2,4,6-Trifluorophenyl)-ethyl)-4-oxo-4H-quinazolin-1-yl)-acetic acid |
| C59 | A66 | 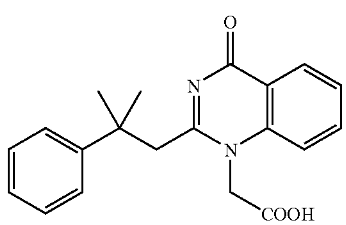 | 2-(2-(2-methyl-2-phenyl-propyl)-4-oxo-4H-quinazolin-1-yl)-acetic acid |
| C60 | A67 | 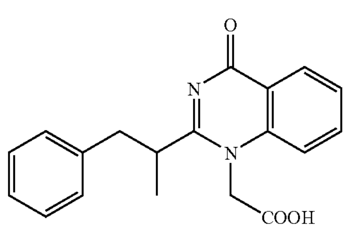 | (+/−)-2-(2-(1-methyl-2-phenyl-ethyl)-4-oxo-4H-quinazolin-1-yl)-acetic acid |
| C61 | A59 | 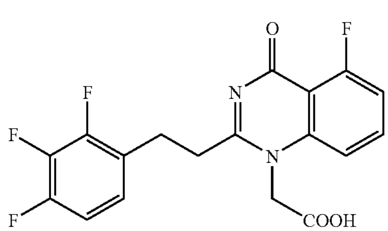 | 2-(5-Fluoro-2-(2-(2,3,4-trifluorophenyl)-ethyl)-4-oxo-4H-quinazolin-1-yl)-acetic acid |

| No. | Precursors | Structure | Name |
|---|---|---|---|
| C62 | A59 | 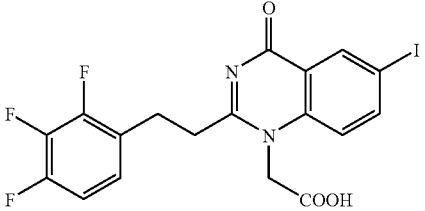 | 2-(6-Fluoro-2-(2-(2,3,4-trifluorophenyl)-ethyl)-4-oxo-4H-quinazolin-1-yl)-acetic acid |
| C63 | A59 | 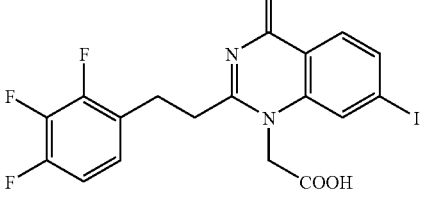 | 2-(7-Fluoro-2-(2-(2,3,4-trifluorophenyl)-ethyl)-4-oxo-4H-quinazolin-1-yl)-acetic acid |
| C64 | A54 | 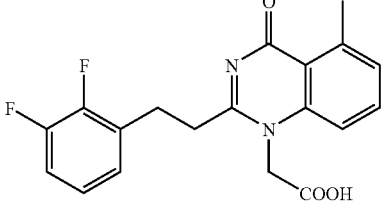 | 2-(2-(2-(2,3-Difluorophenyl)-ethyl)-5-methyl-4-oxo-4H-quinazolin-1-yl)-acetic acid |
| C65 | A54 | 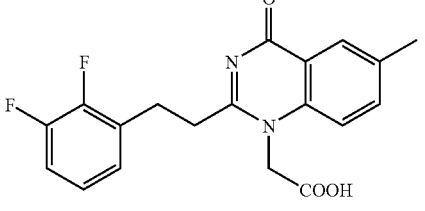 | 2-(2-(2-(2,3-Difluorophenyl)-ethyl)-6-methyl-4-oxo-4H-quinazolin-1-yl)-acetic acid |
| C66 | A54 | 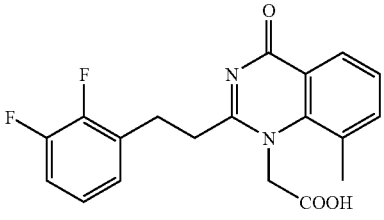 | 2-(2-(2-(2,3-Difluorophenyl)-ethyl)-8-methyl-4-oxo-4H-quinazolin-1-yl)-acetic acid |
| C67 | A54 | 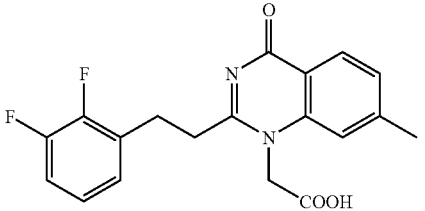 | 2-(2-(2-(2,3-Difluorophenyl)-ethyl)-7-(trifluoromethyl)-4-oxo-4H-quinazolin-1-yl)-acetic acid |

-continued

| No. | Precursors | Structure | Name |
|---|---|---|---|
| C68 | 3-Phenyl-propionyl chloride | 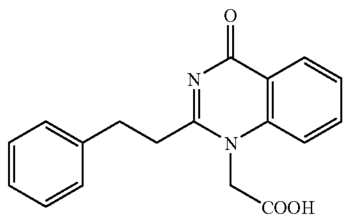 | 2-(2-(2-phenyl-ethyl)-4-oxo-4H-quinazolin-1-yl)-acetic acid |
| C75 | A54 | 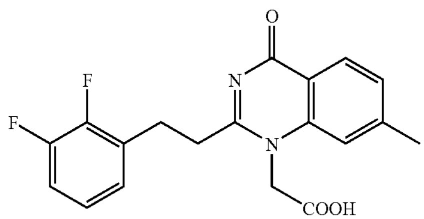 | 2-(2-(2-(2,3-difluorophenyl)-ethyl)-7-methyl-4-oxo-4H-quinazolin-1-yl)-acetic acid |
| C76 | A54 | 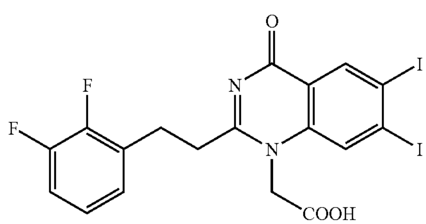 | 2-(2-(2-(2,3-difluorophenyl)-ethyl)-6,7-difluoro-4-oxo-4H-quinazolin-1-yl)acetic acid |
| C77 | A54 | 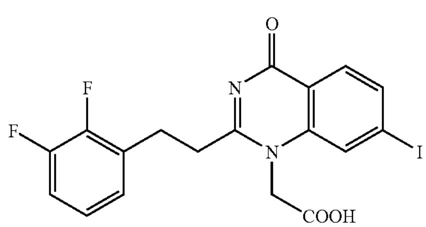 | 2-(2-(2-(2,3-difluorophenyl)-ethyl)-7-fluoro-4-oxo-4H-quinazolin-1-yl)acetic acid |
| C78 | A54 | 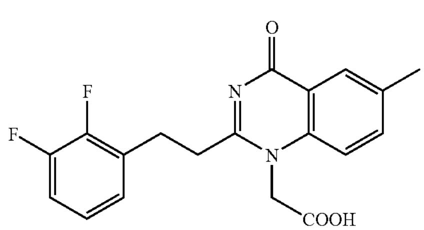 | 2-(2-(2-(2,3-difluorophenyl)-ethyl)-6-fluoro-4-oxo-4H-quinazolin-1-yl)acetic acid |

Intermediate C69—2-(2-[2-(4-Fluorophenyl)-ethyl]-4-oxo-4H-quinazolin-1-yl)-acetic Acid

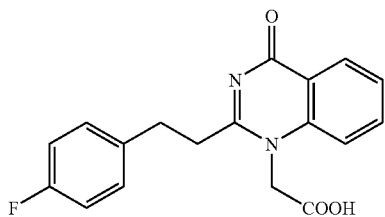

Ethyl 2-(2-[2-(4-fluorophenyl)-ethyl]-4-oxo-4H-quinazolin-1-yl)-acetate (Intermediate B68) was hydrolysed using the method for Example C1 to give the title compound.

The following acetic acid intermediates were prepared using the general procedures of Examples B68 and C1.

A mixture of 3-amino-pyridine-2-carboxylic acid amide (300 mg, 2.2 mmol), ethyl bromoacetate (0.24 ml, 2.2 mmol) and sodium hydrogen carbonate (185 mg, 2.2 mmol) in DMF (2 ml) was heated at 70° C. for 4 h. The mixture was evaporated to dryness and partitioned between water and dichloromethane. The aqueous layer was extracted with dichloromethane and the combined organic phases washed with brine, dried (MgSO$_4$) and evaporated. The residue was purified by chromatography (10 g silica cartridge, dichloromethane-50% ethyl acetate/dichloromethane) to give the title compound as a white solid. This material was converted to the title compound in a two step procedure by the methods of Intermediates B65 and C43. $^1$H-NMR (d6 DMSO) δ 3.13 (4H, brs), 5.20 (2H, s), 7.12–7.32 (3H, m), 7.83 (1H, dd), 8.13 (1H, d), 8.80 (1H, d), 13.70 (1H, brs); MS (APCI−) found (M−1)=344; $C_{17}H_{13}F_2N_3O_3$ requires 345.

| No. | Precursors | Structure | Name |
|---|---|---|---|
| C70 | A95 | (structure) | 2-(2-(2-phenyl-propyl)-4-oxo-4H-quinazolin-1-yl)-acetic acid |
| C71 | A98 | (structure) | 2-(2-(2-(2,5-difluorophenyl)-ethyl)-4-oxo-4H-quinazolin-1-yl)-acetic acid |
| C72 | B67, A108 | (structure) | 2-(2-(2-(4-fluorophenyl)-ethyl)-5-methyl-4-oxo-4H-thieno[2,3-d]pyimidin-1-yl)-acetic acid |

Intermediate C80—2-(2-(2-(2,3-Difluorophenyl)-ethyl)-4-oxo-4H-pyrido[3,2-d]pyrimidin-1-yl)acetic acid

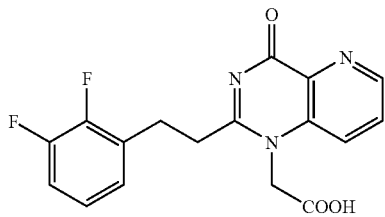

Intermediate D1—4-(4-Chlorophenyl)benzaldehyde

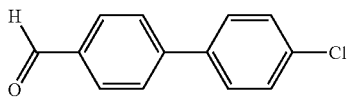

(a) A mixture of 4-formylbenzeneboronic acid (2.50 g, 2 equiv), 4-chloroiodobenzene (1.98 g, 1 equiv), tetrakis(triphenylphosphine)palladium(0) (0.50 g, 0.05 equiv), aqueous sodium carbonate (18 ml, 2M solution, 2 equiv) and dimethoxyethane (50 ml) was stirred at reflux under argon overnight, then cooled and diluted with ethyl acetate. The-mixture was filtered as necessary to remove inorganic residues, then the organic layer was washed successively with aqueous citric acid and brine, dried and evaporated. The crude product was purified by chromatography (silica, 5% ethyl acetate in hexane); product fractions were evaporated to a white solid (1.32 g, 72%).

(b) A mixture of 4-chlorobenzeneboronic acid (19.4 g, 1 equiv), 4bromobenzaldehyde (22.9 g, 1 equiv), palladium (II) acetate (1.4 g, 0.05 equiv), aqueous sodium carbonate (30.3 g in 144 ml solution, 2 equiv) and dimethoxyethane (500 ml) was stirred at reflux under argon for 2.5 h, then evaporated to low volume and diluted with dichloromethane. Workup continued as in (a) above to give identical material (25.2 g, 94%). $^1$H-NMR (CDCl$_3$) δ 10.05 (1H, s), 7.96 (2H, d), 7.73 (2H, d), 7.57 (2H, d), 7.46 (2H, d); MS (AP+) found (M+1)=217, C$_{13}$H$_9$ClO requires 216.

Intermediate D2—4(4-Trifluoromethylphenyl)-benzaldehyde

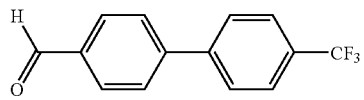

A 3 L 3-neck flask fitted with top stirrer, condenser and argon inlet/outlet was charged with 4-trifluoromethybenzene boronic acid (90.0 g, 0.474 mol), 4-bromobenzaldehyde (83.29 g, 0.450 mol) and 1,2-dimethoxyethane (1.3 L), followed by 2M aqueous sodium carbonate (474 ml) and palladium acetate (5.32 g, 0.0237 mol). The stirring mixture was heated to reflux for 4 h under argon, then allowed to cool to room temperature over 16 h. The reaction mixture was filtered through hyflo. The filtrate was diluted with saturated brine and extracted 3× with ethyl acetate. The combined extracts were dried over magnesium sulfate and filtered through hyflo, giving a clear orange filtrate which was evaporated to a solid (ca. 120 g, crude). Flash chromatography (silica, 10–50% dichloromethane in pet. ether, 10% steps) gave a white solid which dissolved in hexane (500 ml) on boiling. Crystallisation, finally in ice, gave the title compound as a solid which was filtered off, washed with ice cold hexane and dried, (86.33 g, 77%). $^1$H-NMR (CDCl$_3$) δ 7.77–8.03 (8H, m), 10.09 (1H, s).

Intermediate D3—N-(2-Diethylaminoethyl)-4-(4-chlorophenyl)benzylamine

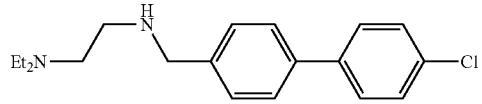

A mixture of Intermediate D1 (55.0 g), N,N-thethylethylenediamine (35.6 ml), 4A molecular sieve (37 g), and dichloromethane (1100 ml) was reacted at room temperature under argon for 16 h, with occasional agitation. The solid was filtered off and washed with dichloromethane, and the combined filtrates evaporated to a yellow foam (72.4 g). This intermediate imine was reduced with sodium borohydride (8.7 g) in ethanol (850 ml) as described for Intermediate D4, yielding the title compound as a yellow oil (72.7g). $^1$H-NMR (CDCl$_3$) δ 1.70 (2H, t), 2.22 (6H, s), 2.33 (2H, t), 2.69 (2H, br. m), 3.83 (2H, s), 7.37–7.43 (4H, m), 7.52–7.56 (4H, m).

Intermediate D4—N,N-Diethyl-N'-(4'-trifluoromethylbiphenyl-4-ylmethyl)-ethane-1,2-diamine)

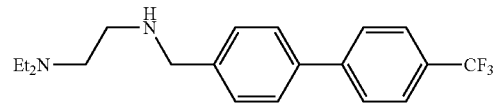

4-(4-Trifluoromethylphenyl)benzaldehyde (85.43g, 0.3414 mol) (Int. D2) and 4A molecular sieve (400g, pre-dried at 120° C.) were suspended in dichloromethane (1.4 L), then N,N-diethylethylenediamine (47.97 ml, 0.3414 mol) was added. The mixture was left at room temperature for 16 h with occasional shaking, then the sieves were filtered off and washed with dichloromethane. The combined filtrates were evaporated to a yellow solid and dried under high vacuum. This material (114.3 g, 0.328 mol) in ethanol (1 L) was cooled in an ice bath, and sodium borohydride (12.41 g, 0.328 mol) was added under argon with stirring. Hydrogen evolution was observed. After 30 min the ice bath was removed, and the cloudy yellow solution was left to stand at room temperature for 16 h. The solvent was removed in vacuo, water and brine were added, and the mixture was extracted 3× with dichloromethane. The combined extracts were dried over potassium carbonate and evaporated to give the title compound as a yellow solid, (112.1 g, 98%). $^1$H-NMR (CDCl$_3$) δ 7.66 (4H, s), 7.53–7.56 (2H, m), 7.40–7.44 (2H, m), 3.86 (2H, s), 2.47–2.75 (9H, m), 0.96–1.10 (6H, m); MS(APCI+) found (M+1)=351, C$_{20}$H$_{25}$F$_3$N$_2$ requires 350.

Intermediate D5—N-Methyl-4-(4-trifluoromethylphenyl) benzylamine

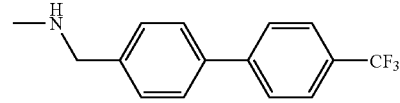

A mixture of Intermediate D2 (4.57 g, 1 eq), methylamine (9.15mL of a 2M solution in THF) and anhydrous magnesium sulphate (4.41 g, 2 eq) was stirred at room temperature for 16 h, filtered and the solid washed thoroughly with ethyl acetate. The combined filtrates were evaporated to a solid which was suspended in ethanol (90 mL) and sodium borohydride (1.01 g, 1.5 eq) added portionwise. The mixture stirred at room temperature for 3 h and the solvent removed in vacuo and the residue partitioned between dichloromethane and water. The organic layer was washed with brine, dried and evaporated to give the title compound as a white solid. $^1$H-NMR (CDCl$_3$) δ 7.68 (4H, m), 7.56–7.58 (2H, m), 7.43–7.45 (2H, m), 3.83 (2H, s), 2.50 (3H, s); MS(APCI+) found (M+1)=266, C$_{15}$H$_{14}$F$_3$N requires 265.

Intemediate D6—4-(4-Trifluoromethylphenyl)benzonitrile

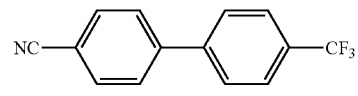

Prepared by the method of intermediate D2 using 4-trifluoromethylbenzeneboronic acid and 4-bromobenzonitrile. $^1$H-NMR (DMSO) δ 7.99–7.94 (6H, m) 7.86 (2H, d); MS(APCI+) found (M+1)=248, C$_{14}$H$_8$NF$_3$ requires 247.

Intemediate D7—4-(4-trifluoromethylphenyl)benzylamine, free base and hydrochloride salt

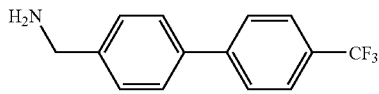

(a) A solution of intermediate D6 (75.5 g, 0.306 mol) in anhydrous THF (500 ml) was added dropwise to a solution of lithium aluminium hydride (460 ml, 1.0M solution in THF) at 0° C. under argon. The mixture was stirred at room temperature for 16 h, then water (17 ml), 10% aqueous sodium hydroxide solution (10 ml) and water (50 ml) were carefully added dropwise over 8 h under argon. The mixture was stirred for 16 h, then filtered through celite and the filtrate evaporated. The residue was dissolved in dichloromethane (500 ml) and washed with brine, dried and evaporated to give the title compound as a creamn solid (66.3g, 86%). $^1$H-NMR (CDCl$_3$) δ 7.68 (4H, s), 7.57 (2H, d), 7.42 (2H, d), 3.94 (2H, s), 1.50 (2H, s); MS(APCI+) found (M-NH$_2$)=235, C$_{14}$H$_{12}$F$_3$N requires 251.

(b) To a solution of intermediate D6 (96.7 g, 0.39 mol) in absolute ethanol (5 L) and concentrated hydrochloric acid (200 ml) was added 10% palladium on charcoal (30.0 g, 54% H$_2$O paste). The mixture was stirred under 50 psi hydrogen for 16 h. Additional 10% palladium on charcoal (25.0 g, 54% H$_2$O paste) was added and the mixture was stirred under 50 psi hydrogen for further 16 h. The mixture was filtered through celite and the solvent evaporated to give the hydrochloride salt of the title compound as a cream solid (102.5 g, 91%). $^1$H-NMR (DMSO) δ 8.61 (3H, s), 7.93 (2H, d), 7.83 (2H, d), 7.80 (2H, d), 7.65 (2H, d), 4.08 (2H, s); MS(APCI+) found (M-NH$_2$)=235, C$_{14}$H$_{12}$F$_3$N requires 251.

Intermediate D8—N-(1-Methyl-piperidin-4-yl)-4-(4-trifluoromethylphenyl)benzylamine

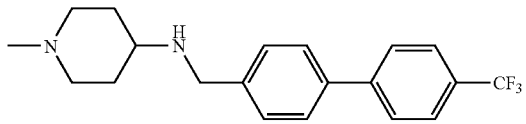

A mixture of intermediate D7 hydrochloride salt (6.0 g, 20.9rnmol), 1-methyl-piperidin-4-one (2.56 ml, 20.8 mmol), sodium triacetoxyborohyride (6.20 g, 29.3 mmol) and acetic acid (1.3 ml) in dichloroethane (50 ml) was stirred at room temperature under argon for 16 h then poured into 2M sodium hydroxide solution (150 ml). The organic phase was separated and the aqueous layer extracted with dichloromethane. The combined organic phases were washed with brine, dried and evaporated. Chromatography (silica, dichloromethane to 97:3 dichloromethane/methanolic ammonia) gave the product as a cream solid (6.3 g, 87%). $^1$H-NMR (CDCl$_3$) δ 7.68 (4H, s), 7.57 (2H, d), 7.42 (2H, d), 3.87 (2H, s), 2.82 (2H, m), 2.52 (1H, m), 2.27 (3H, s), 1.90–2.02 (4H, m), 1.45–1.51 (2H, m); MS(APCI+) found (M+1)=349, C$_{20}$H$_{23}$N$_2$F$_3$ requires 348.

Intermediate D9—4-(4-Bromophenyl)benzylaldehyde

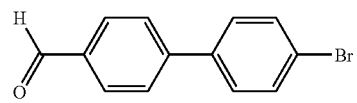

A solution of 4,4'-dibromobiphenyl (10 g, 32 mmol) in tetrahydrofuran (250 ml), was cooled to −78° C., and butyllithium (2.5M, 12.8 ml, 32 mmol) was added dropwise. After 15 min, dimethylformamide (50 ml) was added, initially dropwise. The mixture was allowed to warm to room temperature and stirred for 2 h, then water (250 ml) was added and the product was extracted into ether. Drying and evaporation of the extracts, followed by chromatography (silica, toluene) yielded the title compound (7.1 g, 85%). $^1$H-NMR (CDCl$_3$) δ 7.49 (2H, d), 7.60 (2H, d), 7.71 (2H, d), 7.95 (2H, d), 10.08 (1H, s).

Intermediate D10—4-(Thien-2-yl)benzyl acohol

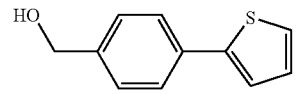

A mixture of 4-bromobenzyl alcohol (2.09 g, 11.2 mmol), 2-(tributylstannyl)thiophene (5.0 g, 13.4 mmol), tetrakis (trphenylphosphine)palladium (0.39 g, 0.34 mmol) and xylene (30 ml) was stirred at 140° C. for 1 h, then cooled and applied directly to a silica column. Elution with ethyl acetate/hexane gave the desired product (1.43 g, 67%). $^1$H-NMR (CDCl$_3$) δ 4.70 (2H, s), 7.07 (1H, m), 7.27 (1H, m), 7.30 (1H, m), 7.36 (2H, d), 7.60 (2H, d).

Intermediate D11—4-(5Tributylstannyl-thien-2-yl)benzyl acohol

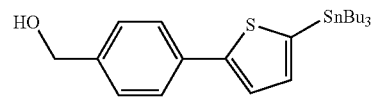

Intermediate D10 (1.43 g, 7.5 mmol) was dissolved in THF (40 ml) and cooled to −30° C. n-Butyllithium (16.5 mmol) was added dropwise and stirring continued at −30° C. for 1 h, then the mixture was cooled to −78° C. and a solution of tributyltin chloride (4.47 ml, 16.5 mmol) in THF (10 ml) was added. The mixture was allowed to warm to room temperature, then saturated aqueous ammonium chloride (15 ml) was added with stirring, followed by water (10 ml). The product was extracted into ether, dried, and the solvent evaporated. Chromatography (silica, 30% ethyl acetate in hexane) gave the desired product (3.29 g, 92%). $^1$H-NMR (CDCl$_3$) δ 0.90 (9H, t), 0.13 (6H, m), 0.37 (6H, m), 1.63 (6H, m), 4.70 (2H, d), 7.14 (1H, m), 7.36 (2H, m), 7.42 (1H, m), 7.62 (2H, m).

Intermediate D12—4-(Iodothien-2-yl)benzyl acohol

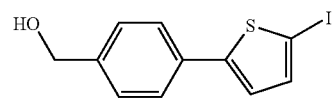

A solution of intermediate D11 (1.6 g, 3.34 mmol) in chloroform (40 ml) was cooled to 0° C. and a solution of iodine (0.805 g, 3.17mmol) in chloroform (10 ml) was added dropwise, followed by a solution of potassium fluoride (1.2 equiv) in methanol (4 ml). After stirring for 2 mins water was added, then the organic layer was separated and applied directly to a silica column, which was eluted with ethyl acetate/hexane to obtain the title compound (0.84 g, 80%). $^1$H-NMR (CDCl$_3$) δ 1.66 (1H, t), 4.70 (2H, d), 6.97 (1H, m), 7.21 (1H, m), 7.36 (2H, m), 7.51 (2H, m).

Intermediate D13—4-(5Iodothien-2-yl)benzaldehyde

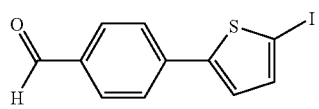

A mixture of intermediate D12 (0.40 g) and manganese dioxide (1.1 g, 10 equiv) in dichloromethane (20 ml) was stirred under argon in the dark for 16 h. Filtration through celite and evaporation of the solvent yielded the title compound (0.36 g). $^1$H-NMR (CDCl$_3$) δ 7.11 (1H, m), 7.26 (1H, m), 7.64 (2H, m), 7.89 (2H, m), 10.00 (1H, s).

Intermediate D14—4-(5-Trifluoromethylthien-2-yl)benzaldehyde

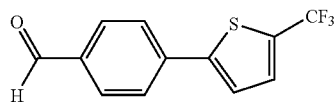

A mixture of intermediate D13 (0.772 g, 2.46 mmol), methyl 2,2-difluoro-2-(fluorosulfonyl)acetate (2.36 g, 12.3 mmol), copper iodide (0.56 g, 2.95 mmol), N-methylpyrrolidone (1.18 ml, 12.3 mmol) and dimethylformamide (20 ml) was stirred at 70° C. for 7 h, then further portions of methyl 2,2-difluoro-2-(fluorosulfonyl)acetate (2.36 g, 12.3 mmol) and copper iodide (2.8 g, 12.3 mmol) were added, and heating was continued for a further 6 h. Saturated aqueous ammonium chloride (30 ml) was added with stirring, then the mixtured was diluted with water (20 ml), filtered through celite, then extracted with ethyl acetate. The extracts were dried, evaporated, and purified by chromatography (silica, 15% ethyl acetate in hexane); yield 0.44 g (70%). $^1$H-NMR (CDCl$_3$) δ 7.39 (1H, m), 7.46 (1H, m), 7.77 (2H, m), 7.94 (2H, m), 10.06 (1H, s).

Intermediate D15—4-(4-Pentafluorophenyl)benzaldehyde

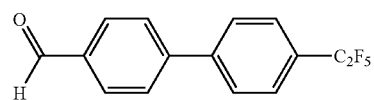

Pentafluoroethyl iodide (2 ml, 16.9 mmol) was added to copper (2.12 g, 33.3 mmol) and dimethylsulfoxide (13 ml) at 0° C. in a tube which was then sealed and heated to 110° C. for 4 h. A portion of the resulting organocuprate solution (3.2 ml) was mixed with intermediate D9 (0.20 g) and heated to 70° C. for 3 h. The remaining organocuprate was added, and heating continued for 20 h. The mixture was poured into a mixture of 2M hydrochloric acid and ethyl acetate, then the organic layer was dried and evaporated to obtain the title compound (0.22g). $^1$H-NMR (CDCl$_3$) δ 7.74 (6H, m), 7.97 (2H, m), 10.10 (1H, s).

The following intermediates were made as described in WO 00/66567

| No. | Structure | Name |
|---|---|---|
| D16 | 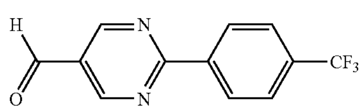 | (2-(4-trifluoromethylphenyl)pyrimidine-5-carboxaldehyde |
| D17 | 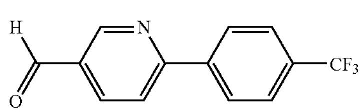 | 5-Formyl-2-(4-trifluoromethylphenyl)pyridine |
| D18 | 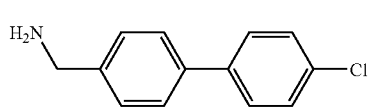 | 4-(4-Chlorophenyl)benzylamine |

5-(4-Chlorophenyl)furfural (Intermediate D19) was commercially available. The following intermediates were made by the method of Intermediate D1:

| No. | Precursors | Name |
|---|---|---|
| D21 | 4-bromobenzaldehyde, 4-n-pentylbenzeneboronic acid | 4-(4-n-pentylphenyl)benzaldehyde |
| D22 | 5-bromothiophene-2-carboxaldehyde 4-trifluoromethylbenzeneboronic acid | 5-(4-trifluoromethylphenyl)thiophene-2-carboxaldehyde |
| D23 | 4-bromobenzaldehyde 5-chlorothiophene-2-boronic acid | 4-(2-chlorothien-5-yl)benzylaldehyde |
| D24 | 4-bromobenzaldehyde, 4-methylbenzeneboronic acid | 4-(4-methylphenyl)benzaldehyde |
| D25 | 4-bromobenzaldehyde, 4-ethylbenzeneboronic acid | 4-(4-ethylphenyl)benzaldehyde |
| D26 | 4-bromobenzaldehyde, 4-methylthiobenzeneboronic acid | 4-(4-methylthiophenyl)benzaldehyde |
| D27 | 4-isopropyliodobenzene 4-formylbenzeneboronic acid | 4-(4-isopropylphenyl)benzaldehyde |
| D28 | 4-iodobenzonitrile 4-formylbenzeneboronic acid | 4-(4-cyanophenyl)benzaldehyde |
| D29 | 4-bromobenzaldehyde, 4-methylsulfonylbenzeneboronic acid | 4-(4-methylsulfonylphenyl)benzaldehyde |
| D30 | 5-bromo-2-furaldehyde 4-trifluoromethylbenzeneboronic acid | 5-(4-trifluoromethylphenyl)furfural |
| D31 | 5-bromothiophene-2-carboxaldehyde 5-chlorothiophene-2-boronic acid | 5-(5-chlorothien-2-yl)thiophene-2-carboxaldehyde |
| D91 | 1-iodo-4-(piperidin-1-ylsulfonyl)benzene 4-formylbenzeneboronic acid | 4-(piperidin-1-ylsulfonylphenyl)benzaldehyde |

The following intermediates were made by the method of Intermediate D3: Amine precursors were either commercially available, or readily prepared from commercially available materials by literature methods or minor modifications thereof.

| No. | Precursor | Structure | Name |
|---|---|---|---|
| D32 | Int. D2 | 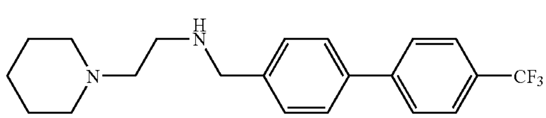 | N-(2-(piperidin-1-yl)ethyl)-4-(4-trifluoromethylphenyl)benzylamine |
| D33 | Int. D2 | 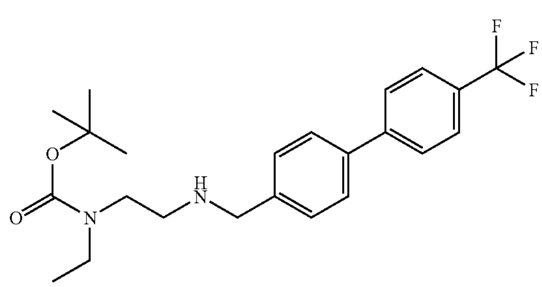 | N-(2-(N-ethyl-t-butoxycarbonylamino)-ethyl)-4-(4-trifluoromethylphenyl)benzylamine |
| D34 | Int. D2 | 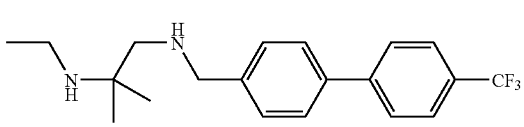 | N-(2-(ethylamino)-2-methyl-propyl)-4-(4-trifluoromethylphenyl)benzylamine |
| D35 | Int. D2 | 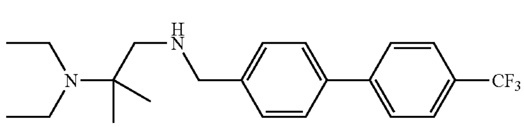 | N-(2-(diethylamino)-2-methyl-propyl)-4-(4-trifluoromethylphenyl)-benzylamine |

-continued

| No. | Precursor | Structure | Name |
|---|---|---|---|
| D36 | Int. D2 | 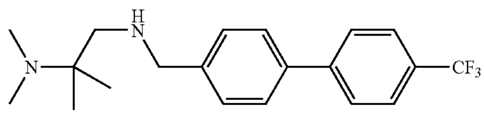 | N-(2-(dimethylamino)-2-methyl-propyl)-4-(4-trifluoromethylphenyl)benzylamine |
| D37 | Int. D2 | 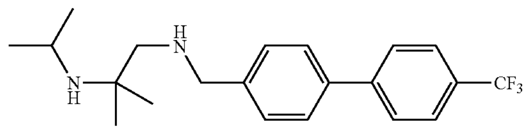 | N-(2-isopropylamino)-2-methyl-propyl)-4-(4-trifluoromethylphenyl)benzylamine |
| D38 | Int. D2 | 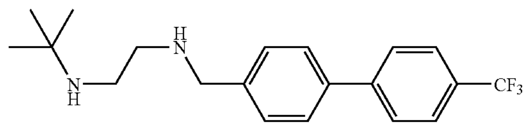 | N-(2-(t-butylamino)-ethyl)-4-(4-trifluoro-methylphenyl)benzylamine |
| D39 | Int. D2 | 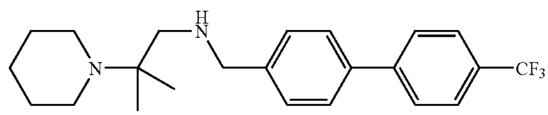 | N-(2-(piperidin-1-yl)-2-methyl-propyl)-4-(4-trifluoromethylphenyl)benzylamine |
| D40 | Int. D2 | 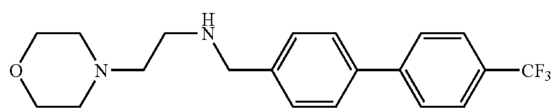 | N-(2-(morpholin-4-yl)ethyl)-4-(4-trifluoro-methylphenyl)benzylamine |
| D41 | Int. D2 | 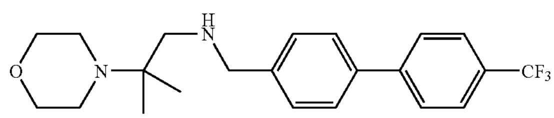 | N-(2-(morpholin-4-yl)-2-methyl-propyl)-4-(4-trifluoro-methylphenyl)benzylamine |
| D42 | Int. D2 | 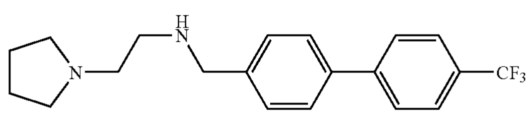 | N-(2-(pyrrolidin-1-yl)ethyl)-4-(4-trifluoro-methylphenyl)benzylamine |
| D43 | Int. D2 | 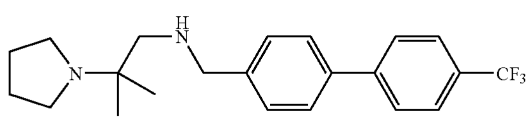 | N-(2-(pyrrolidin-1-yl)-2-methyl-propyl)-4-(4-trifluoromethylphenyl)benzylamine |
| D44 | Int. D2 | 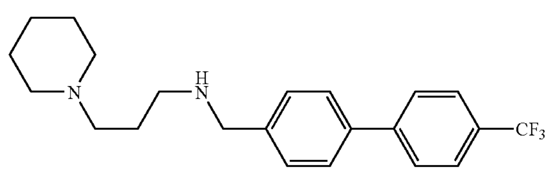 | N-(3-(piperidin-1-yl)-propyl)-4-(4-trifluoro-methylphenyl)benzylamine |
| D45 | Int. D2 | 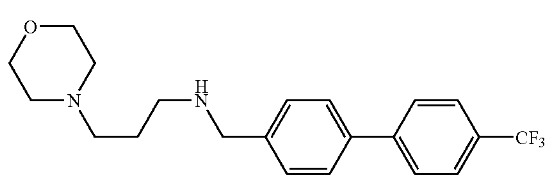 | N-(3-(morpholin-4-yl)-propyl)-4-(4-trifluoro-methylphenyl)benzylamine |
| D46 | Int. D2 | 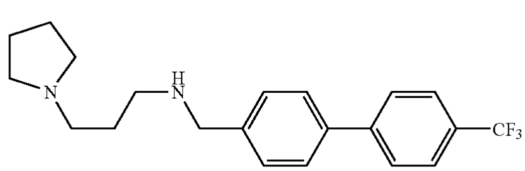 | N-(3-(pyrrolidin-1-yl)-propyl)-4-(4-trifluoro-methylphenyl)benzylamine |

-continued

| No. | Precursor | Structure | Name |
|---|---|---|---|
| D49 | Int. D2 | 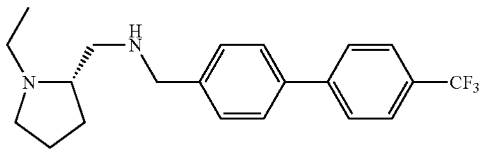 | (+/−)-N-(1-ethyl-pyrrolidin-2-ylmethyl)-4-(4-trifluoromethylphenyl)benzylamine |
| D50 | Int. D2 | 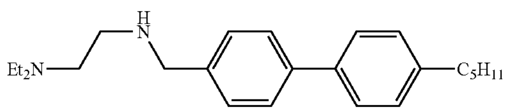 | N-(2-diethylaminoethyl)-4-(4-pent-1-ylphenyl)benzylamine |
| D51 | 4-biphenyl-carboxaldehyde | 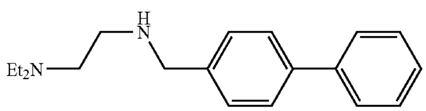 | N-(2-diethylaminoethyl)-4-(phenyl)benzylamine |
| D53 | Int. D2 | 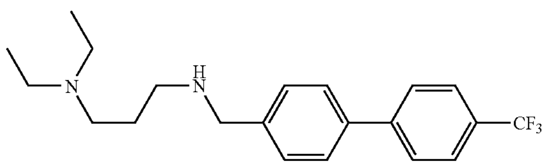 | N-(3-diethylamino-propyl)-4-(4-trifluoro-methylphenyl)benzylamine |
| D54 | Int. D2 | 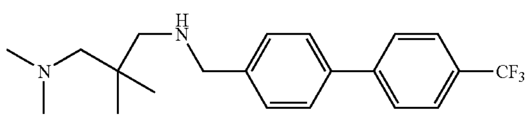 | N-(2,2-dimethyl-3-dimethylamino-propyl)-4-(4-trifluoromethylphenyl)benzylamine |
| D55 | Int. D2 | 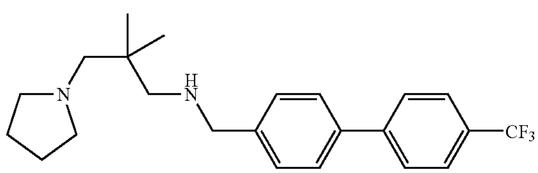 | N-(3-(pyrrolidin-1-yl)-2,2-dimethylpropyl)-4-(4-trifluoromethylphenyl)benzylamine |
| D56 | Int. D2 | 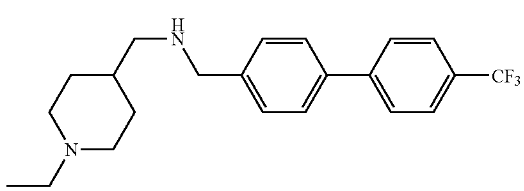 | N-(1-ethylpiperidin-4-ylmethyl)-4-(4-trifluoromethylphenyl)benzylamine |
| D57 | Int. D24 | 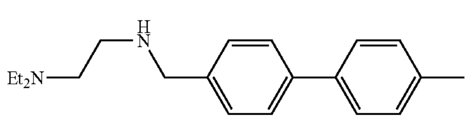 | N-(2-diethylaminoethyl)-4-(4-methylphenyl)-benzylamine |
| D58 | Int. D25 | 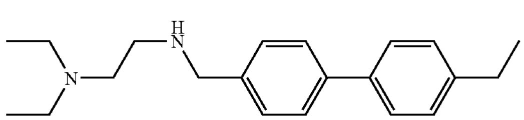 | N-(2-diethylaminoethyl)-4-(4-ethylphenyl)-benzylamine |
| D59 | Int. D26 | 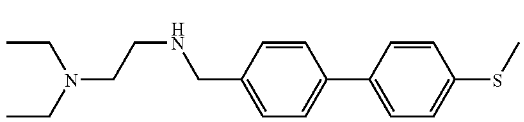 | N-(2-diethylaminoethyl)-4-(4-methylthio-phenyl)benzylamine |
| D60 | Int. D27 | 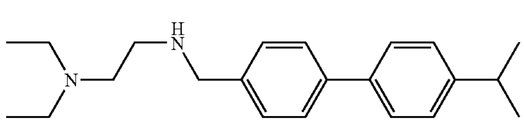 | N-(2-diethylaminoethyl)-4-(4-isopropyl-phenyl)benzylamine |

-continued

| No. | Precursor | Structure | Name |
|---|---|---|---|
| D61 | Int. D28 | 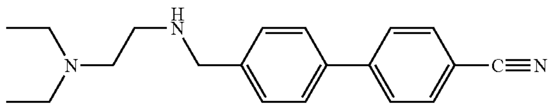 | N-(2-diethylaminoethyl)-4-(4-cyanophenyl)-benzylamine |
| D62 | Int. D29 | 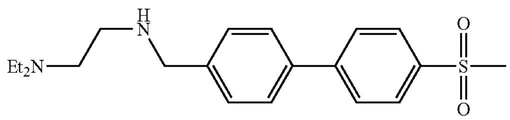 | N-(2-diethylaminoethyl)-4-(4-methylsulfonyl-phenyl)benzylamine |
| D63 | Int. D9 | 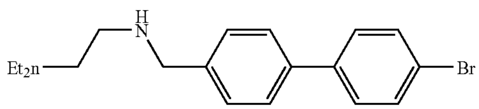 | N-(2-diethylaminoethyl)-4-(4-bromophenyl)-benzylamine |
| D64 | Int. D2 | 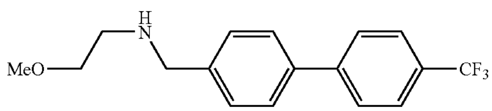 | N-(2-methoxyethyl)-4-(4-trifluoromethyl-phenyl)benzylamine |
| D65 | Int. D2 | 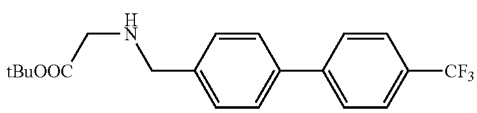 | N-(t-butoxycarbonylmethyl)-4-(4-trifluoro-methylphenyl)benzylamine |
| D66 | Int. D17 | 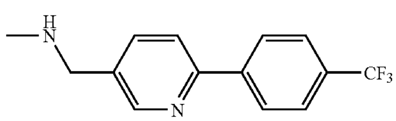 | N-methyl-2-(4-trifluoromethylphenylpyrid-5-ylmethylamine |
| D67 | Int. D16 | 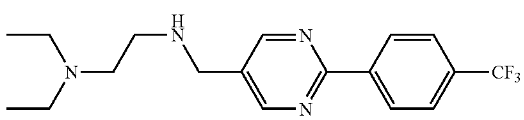 | N-(2-diethylaminoethyl)-(2-(4-trifluoro-methylphenyl)pyrimid-5-ylmethylamine |
| D68 | Int. D23 | 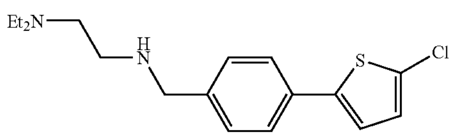 | N-(2-diethylaminoethyl)-4-(2-chlorothien-5-yl)benzylamine |
| D69 | Int. D22 | 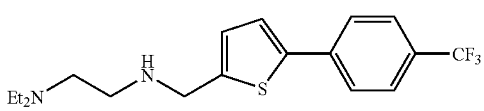 | N-(2-diethylaminoethyl)-5-(4-trifluoromethyl-phenyl)thien-2-ylmethylamine |
| D70 | Int. D14 | 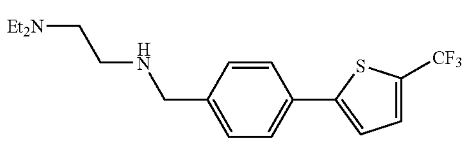 | N-(2-diethylaminoethyl)-4-(5-trifluoromethyl-thien-2-yl)benzylamine |
| D71 | Int. D17 | 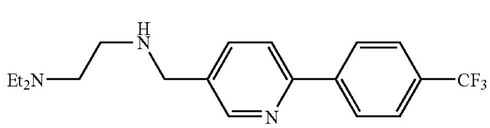 | N-(2-(diethylamino)ethyl)-2-(4-trifluoro-methylphenyl)pyrid-5-ylmethylamine |
| D72 | Int. D23 | 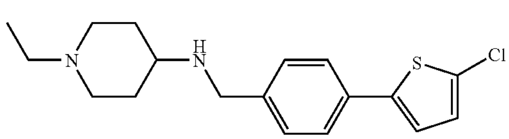 | N-(1-ethylpiperidin-4-yl)-4-(5-chlorothien-2-yl)benzylamine |

-continued

| No. | Precursor | Structure | Name |
|---|---|---|---|
| D73 | Int. D19 | 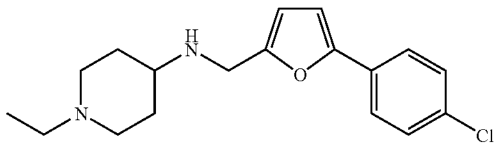 | N-(1-ethylpiperidin-4-yl)-5-(4-chlorophenyl)-fur-2-ylmethylamine |
| D74 | Int. D30 | 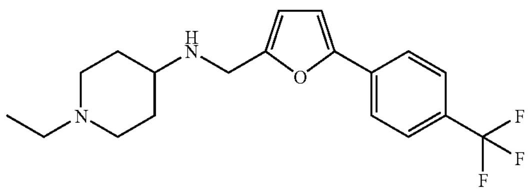 | N-(1-ethylpiperidin-4-yl)-5-(4-trifluoro-methylphenyl)fur-2-ylmethylamine |
| D75 | Int. D31 | 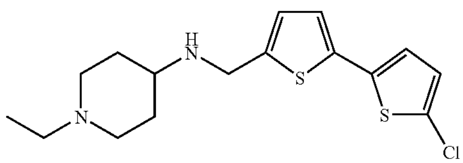 | N-(1-ethylpiperidin-4-yl)-2-(2-chlorothien-5-yl)thien-5-ylmethylamine |
| D76 | Int. D15 | 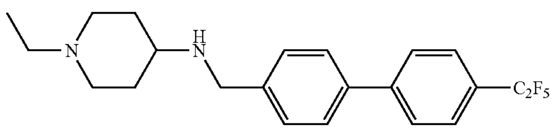 | N-(1-ethylpiperidin-4-yl)-(4-pentafluoro-ethylphenyl)benzylamine |
| D77 | Int. D22 | 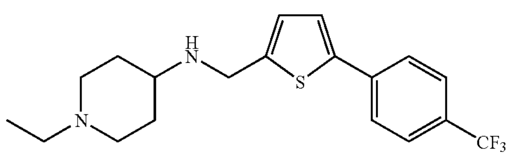 | N-(1-ethylpiperidin-4-yl)-5-(4-trifluoro-methylphenyl)thien-2-ylmethylamine |
| D78 | Int. D17 | 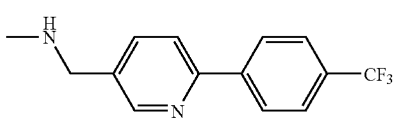 | N-methyl-2-(4-trifluoromethylphenyl)pyrid-5-ylmethylamine |
| D79 | Int. D14 | 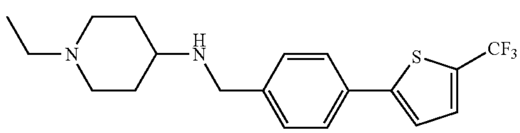 | N-(1-ethylpiperidin-4-yl)-4-(5-trifluoro-methylthien-2-yl)benzylamine |
| D95 | Int D2 | 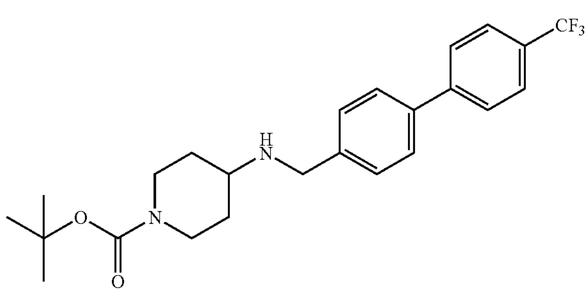 | N-(1-t-butoxycarbonylpiperidin-4-yl)-4-(4-trifluoromethylphenyl)benzylamine |
| D96 | Int D91 | 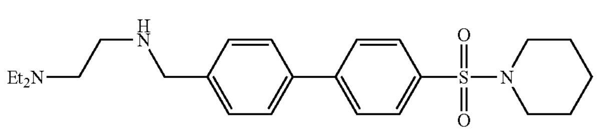 | N-(2-diethylaminoethyl)-4-(4-piperidin-1-ylsulfonylphenyl)benzylamine |

| No. | Precursor | Structure | Name |
|---|---|---|---|
| D97 | Int. D2 | 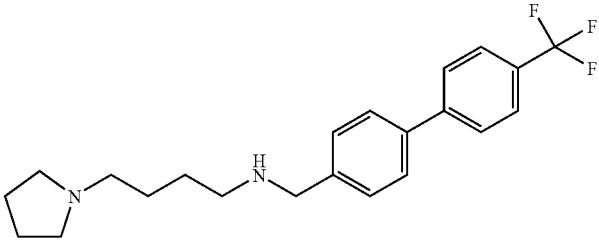 | N-(4-(pyrrolidin-1-yl)-butyl)-4-(4-trifluoromethylphenyl)benzylamine |

The following intermediates were made by the method of Intermediate D8: Piperidone precursors were either commercially available, or readily prepared from commercially available materials by literature methods or minor modifications thereof.

| D47 | Int. D2 | 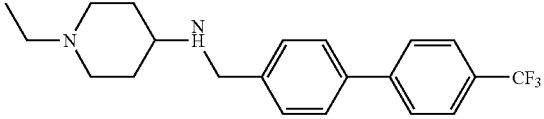 | N-(1-ethyl-piperidin-4-yl)-4-(4-trifluoromethylphenyl)benzylamine |
| D48 | Int. D2 | 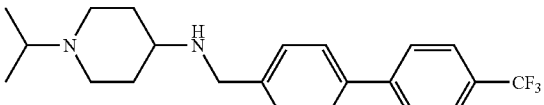 | N-(1-isopropyl-piperidin-4-yl)-4-(4-trifluoromethylphenyl)benzylamine |
| D80 | Int. D2 | 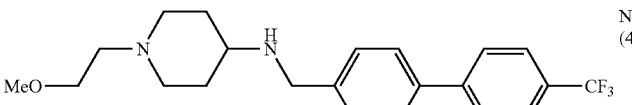 | N-(1-(2-methoxyethyl)piperidin-4-yl)-4-(4-trifluoromethylphenyl)benzylamine |
| D81 | Int. D2 | 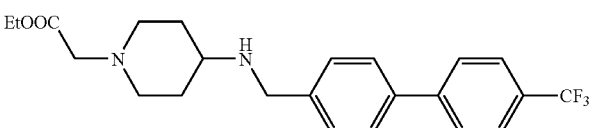 | N-(1-ethoxycarbonylmethylpiperidin-4-yl)-4-(4-trifluoromethylphenyl)-benzylamine |
| D82 | Int. D18 | 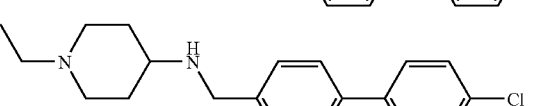 | N-(1-ethylpiperidin-4-yl)-4-(chlorophenyl)benzylamine |
| D83 | Int. D18 | 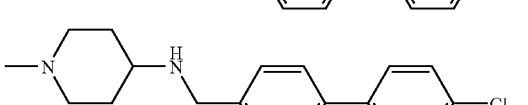 | N-(1-methylpiperidin-4-yl)-4-(4-chlorophenyl)benzylamine |
| D84 | Int. D18 | 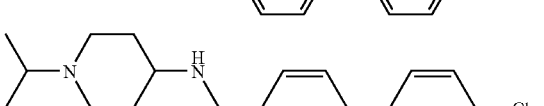 | N-(1-isopropylpiperidin-4-yl)-4-(4-chlorophenyl)benzylamine |
| D85 | Int. D18 | 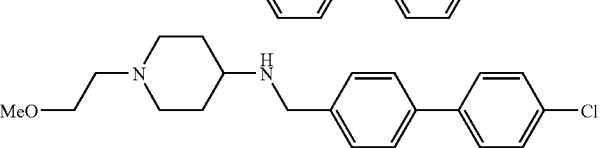 | N-(1-(2-methoxyethyl)piperidin-4-yl)-4-(4-chlorophenyl)benzylamine |

Example 1

N-(2-Diethylaminoethyl)-2-(2-(2-(2,3-difluorophenyl)-ethyl)-4-oxo-4H-quinazolin-1-yl)-N-(4'-triflouromethlyl-bipheny-4-ylmethyl)acetamide bitartrate

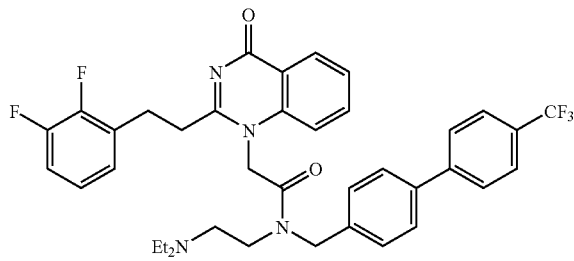

A solution of N-(2-(diethylamino)ethyl)-4-(4-trifluoromethylphenyl)benzylamine (Intermediate D4) (0.25 g, 0.73 mmol), 1-(3-dimethylaminopropyl)-3-ethylcarbodiimide (DEC) (0.28 g, 1.45 mmol), 1-hydroxybenzotriazole hydrate (0.10 g, 0.73 mmol), 2-(2-(2-(2,3-difluorophenyl)-ethyl)-4-oxo-4H-quinazolin-1-yl)-acetic acid (Int. C43) (0.25 g, 0.73 mmol) in dichloromethane (20 ml) was stirred at ambient temperature overnight then diluted with dichloromethane, washed with aqueous sodium bicarbonate and evaporated. The residue was purified by chromatography (10 g silica cartridge, 20% methanol in ethyl acetate) to give the title compound, as the free base, as a yellow foam (0.43 g, 88%). $^1$H-NMR (CDCl$_3$, rotamer mixture) δ 0.98–1.04 (6H, m), 2.50–2.67 (6H, m), 2.85–3.02 (2H, m), 3.23–3.66 (4H, m), 4.71/4.85/5.28 (4H, 3×s), 6.86–7.53 (9H, m), 7.63–7.73 (5H, m), 8.34/8.40 (1H, 2×d); MS (APCI+) found (M+1)=677; C$_{38}$H$_{37}$F$_5$N$_4$O$_2$ requires 676.

A solution of d-tartaric acid (0.94 g, 0.62 mmol) and the title compound as the free base (0.42 g, 0.62 mmol) in methanol (2 ml) was evaporated to give a yellow foam which was triturated with ether, filtered, and dried in vacuo to yield the salt (0.49 g, 96%). $^1$H-NMR (CDCl$_3$, rotamer mixture) δ 0.89–1.02 (6H, m), 2.55–3.50 (12H, m), 4.23 (2H, s), 4.64/4.88 (2H, 2×s), 5.29/5.53 (2H, 2×s), 7.10–7.86 (14H, m), 8.10 (1H, t). MS (APCI+) found (M+1)=677; C$_{38}$H$_{37}$F$_5$N$_4$O$_2$ requires 676.

Example 2

N-(2-Diethylaminoethyl)-2-(5-ethyl-2-[2-(4-fluorophenyl)ethyl]-4-oxo-4H-pyrimidin-1-yl)-N-(4'-trifluoromethylbiphenyl-4-ylmethyl)acetamide bitartrate

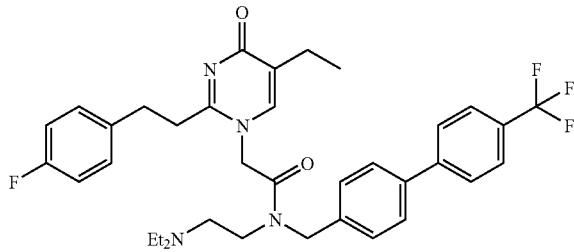

2-(5-Ethyl-2-[2-(4-fluorophenyl)ethyl]-4-oxo-4H-pyrimidin-1-yl)acetic acid (Int. C2) (150 mg), 1-(3-dimethylaminopropyl)-3-ethylcarbodiimide hydrochloride(89mg), 1-hydroxybenzotriazole hydrate, (67 mg) and N,N-diethyl-N'-(4'-trifluoromethylbiphenyl-4-ylmethyl)ethane-1,2-diamine (Int. D4) (173 mg) were combined in dichloromethane (20 ml) at room temperature and stirred for 24 h. The solution was washed with saturated sodium bicarbonate, brine, dried and concentrated. The crude product was purified by column chromatography (silica gel, 40% methanol/ethyl acetate). The title compound was obtained as a yellow foam, (277 mg, 89%); $^1$H-NMR (CDCl$_3$) ca 2:1 mixture of rotamers δ 0.94/0.99 (6H, t, J=7.1 Hz), 1.14 (3H, m), 2.42–2.75 (10H, m), 3.07/3.15 (2H, t, J=8.3Hz), 3.25/3.59 (2H, t, J=4.8 Hz), 4.34/4.66 (2H, s), 4.66/4.83 (2H, s) and 6.86–7.74 (13H, m). (APCI+) Found (M+1)=637, C$_{36}$H$_{40}$F$_4$N$_4$O$_2$ requires 636. The bitartrate salt was prepared by treatment of the free base (270 mg) in methanol (2 ml) with d-tartaric acid, (64 mg). The solution was concentrated to a yellow foam, and triturated with ether to give the title compound as a yellow solid, (314 mg, 94%), $^1$H-NMR (DMSO) ca 2:1 mixture of rotamers δ 0.90/0.97 (6H, t, J=7.2 Hz), 1.06 (3H, m), 2.27 (2H, m), 2.50 (2H, m), 2.68 (6H, m), 2.93 (2H, m), 3.37/3.45 (2H, t, J=6.0 Hz), 4.21 (2H, s), 4.64/4.71 (2H, s), 4.99/5.15 (2H, s) and 7.06–7.85 (13H, m),

Example 3

N-2-Diethylaminoethyl)-2-[2-(2-(2,3-difluorophenyl)ethyl)-4-oxo-4,5,6,7tetrahydro-cyclopentapyrimidin-1-yl]-N-(4'-trifuoromethyl-biphenyl-4-ylmethyl)acetamide bitartrate

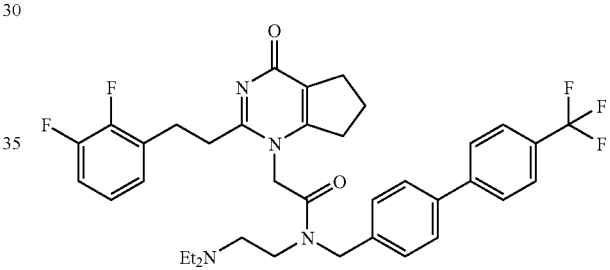

A solution of N,N-diethyl-N'-(4'-trifluoromethyl-biphenyl-4-ylmethyl)-ethane-1,2-diamine (Int D4) (0.50 g, 1.44 mmol), 1-(3-dimethylaminopropyl)-3-ethylcarbodiimide (0.56 g, 1.45 mmol), 1-hydroxybenzotriazole hydrate (0.12 g) and 2-(2-[2-(2,3-difluorophenyl)-ethyl]-4-oxo-4,5,6,7-tetrahydro-cyclopentapyrimidin-1-yl)-acetic acid (Int C1) (0.48 g, 1.44 mmol) in dichloromethane (10 ml) was stirred at ambient temperature overnight then diluted with dichloromethane (30 ml), washed with aqueous sodium bicarbonate and evaporated. The residue was purified by chromatography (10 g silica cartridge, ethyl acetate-acetone) to give the title compound as a yellow foam (free base) (0.50 g, 52%). $^1$H-NMR (DMSO, rotamer mixture) δ 0.83–0.89 (6H, m), 1.98 (2H, m), 2.40 (4H, m), 2.45–2.82 (10H, m), 3.02 (2H, m), 4.64/4.75 (2H,2×s), 4.96/5.19 (2H,2×s), 7.11–7.40 (5H, m), 7.65 (2H, m), 7.84 (4H, m); MS (APCI+) found (M+1)=667; C$_{37}$H$_{39}$F$_5$N$_4$O$_2$ requires 666.

d-Tartaric acid (0.09 g, 0.60 mmol) was added to a solution of the free base (0.40 g, 0.60 mmol) in methanol (10 ml) with stirring. The resulting solution was evaporated to yield the salt (0.49 g). $^1$H-NMR (DMSO, rotamer mixture) δ 0.85–0.97 (6H, m), 1.91–2.00 (2H, m), 2.40–2.49 (4H, m), 2.54–2.82 (10H, m), 3.02–3.46 (2H, m), 4.20 (2H, s), 4.64/4.75 (2H, 2×s), 4.97/5.18 (2H, 2×s), 7.11–7.40 (5H, m), 7.65 (2H, m), 7.84 (4H, m); MS (APCI+) found (M+1)=667; C$_{37}$H$_{39}$F$_5$N$_4$O$_2$ requires 666.

Example 4

N-(2-Diethylaminoethyl)-2-[2-2-(2,3 difluorophenyl)ethyl]-4-oxo-4H-thieno[3,2-d]pyrimidin-1-yl]-N-(4'-trifluoromethylbiphenyl-4-ylmethyl)acetamide bitartrate

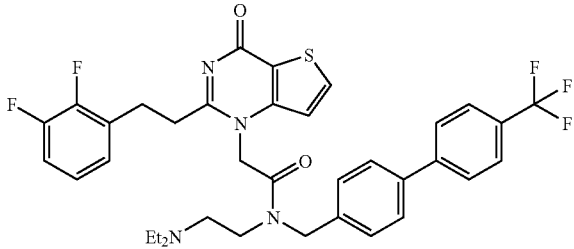

2-2-[2-(2,3-Difluorophenyl)ethyl]-4-oxo-4H-thieno[3,2-d]pyrimidin-1-yl)acetic acid, (Int. C39) (150mg), 1-(3-dimethylaminopropyl)-3-ethylcarbodiimide hydrochloride (164 mg), 1-hydroxybenzotriazole hydrate (58 mg) and N,N-diethyl-N'-(4'-trifluoromethylbiphenyl-4-ylmethyl)ethane-1,2-diamnine (Int. D4) (150mg) were combined in dichloromethane (5 ml) at room temperature and stirred for 24 h. The solution was washed with saturated sodium bicarbonate, brine, dried and concentrated. The crude product was purified by column chromatography on silica gel eluting with 40% methanol/ethyl acetate. The title compound was obtained as a yellow foam, (260 mgs,.89%), $^1$H-NMR (CDCl$_3$) ca 2:1 mixture of rotamers δ 1.00 (6H, t, J6.8 Hz), 2.57 (4H, q, J6.8 Hz), 2.64 (2H, m), 2.83/2.96 (2H, t, J8.4 Hz), 3.24/3.30 (2H, t, J8.4 Hz), 3.39/3.65 (2H, m), 4.68/4.82 (2H, s), 5.30 (2H, s), 6.95–7.06 (5H, m), 7.32/7.36 (1H, d, J8.4 Hz), 7.52/7.60 (1H, d, J8.2 Hz) and 7.62–7.72 (6H, m). (APCI+) Found (M+1)=683, C$_{36}$H$_{35}$F$_5$N$_4$O$_2$S requires 682.

The free base (260mg) in methanol (2 ml) was treated with d-tartaric acid (57mg). The solution was concentrated to a colourless foam and triturated with ether to give the title compound as a colourless solid (304 mg, 96%), $^1$H-NMR (DMSO) ca 2:1 mixture of rotamers δ 0.90/0.98 (6H, t, J7.0 Hz), 2.72–3.51 (10H, complex m), 4.22 (2H, s), 4.64/4.83 (2H, s), 5.34/5.55 (2H, s), 7.14–7.44 (6H, m), 7.65 (2H, m), 7.83 (4H, m) and 8.13/8.17 (1H, d, J5.4 Hz).

Example 5

N-2-Diethylaminoethyl)2-[6-(2-(2,3-difluorophenyl)ethyl)-2-methyl-4-oxo-2,4-dihydro-pyrazolo[3,4d]pyrimidin-7-yl]-N-(4'-trifluoromethyl-biphenyl-4-ylmethyl)acetamide bitartrate

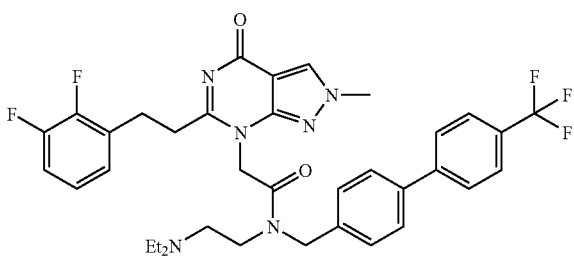

A solution of N,N-diethyl-N'-(4'-trifluoromethyl-biphenyl-4-ylmethyl)-ethane-1,2-diamine (Int. D4) (0.54 g, 0.73 mmol), 1-(3-dimethylaminopropyl)-3-ethylcarbodiimide (0.58g, 3.04 mmol), 1-hydroxybenzotriazole hydrate (0.03 g), {6-[2-(2,3-difluorophenyl)-ethyl]-2-methyl-4-oxo-2,4-dihydro-pyrazolo[3,4-d]pyrimidin-7-yl}-acetic acid (Int. C41) (0.54, 1.52 mmol) and N,N-diisopropylethylamine (0.27 ml, 1.55 mmmol) in dichloromethane (6 ml) was stirred at ambient temperature overnight then diluted with dichloromethane, washed with aqueous sodium bicarbonate and evaporated. The residue was purified by chromatography (10 g silica cartridge, dichloromethane-2% methanolic ammonia/dichloromethane) to give the title compound as a white solid (0.14 g, 13%). $^1$H-NMR (DMSO, rotamer mixture) δ 0.83–0.93 (6H, m), 2.22–2.58 (6H, m), 2.86–2.95 (2H, m), 3.06–3.15 (2H, m), 3.32–3.40 (2H, m), 3.97 (3H, s), 4.64/4.81 (2H, 2×s), 5.19/5.40 (2H, 2×s), 7.09–7.87 (11H, m), 8.37 (1H, 2×s); MS (APCI+) found (M+1)=681; C$_{36}$H$_{37}$F$_5$N$_6$O$_2$ requires 680.

d-Tartaric acid (0.031 g, 0.21 mmol) was added to a solution of the free base (0.14 g, 0.21 mmol) in methanol (5 ml) with stiring. The resulting solution was evaporated to yield the salt (0.24 g). $^1$H-NMR (DMSO, rotamer mixture) δ 0.94–0.99 (6H, m), 2.51–2.93 (8H, m), 3.11 (2H, m), 2H, m), 3.74 (2H, m), 3.98 (3H, s), 4.18 (2H, s), 4.64/4.81 (2H, 2×s), 5.22/5.40 (2H, 2×s), 7.09–7.87 (11H, m), 8.39 (1H, s); MS (APCI+) found (M+1)=681; C$_{36}$H$_{37}$F$_5$N$_6$O$_2$ requires 680.

Example 6

N-(2-Diethylaminoethyl)-(2-(2-(2,3-difluorophenyl)ethyl)-4-oxo-4H-pyrido[2,3-d]pyrimidin-1-yl)-N-(4-(4-trifluoromethylphenyl)phenyl)methylacetamide bitartrate

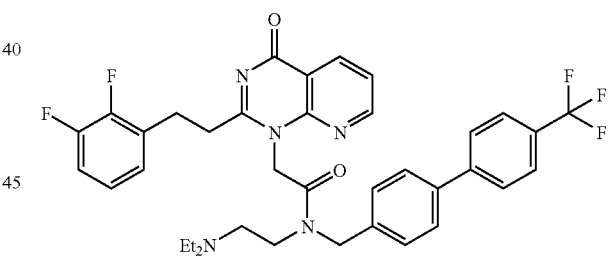

Intermediate C35 (0.33 g) and intermediate D4 (0.37 g) were stirred together in an ice bath under argon in dimethylformamide. Diisopropylethylamine (0.36 ml) and O-(7-azabenzotriazol-1-yl)-N,N,N',N'-tetramethyluronium hexafluorophosphate (HATU) (0.43 g) were added and stirred for 30 min. Solvent was removed under reduced pressure and the residue partitioned between dichloromethane and water, filtered through celite and the organic layer washed with further water and dried over K$_2$CO$_3$. The solvent was removed under reduced pressure and the residue chromatographed on silica gel, eluting with 5% methanol in dichloromethane, to give a solid. The celite pad was washed with methanol and concentrated. The residue was dissolved in 9:1 dichloromethane:methanol and washed with water. Drying, evaporation and chromatography as above gave a material which was combined with the product from the previous chromatography (total yield=0.21 g). This material dissolved in methanol and a solution of tartaric acid (0.046 g) in methanol added. The solvent was removed under reduced pressure and the residue triturated with Et$_2$O to give the title compound (0.235 g). Rotamers were present in the $^1$H-NMR (d$_6$-DMSO) δ 0.90–1.11 (6H, m), 2.67–3.50 (m), 4.20 (2H, s), 4.64 & 4.87 (2H, 2s), 5.51 & 5.68 (1H, 2×brs), 7.12–7.19 (1H, m), 7.24–7.36 (3H, m), 7.58–7.66 (3H, m), 7.80–7.93 (5H, m), 8.47–8.50 (1H, m) 8.85–8.89 (1H, m); MS (APCI+) found (free base M+1)=678; C$_{37}$H$_{36}$ F$_5$N$_5$O$_2$ requires 677.

Example 7

N-(1-Methylpiperidin-4-yl)-(2-(2-2,3-difluorophenyl)ethyl)-4-oxo-4H-quinazolin-1-yl)-N-(4-(4-trifluoromethylphenyl)phenyl)methylacetamide bitartrate

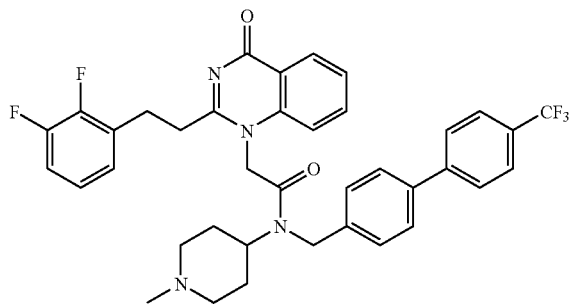

Intermediate C43 (0.2 g) and intermediate D8 (0.2 g) were stirred together in an ice bath under argon in dichloromethane. Diisopropylethylamine (0.23 ml) and O-(7-azabenzotriazol-1-yl)-N,N,N',N'-tetramethyluronium hexafluorophosphate (HATU) (0.26 g) were added and stirred overnight. After diluting with dichloromethane, the mixture was washed with water and chromatographed on silica gel eluting with 6–13% methanol in dichloromethane. This gave a solid (0.26 g) which was converted to the bitartrate salt (title compound) with tartaric acid as in example 6. $^1$H-NMR (DMSO, rotamer mixture) δ 1.6–2.0 (4H, m), 2.2–2.5 (5H, m), 2.5–3.9 (6H, m), 4.0–4.1+4.25–4.4 (1H, 2×m), 4.56+ 4.85+5.1+5.58 (4H, 4×br.s), 7.05–7.7 (9H, 2×br.m), 7.7–7.95 (5H, m), 8.1 (1H, t); MS (APCI+) found (M+1)= 675; C$_{38}$H$_{35}$F$_5$N$_4$O$_2$ requires 674.

Example 8

N-(1-Ethylpiperidin-4-yl)-(2-(2-(2,3-difluorophenyl)ethyl)-4oxo-4H-quinazolin-1yl)-N-(5-(4-trifluoromethylphenyl)thien-2-yl)methylacetamide bitartrate

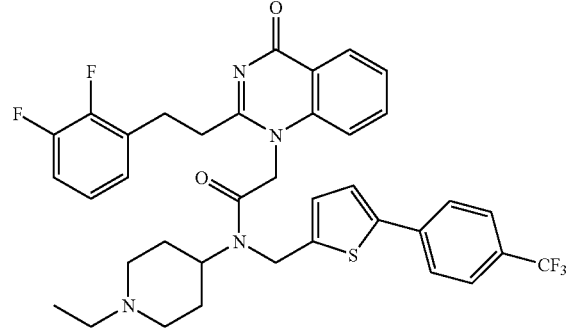

The title compound was prepared from intermediates C43+D77 in dimethylformamide using O-(7-azabenzotriazol-1-yl)-N,N,N',N'-tetramethyluronium hexafluorophosphate (HATU) as a coupling agent, followed by bitartrate salt formation using the methods described in examples 6 and 7. $^1$H-NMR (DMSO, rotamer mixture) δ 1.0–1.2 (3H, m), 1.6–2.2 (4H, m), 2.2–2.75 (4H, m), 2.75-3.9 (6H, m), 3.94–4.1+4.15–4.35 (1H, 2×m), 4.15 (2H, s), 4.7+4.95 (2H, 2×br.s), 5.3+5.5 (2H, 2×br.s), 6.9–7.55 (8H, 2×br.s), 7.7–7.95 (4H, m), 8.1 (1H, t); MS (APCI+) found (M+1)= 695; C$_{37}$H$_{35}$F$_5$N$_4$O$_2$S requires 694.

Example 9

N-(1-Ethylpiperidin-4-yl)-(2-(2-(2,3-difluorophenyl)ethyl)-4-oxo-4H-quinazolin-1-yl)-N-(4-(5-trifluoromethylthien-2-yl)phenyl)methylacetamide bitartrate

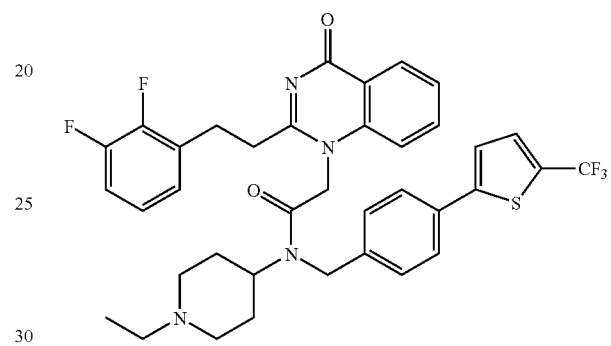

The title compound was prepared from intermediates C43+D79 in dimethylformamide using O-(7-azabenzotriazol-1-yl)-N,N,N',N'-tetramethyluronium hexafluorophosphate (HATU) as a coupling agent, followed by bitartrate salt formation using the methods described in examples 6 and 7. $^1$H-NMR (DMSO, rotamer mixture) δ 1.05–1.14 (3H, m), 1.70–2.00 (4H, m), 2.48–3.21 (10H, m), 4.09 (2H, s), 4.14/4.41 (1H, 2×br m), 4.41/4.84 (2H, 2×s), 5.11/5.60 (2H, 2×s), 7.09–8.12 (13H, m); MS (APCI+) found (M+1)=695; C$_{37}$H$_{35}$F$_5$N$_4$O$_2$S requires 694.

Example 10

N-(1-Methylpiperidin-4-yl)-(2-(2-2,3-difluorophenyl)ethyl)-4-oxo-4H-pyrido[2,3-d]pyrimidin-1-yl)-N-(4-(4-trifluoromethylphenyl)phenyl)methylacetamide bitartrate

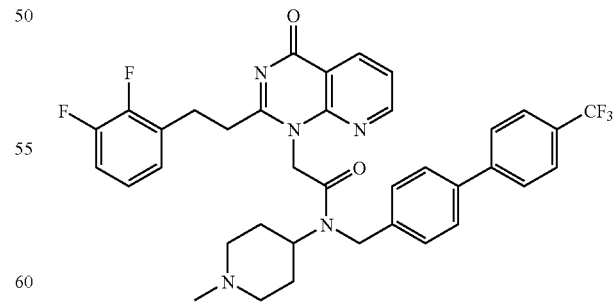

The title compound was prepared from intermediates C35+D8 in dimethylformamide using O-(7-azabenzotriazol-1-yl)-N,N,N',N'-tetramethyluronium hexafluorophosphate (HATU) as a coupling agent, followed by bitartrate salt formation using the methods described in examples 6 and 7.

¹H-NMR (DMSO, rotamer mixture) δ 1.60–1.91 (4H, m), 2.37–2.42 (5H, m), 3.04–3.18 (6H, m), 4.09/4.26 (1H 2×br m), 4.14 (2H, s), 4.60/4.83 (2H, 2×s), 5.40/5.68 (2H, 2×s), 7.13–7.18 (1H, m), 7.25–7.33 (3H, m), 7.57–7.67 (3H, m), 7.78–7.92 (5H, m), 8.46–8.49 (1H, m), 8.88–8.93 (1H, m); MS (APCI+) found (M+1)=676; $C_{37}H_{34}F_5N_5O_2$ requires 675.

Example 11

N-(1-(2-Methoxyethyl)piperidin-4-yl)-(2-(2-(2,3-difluorophenyl)ethyl)-4-oxo-4H-pyrido[2,3-d]pyrimidin-1-yl)-N-(4-(4-trifluoromethylphenyl)phenyl)methylacetamide bitartrate

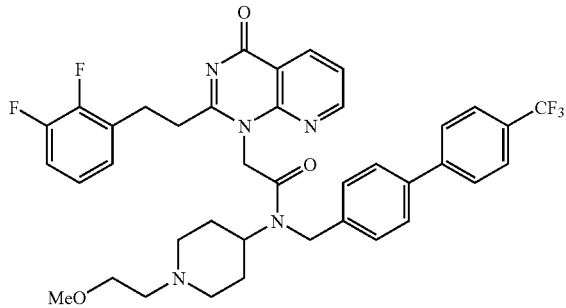

The title compound was prepared from intermediates C35+D80 in dimethylformnamide using O-(7-azabenzotriazol-1-yl)-N,N,N',N'-tetramethyluronium hexafluorophosphate (HATU) as a coupling agent, followed by bitartrate salt formation using the methods described in examples 6 and 7. ¹H-NMR (DMSO, rotamer mixture) δ 1.56–1.82 (4H, m), 2.23–2.37 (2H, m), 2.63–2.66 (2H, m), 3.02–3.18 (6H, m), 3.20/3.23 (3H, 2×s), 3.40–3.46 (2H, m), 4.05/4.26 (1H 2×br m), 4.19 (2H, s), 4.61/4.83 (2H, 2×s), 5.39/5.68 (2H, 2×s), 7.13–7.17 (1H, m), 7.25–7.33 (3H, m), 7.57–7.66 (3H, m), 7.78–7.92 (5H, m), 8.45–8.49 (1H, m), 8.88–8.93 (1H, m); MS (APCI+) found (M+1)=720; $C_{39}H_{38}F_5N_5O_3$ requires 719.

The following amide Examples were prepared from the corresponding acetic acid and amine using 1-(3dimethylaminopropyl)-3-ethylcarbodiimide with or without 1-hydroxybenzotriazole hydrate as coupling agent (as for Examples 1–5), though a few were prepared using O-(7-azabenzotriazol-1-yl)-N,N,N',N'-tetramethyluronium hexafluorophosphate (HATU) as a coupling agent (as for Examples 6 and 7), followed by treatment with d-tartaric acid to give the salt if indicated.

| No. | Precursors | Structure | Name |
|---|---|---|---|
| 20 | C1 + D34 | 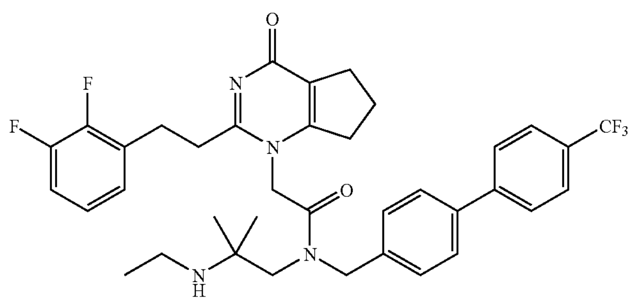 | N-(2-ethylamino-2-methyl-propyl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |
| 21 | C1 + D38 | 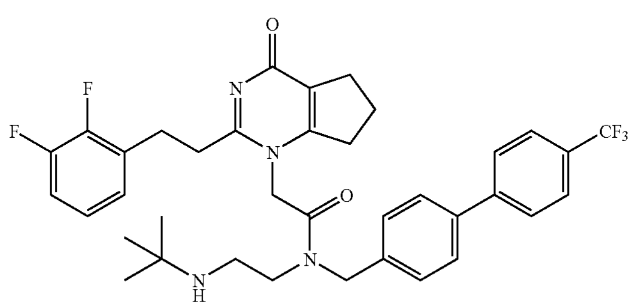 | N-(2-t-butylaminoethyl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |

| No. | Precursors | Structure | Name |
|---|---|---|---|
| 22 | C1 + D47 | 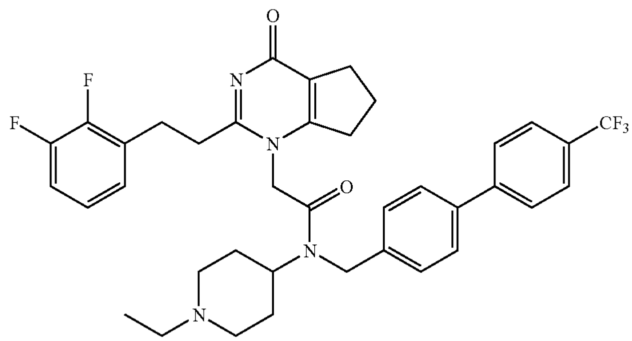 | N-(1-ethyl-piperidin-4-yl)-2-(2-(2-(2,3-difluorophenyl)-ethyl)-4-oxo-4,5,6,7-tetrahydro-cyclopenta-pyrimidin-1-yl)-N-(4'-trifluoromethyl-biphenyl-4-ylmethyl)-acetamide bitartrate |
| 23 | C3 + D4 | 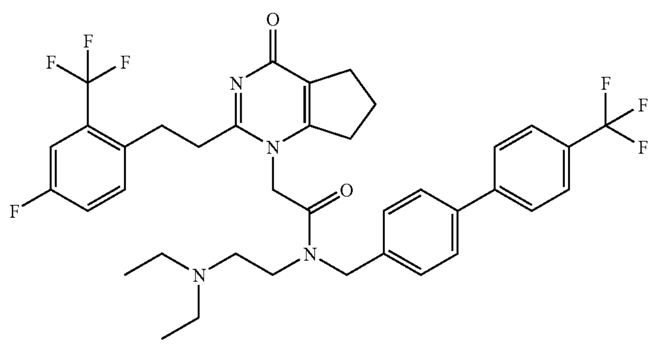 | N-(2-diethylaminoethyl)-2-(2-(2-(4-fluoro-2-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)-acetamide bitartrate |
| 24 | C4 + D4 | 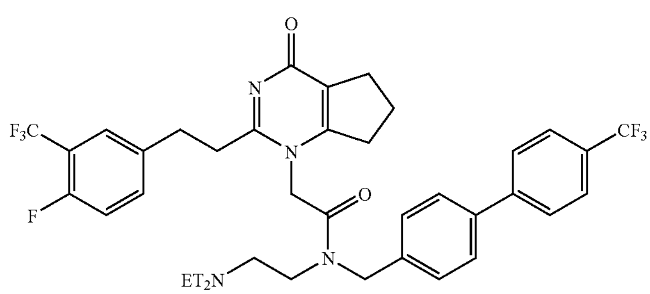 | N-(2-diethylaminoethyl)-2-(2-(2-(4-fluoro-3-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)-acetamide bitartrate |
| 25 | C5 + D4 | 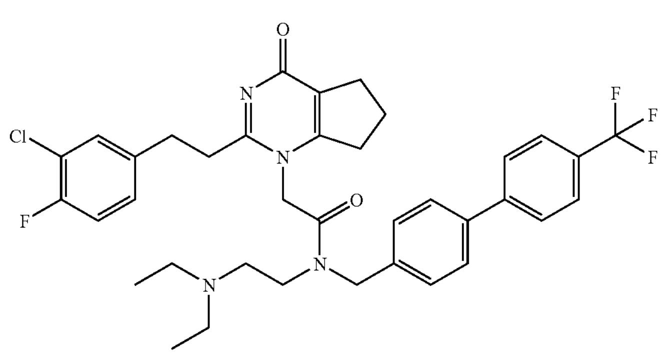 | N-(2-diethylaminoethyl)-2-(2-(2-(3-chloro-4-fluorophenyl)-ethyl)-4-oxo-4,5,6,7-tetrahydro-cyclopenta-pyrimidin-1-yl)-N-(4'-trifluoromethyl-biphenyl-4-ylmethyl)acetamide bitartrate |

-continued

| No. | Precursors | Structure | Name |
|---|---|---|---|
| 26 | C6 + D4 | 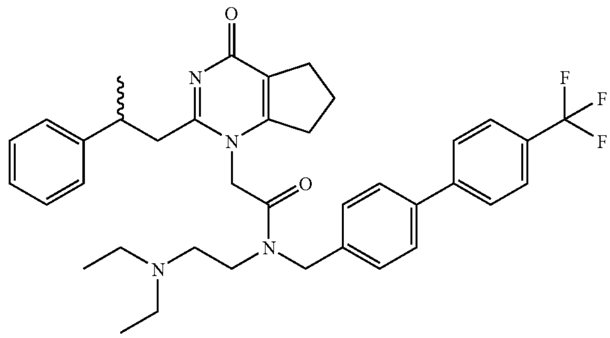 | (+/−)-N-(2-diethylaminoethyl)-2-(2phenyl-propyl)-4-oxo-4,5,6,7-tetrahydro-cyclopentapyrimidin-1-yl)-N-(4'-trifluoromethyl-biphenyl-4-ylmethyl)acetamide bitartrate |
| 27 | C7 + D4 | 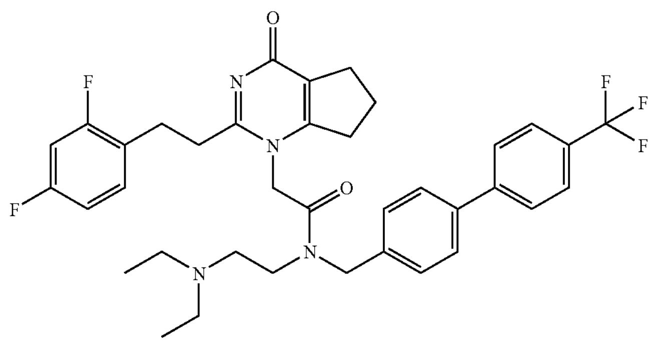 | N-(2-diethylaminoethyl)-2-(2-(2-(2,4-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |
| 28 | C8 + D4 | 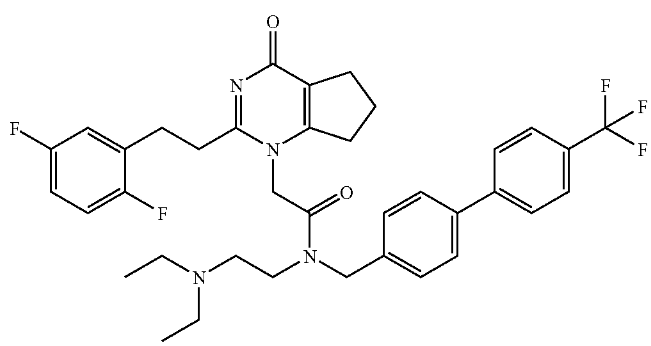 | N-(2-diethylaminoethyl)-2-(2-(2-(2,5-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |
| 29 | C9 + D4 | 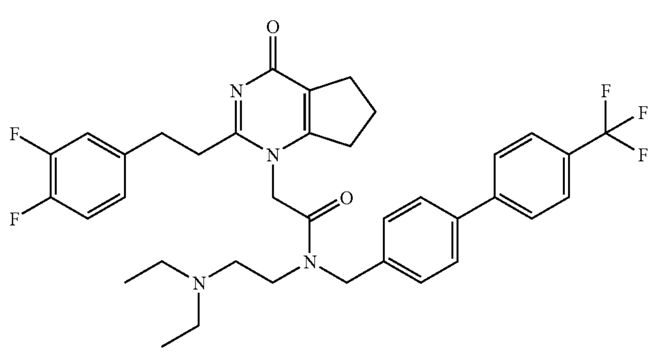 | N-(2-diethylaminoethyl)-2-(2-(2-(3,4-difluorophenyl)-ethyl)-4-oxo-4,5,6,7-tetrahydro-cyclopentapyrimidin-1-yl)-N-(4'-trifluoromethyl-biphenyl-4-ylmethyl)acetamide |

| No. | Precursors | Structure | Name |
|---|---|---|---|
| 30 | C10 + D4 | 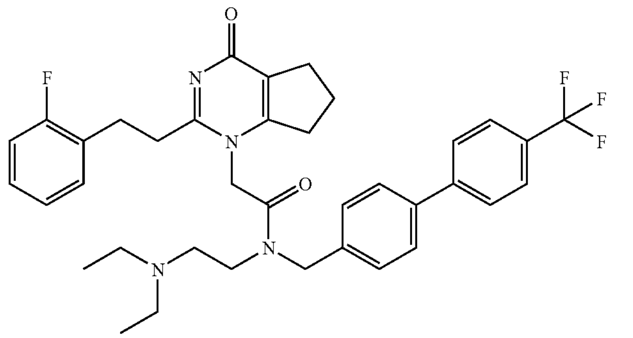 | N-(2-diethylaminoethyl)-2-(2-(2-(2-fluorophenyl)-ethyl)-4-oxo-4,5,6,7-tetrahydro-cyclopentapyrimidin-1-yl)-N-(4'-trifluoromethyl-biphenyl-4-ylmethyl)acetamide |
| 31 | C11 + D4 | 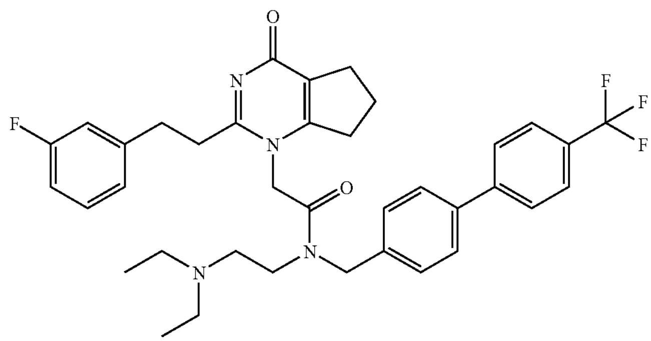 | N-(2-diethylaminoethyl)-2-(2-(2-(3-fluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |
| 32 | C12 + D4 | 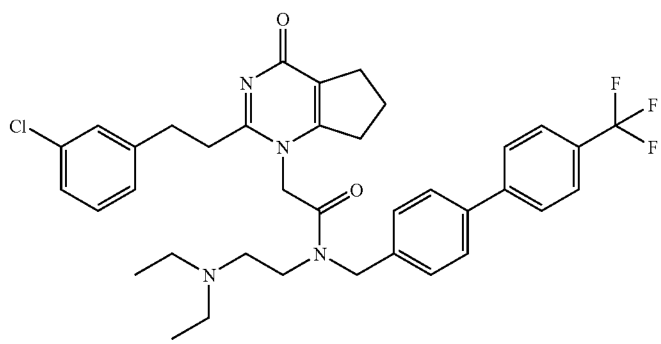 | N-(2-diethylaminoethyl)-2-(2-(2-(3-chlorophenyl)-ethyl)-4-oxo-4,5,6,7-tetrahydro-cyclopentapyrimidin-1-yl)-N-(4'-trifluoromethyl-biphenyl-4-ylmethyl)acetamide |
| 33 | C13 + D4 | 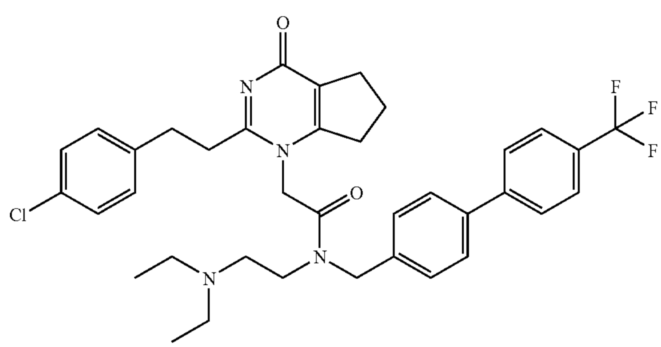 | N-(2-diethylaminoethyl)-2-(2-(2-(4-chlorophenyl)-ethyl)-4-oxo-4,5,6,7-tetrahydro-cyclopentapyrimidin-1-yl)-N-(4'-trifluoromethyl-biphenyl-4-ylmethyl)acetamide |

| No. | Precursors | Structure | Name |
|---|---|---|---|
| 34 | C14 + D4 | 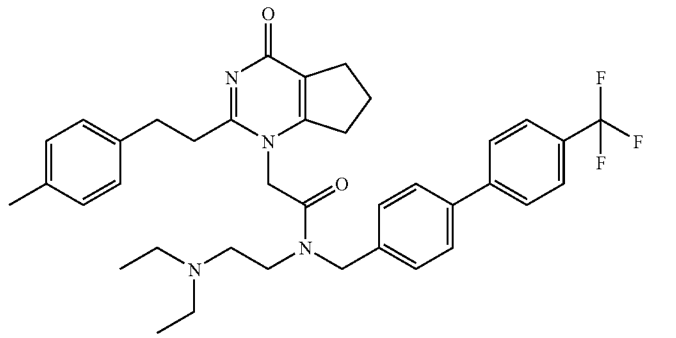 | N-(2-diethylaminoethyl)-2-(2-(2-(4-methylphenyl)-ethyl)-4-oxo-4,5,6,7-tetrahydro-cyclopentapyrimidin-1-yl)-N-(4'-trifluoromethyl-biphenyl-4-ylmethyl)acetamide |
| 35 | C15 + D4 | 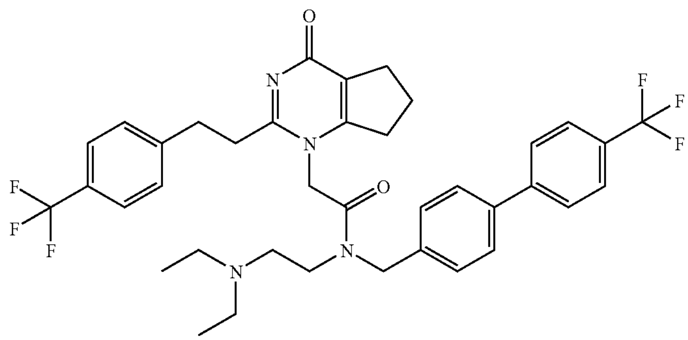 | N-(2-diethylaminoethyl)-2-(2-(2-(4-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)acetamide |
| 36 | C16 + D4 | 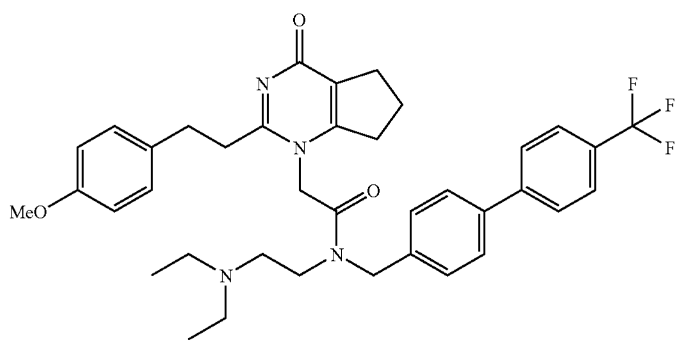 | N-(2-diethylaminoethyl)-2-(2-(2-(4-methoxyphenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |
| 37 | C17 + D4 | 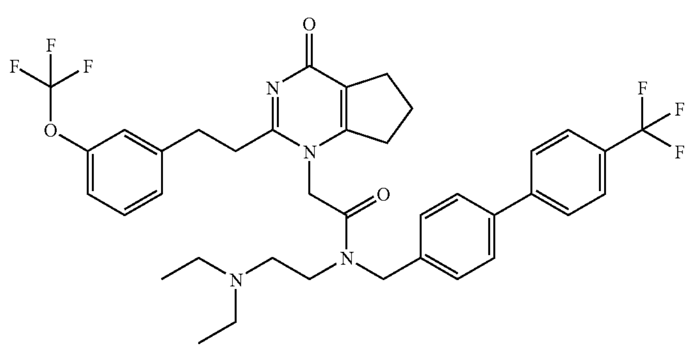 | N-(2-diethylaminoethyl)-2-(2-(2-(4-(trifluoromethoxy)phenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |

-continued

| No. | Precursors | Structure | Name |
|---|---|---|---|
| 38 | C18 + D4 | 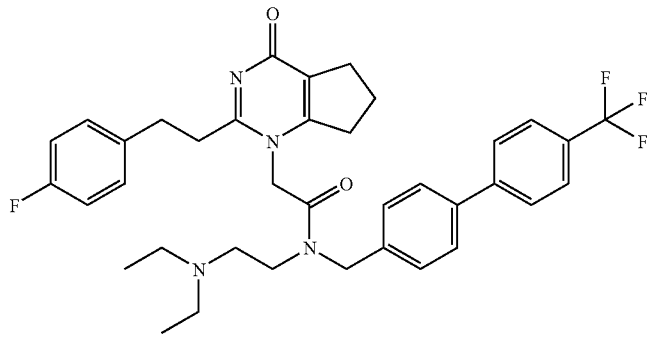 | N-(2-diethylaminoethyl)-2-(2-(2-(4-fluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate |
| 39 | C19 + D4 | 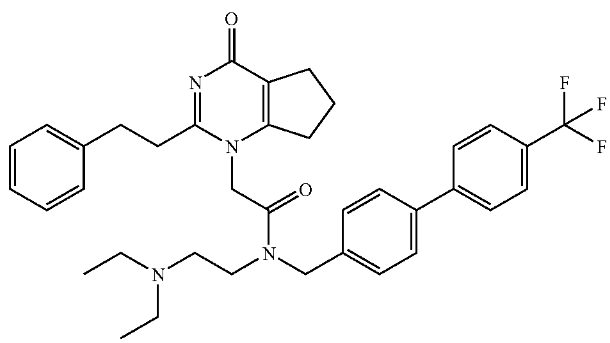 | N-(2-diethylaminoethyl)-2-(2-(2phenylethyl)-4-oxo-4,5,6,7-tetrahydrocyclopentapyrimidin-1-yl)-N-(4'-trifluoromethyl-biphenyl-4-ylmethyl)bitartrate |
| 40 | C20 + D4 | 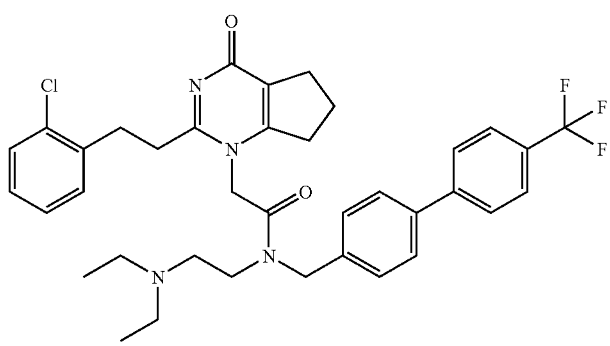 | N-(2-diethylaminoethyl)-2-(2-(2-(2-chlorophenyl)-ethyl)-4-oxo-4,5,6,7-tetrahydro-cyclopentapyrimidin-1-yl)-N-(4'-trifluoromethyl-biphenyl-4-ylmethyl)acetamide |
| 41 | C21 + D4 | 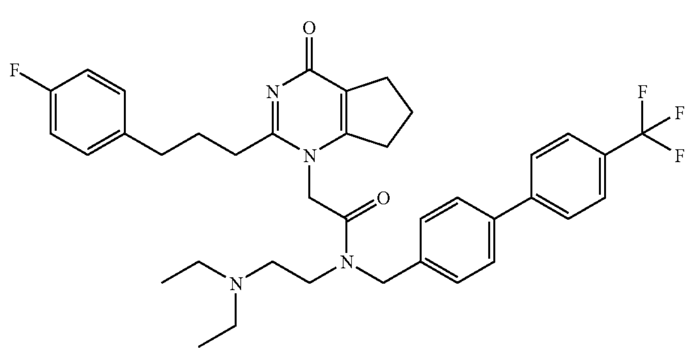 | N-(4'-diethylaminoethyl)-2-(2-(3-(4-fluorophenyl)-propyl)-4-oxo-4,5,6,7-tetrahydro-cyclopentapyrimidin-1-yl)-N-(4'-trifluoromethyl-biphenyl-4-ylmethyl)acetamide bitartrate |

-continued

| No. | Precursors | Structure | Name |
|---|---|---|---|
| 42 | C30 + D4 | 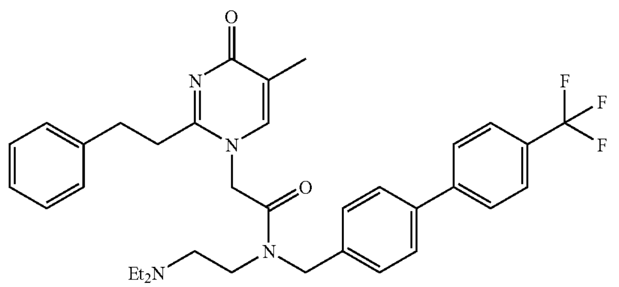 | N-(2-Diethylaminoethyl)-2-[2-[2-phenylethyl]-5-methyl-4-oxo-4H-pyrimidin-1-yl]-N-(4'-trifluoromethyl-biphenyl-4-ylmethyl)acetamide |
| 43 | C31 + D4 | 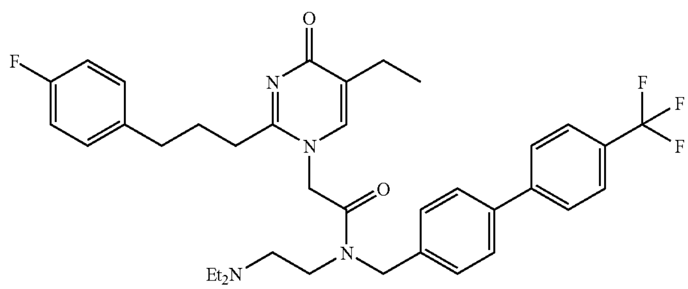 | N-(2-Diethylaminoethyl)-2-[2-[3-(4-fluorophenyl)-propyl]-5-ethyl-4-oxo-4H-pyrimidin-1-yl]-N-(4'-trifluoromethylbiphenyl-4-ylmethyl)acetamide bitartrate |
| 44 | C32 + D4 | 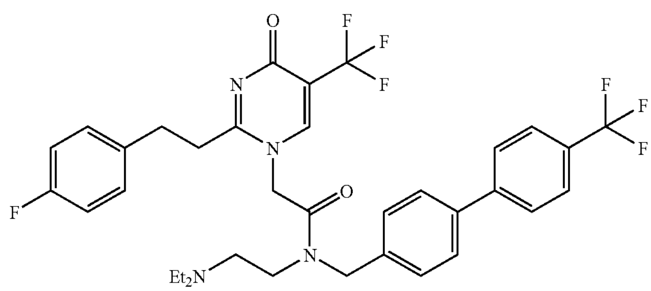 | N-(2-Diethylaminoethyl)-2-[2-(2-(4-fluorophenyl)-ethyl)-5-(2,2,2-trifluoroethyl)-4-oxo-4H-pyrimidin-1-yl]-N-(4'-trifluoromethyl-biphenyl-4-ylmethyl)acetamide bitartrate |
| 45 | C22 + D4 | 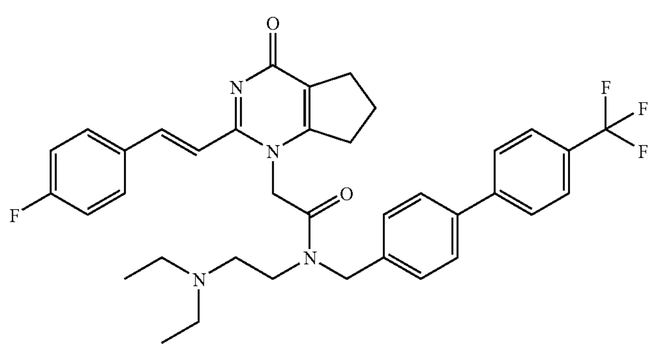 | N-(2-diethylaminoethyl)-2-(2-(2-(4-fluorophenyl)-vinyl)-4-oxo-4,5,6,7-tetrahydro-cyclopentapyrimidin-1-yl)-N-(4'-trifluoromethyl-biphenyl-4-ylmethyl)acetamide bitartrate |
| 46 | C33 + D4 | 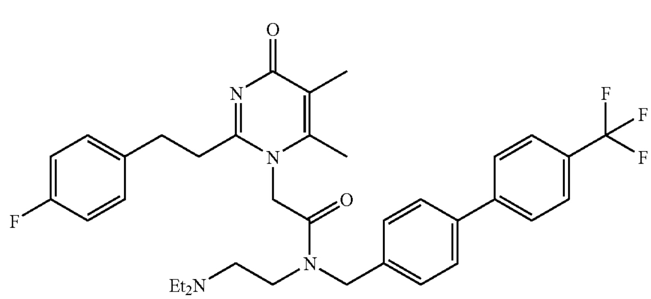 | N-(2-Diethylaminoethyl)-2-[2-(2-(4-fluorophenyl)-ethyl)-5,6-dimethyl-4-oxo-4H-pyrimidin-1-yl]-N-(4'-trifluoromethylbiphenyl-4-ylmethyl)-acetamide bitartrate |

-continued

| No. | Precursors | Structure | Name |
|---|---|---|---|
| 47 | C36 + D5 | 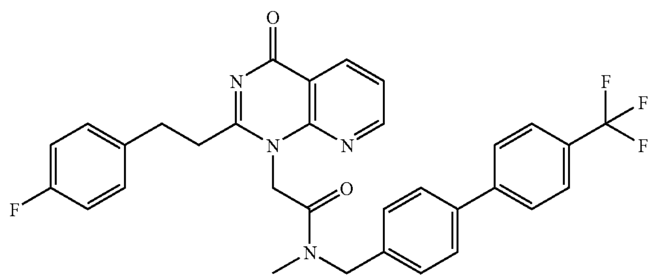 | N-Methyl-2-(2-(2-(4-fluorophenyl)-ethyl)-4-oxo-4H-pyrido[2,3-d]-pyrimidin-1-yl)-N-(4'-trifluoromethyl-biphenyl-4-ylmethyl)acetamide |
| 48 | C36 + D4 | 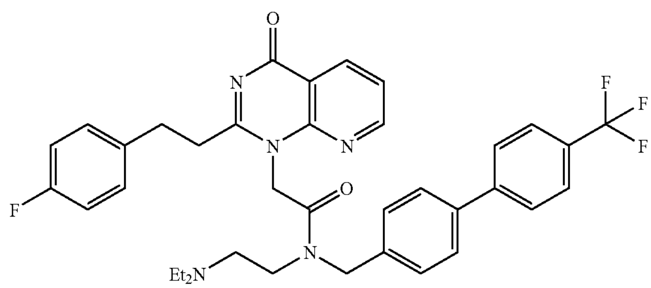 | N-(2-Diethylaminoethyl)-2-(2-(2-(4-fluorophenyl)ethyl)-4-oxo-4H-pyrido[2,3-d]pyrimidin-1-yl)-N-(4'-trifluoromethylbiphenyl-4-ylmethyl)-acetamide bitartrate |
| 49 | C37 + D4 | 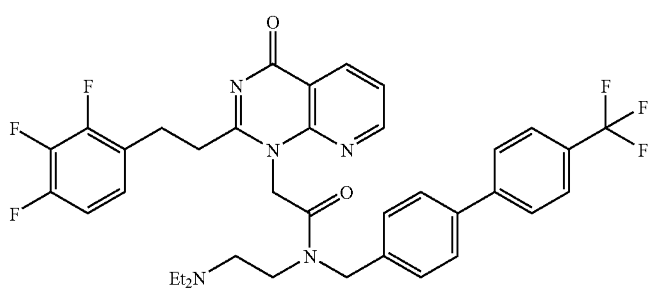 | N-(2-Diethylaminoethyl)-2-(2-(2-(2,3,4-trifluorophenyl)ethyl)-4-oxo-4H-pyrido[2,3-d]pyrimidin-1-yl)-N-(4'-trifluoromethyl-biphenyl-4-ylmethyl)acetamide bitartrate |
| 50 | C72 + D4 | 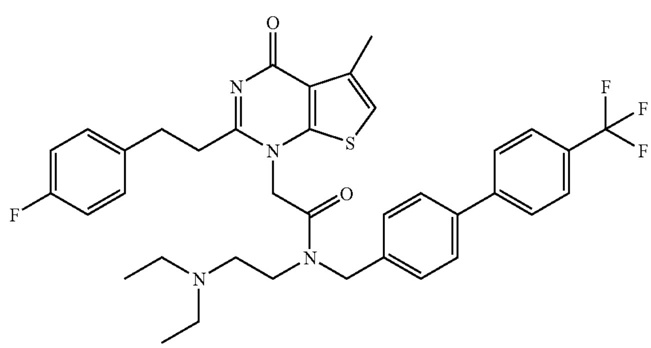 | N-(2-Diethylaminoethyl)-2-[2-(2-(4-fluorophenyl)ethyl)-5-methyl-4-oxo-4H-thieno[2,3-d]pyrimidin-1-yl]-N-(4'-trifluoromethylbiphenyl-4-ylmethyl)acetamide bitartrate |
| 51 | C40 + D4 | 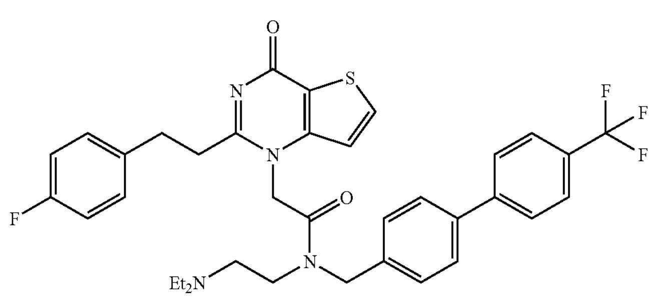 | N-(2-Diethylaminoethyl)-2-[2-(2-(4-fluorophenyl)ethyl)-4-oxo-4H-thieno[3,2-d]pyrimidin-1-yl]-N-(4'-trifluoromethylbiphenyl-4-ylmethyl)-acetamide bitartrate |

| No. | Precursors | Structure | Name |
|---|---|---|---|
| 52 | C44 + D4 | 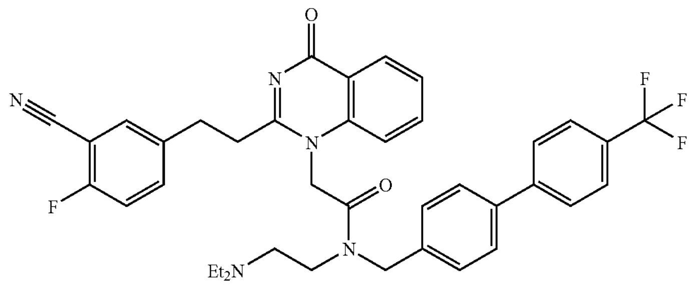 | N-(2-Diethylaminoethyl)-2-(2-(2-(3-cyano-4-fluorophenyl)-ethyl)-4-oxo-4H-quinazolin-1-yl)-N-(4'-trifluoro-methylbiphenyl-4-ylmethyl)acetamide bitartrate |
| 53 | C45 + D4 | 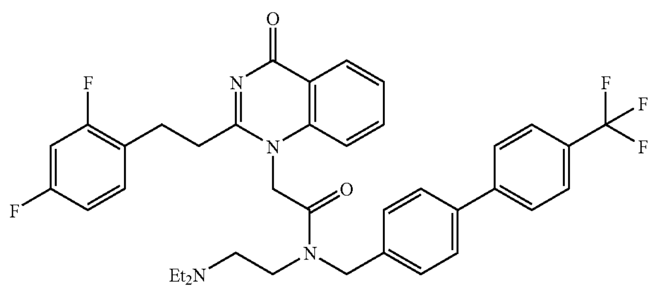 | N-(2-Diethylaminoethyl)-2-(2-(2-(2,4-difluorophenyl)-ethyl)-4-oxo-4H-quinazolin-1-yl)-N-(4'-trifluoro-methylbiphenyl-4-ylmethyl)acetamide bitartrate |
| 54 | C46 + D4 | 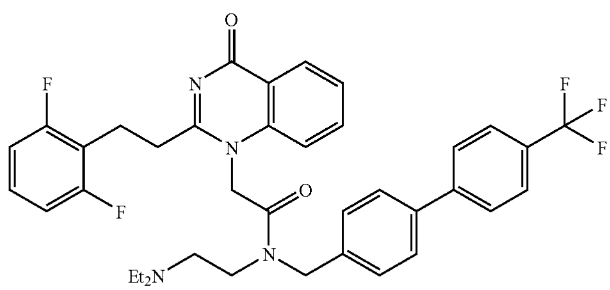 | N-(2-Diethylaminoethyl)-2-(2-(2-(2,6-difluorophenyl)-ethyl)-4-oxo-4H-quinazolin-1-yl)-N-(4'-trifluoro-methylbiphenyl-4-ylmethyl)acetamide bitartrate |
| 55 | C47 + D4 | 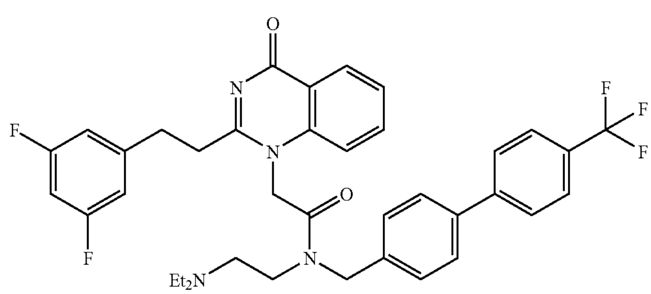 | N-(2-Diethylaminoethyl)-2-(2-(2-(3,5-difluorophenyl)-ethyl)-4-oxo-4H-quinazolin-1-yl)-N-(4'-trifluoro-methylbiphenyl-4-ylmethyl)acetamide bitartrate |
| 56 | C48 + D4 | 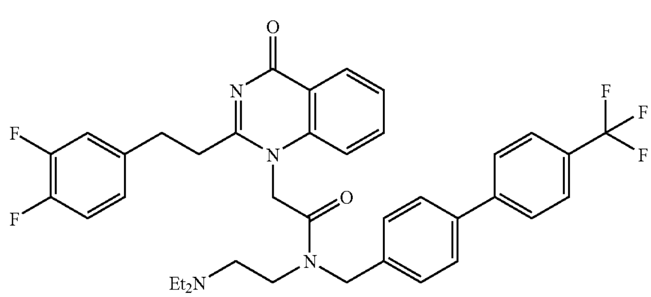 | N-(2-Diethylaminoethyl)-2-(2-(2-(3,4-difluorophenyl)-ethyl)-4-oxo-4H-quinazolin-1-yl)-N-(4'-trifluoro-methylbiphenyl-4-ylmethyl)acetamide bitartrate |

-continued

| No. | Precursors | Structure | Name |
|---|---|---|---|
| 57 | C49 + D4 | 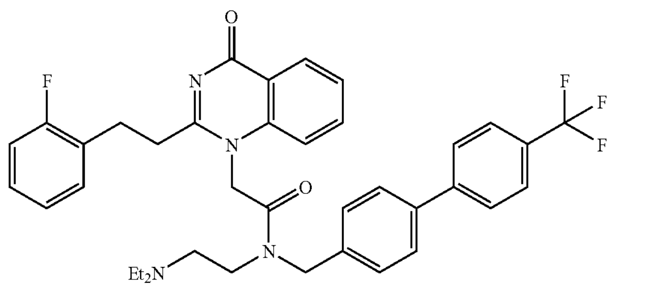 | N-(2-Diethylaminoethyl)-2-(2-(2-(2-difluorophenyl)-ethyl)-4-oxo-4H-quinazolin-1-yl)-N-(4'-trifluoro-methylbiphenyl-4-ylmethyl)acetamide bitartrate |
| 58 | C50 + D4 | 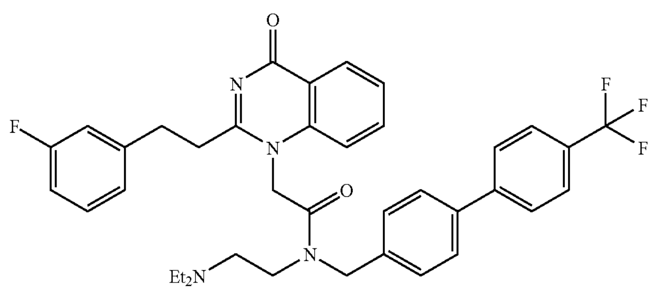 | N-(2-Diethylaminoethyl)-2-(2-(2-(3-fluorophenyl)-ethyl)-4-oxo-4H-quinazolin-1-yl)-N-(4'-trifluoro-methylbiphenyl-4-ylmethyl)acetamide bitartrate |
| 59 | C69 + D4 | 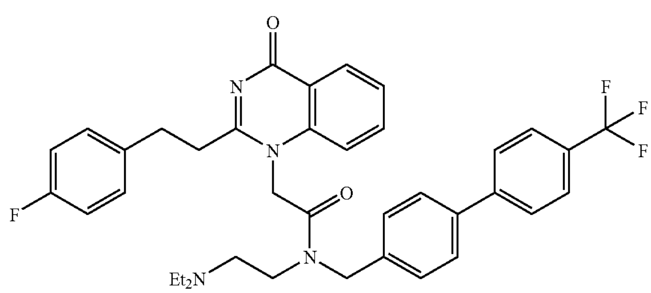 | N-(2-Diethylaminoethyl)-2-(2-(2-(4-fluorophenyl)-ethyl)-4-oxo-4H-quinazolin-1-yl)-N-(4'-trifluoro-methylbiphenyl-4-ylmethyl)acetamide bitartrate |
| 60 | C52 + D4 | 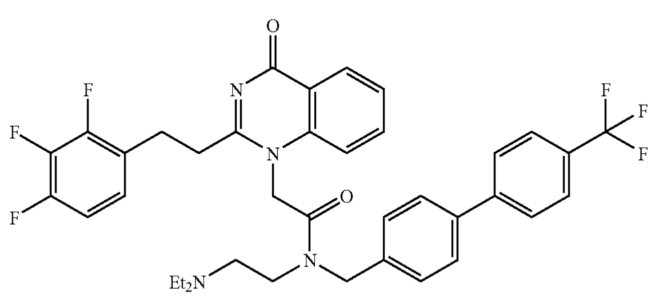 | N-(2-Diethylaminoethyl)-2-(2-(2-(2,3,4-trifluorophenyl)-ethyl)-4-oxo-4H-quinazolin-1-yl)-N-(4'-trifluoro-methylbiphenyl-4-ylmethyl)acetamide bitartrate |
| 61 | C53 + D4 | 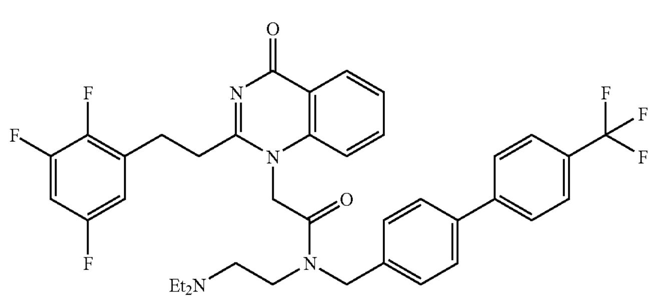 | N-(2-Diethylaminoethyl)-2-(2-(2-(2,3,5-trifluorophenyl)-ethyl)-4-oxo-4H-quinazolin-1-yl)-N-(4'-trifluoro-methylbiphenyl-4-ylmethyl)acetamide bitartrate |

| No. | Precursors | Structure | Name |
|---|---|---|---|
| 62 | C54 + D4 | 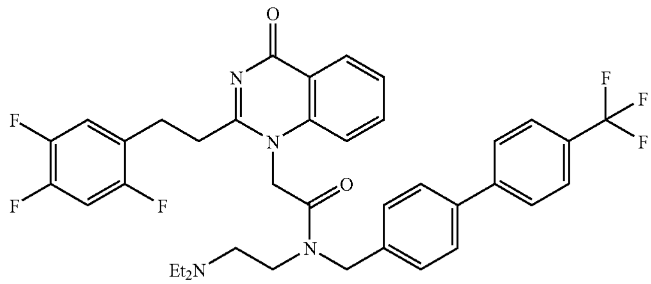 | N-(2-Diethylaminoethyl)-2-(2-(2-(2,4,5-trifluorophenyl)-ethyl)-4-oxo-4H-quinazolin-1-yl)-N-(4'-trifluoro-methylbiphenyl-4-ylmethyl)acetamide bitartrate |
| 63 | C55 + D4 | 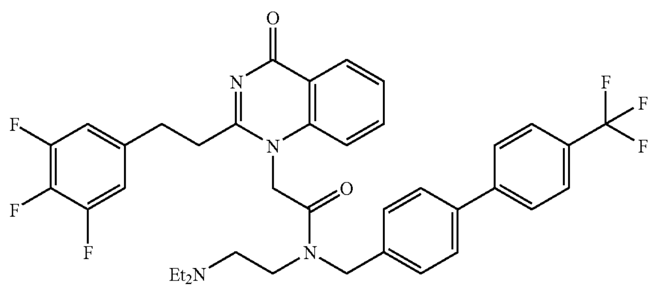 | N-(2-Diethylaminoethyl)-2-(2-(2-(3,4,5-trifluorophenyl)-ethyl)-4-oxo-4H-quinazolin-1-yl)-N-(4'-trifluoro-methylbiphenyl-4-ylmethyl)acetamide bitartrate |
| 64 | C56 + D4 | 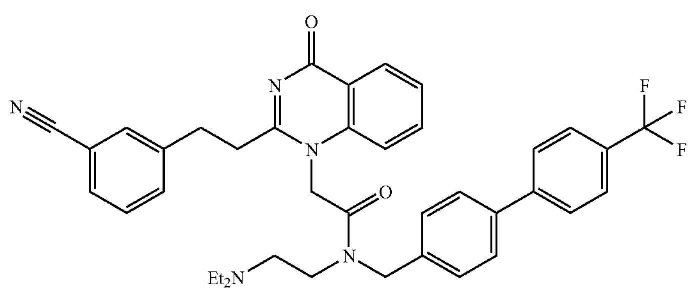 | N-(2-Diethylaminoethyl)-2-(2-(2-(3-cyanophenyl)-ethyl)-4-oxo-4H-quinazolin-1-yl)-N-(4'-trifluoro-methylbiphenyl-4-ylmethyl)acetamide bitartrate |
| 65 | C57 + D4 | 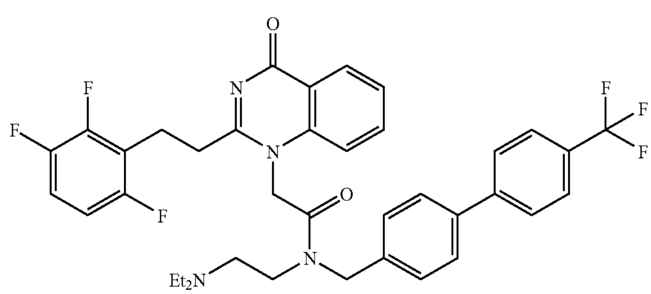 | N-(2-Diethylaminoethyl)-2-(2-(2-(2,3,6-trifluorophenyl)-ethyl)-4-oxo-4H-quinazolin-1-yl)-N-(4'-trifluoro-methylbiphenyl-4-ylmethyl)acetamide bitartrate |
| 66 | C58 + D4 | 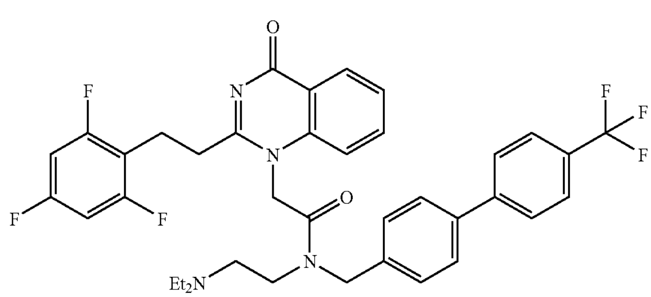 | N-(2-Diethylaminoethyl)-2-(2-(2-(2,4,6-trifluorophenyl)-ethyl)-4-oxo-4H-quinazolin-1-yl)-N-(4'-trifluoro-methylbiphenyl-4-ylmethyl)acetamide bitartrate |

-continued

| No. | Precursors | Structure | Name |
|---|---|---|---|
| 67 | C71 + D4 | 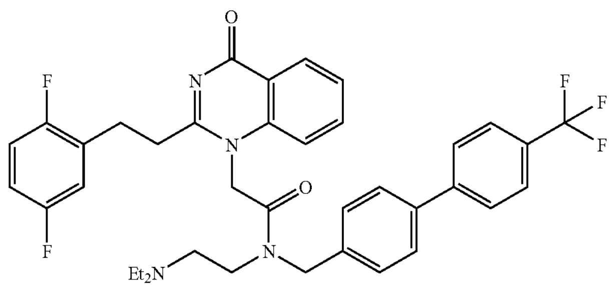 | N-(2-Diethylaminoethyl)-2-(2-(2-(2,5-difluorophenyl)-ethyl)-4-oxo-4H-quinazolin-1-yl)-N-(4'-trifluoro-methylbiphenyl-4-ylmethyl)acetamide bitartrate |
| 68 | C59 + D4 | 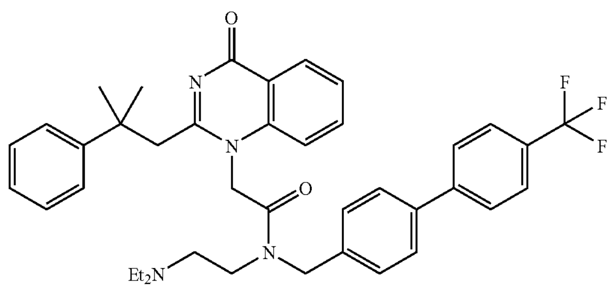 | N-(2-Diethylaminoethyl)-2-(2-(2-methyl-2-phenyl-propyl)-4-oxo-4H-quinazolin-1-yl)-N-(4'-trifluoro-methylbiphenyl-4-ylmethyl)acetamide bitartrate |
| 69 | C60 + D4 | 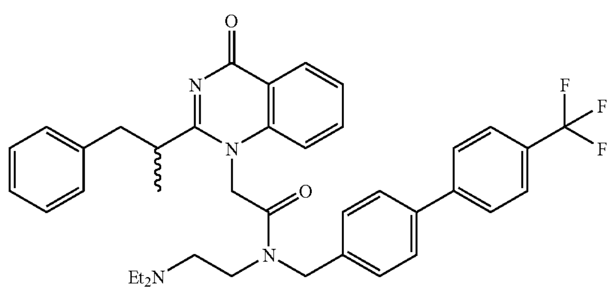 | (+/−)-N-(2-Diethylaminoethyl)-2-(2-(1-methyl-2-phenyl-ethyl)-4-oxo-4H-quinazolin-1-yl)-N-(4'-trifluoro-methylbiphenyl-4-ylmethyl)acetamide bitartrate |
| 70 | C70 + D4 | 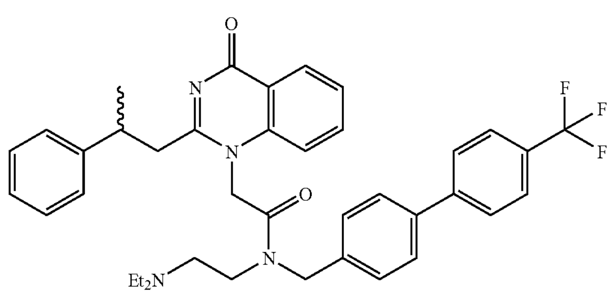 | (+/−)-N-(2-Diethylaminoethyl)-2-(2-(2-phenyl-propyl)-4-oxo-4H-quinazolin-1-yl)-N-(4'-trifluoro-methylbiphenyl-4-ylmethyl)acetamide bitartrate |
| 71 | C61 + D4 | 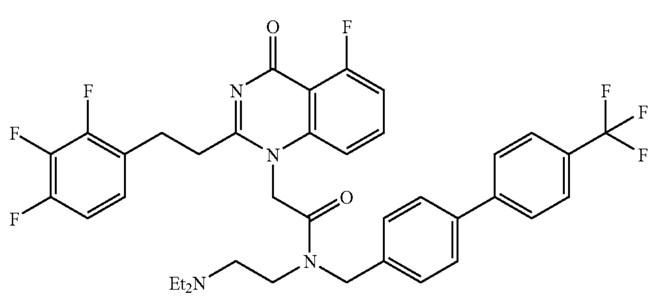 | N-(2-Diethylaminoethyl)-5-fluoro-2-(2-(2-(2,3,4-trifluorophenyl)-ethyl)-4-oxo-4H-quinazolin-1-yl)-N-(4'-trifluoromethyl-biphenyl-4-ylmethyl)-acetamide bitartrate |

-continued

| No. | Precursors | Structure | Name |
|---|---|---|---|
| 72 | C62 + D4 | 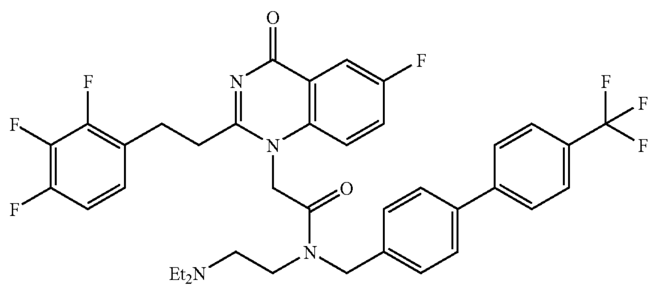 | N-(2-Diethylaminoethyl)-6-fluoro-2-(2-(2-(2,3,4-trifluorophenyl)-ethyl)-4-oxo-4H-quinazolin-1-yl)-N-(4'-trifluoromethyl-biphenyl-4-ylmethyl)-acetamide bitartrate |
| 73 | C63 + D4 | 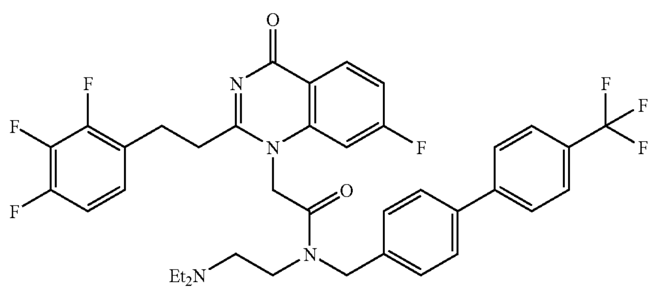 | N-(2-Diethylaminoethyl)-7-fluoro-2-(2-(2-(2,3,4-trifluorophenyl)-ethyl)-4-oxo-4H-quinazolin-1-yl)-N-(4'-trifluoromethyl-biphenyl-4-ylmethyl)-acetamide bitartrate |
| 74 | C64 + D4 | 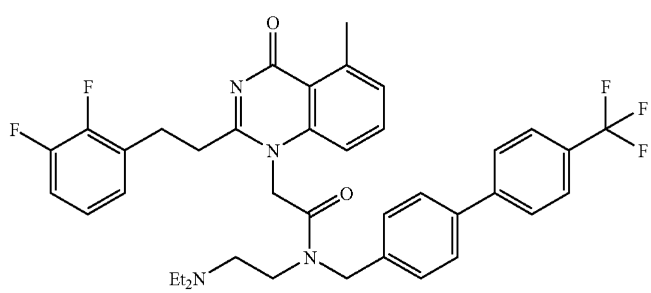 | N-(2-Diethylaminoethyl)-2-(2-(2-(2,3-difluorophenyl)-ethyl)-5-methyl-4-oxo-4H-quinazolin-1-yl)-N-(4'-trifluoromethyl-biphenyl-4-ylmethyl)-acetamide bitartrate |
| 75 | C65 + D4 | 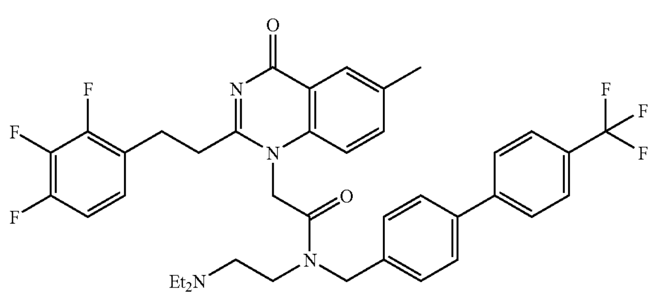 | N-(2-Diethylaminoethyl)-2-(2-2-2,3-difluorophenyl)-ethyl)-6-methyl-4-oxo-4H-quinazolin-1-yl)-N-(4'-trifluoromethyl-biphenyl-4-ylmethyl)-acetamide bitartrate |
| 76 | C66 + D4 | 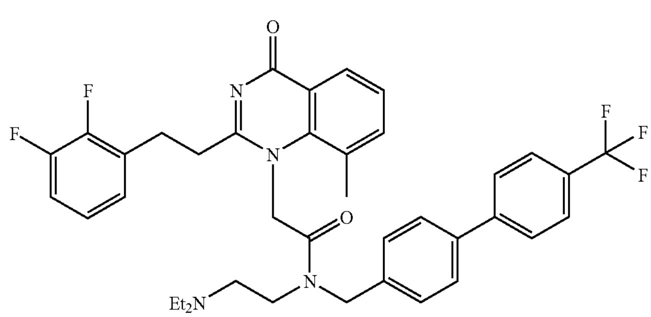 | N-(2-Diethylaminoethyl)-2-(2-(2-(2,3-difluorophenyl)-ethyl)-8-methyl-4-oxo-4H-quinazolin-1-yl)-N-(4'-trifluoromethyl-biphenyl-4-ylmethyl)-acetamide |

-continued

| No. | Precursors | Structure | Name |
|---|---|---|---|
| 77 | C67 + D4 | 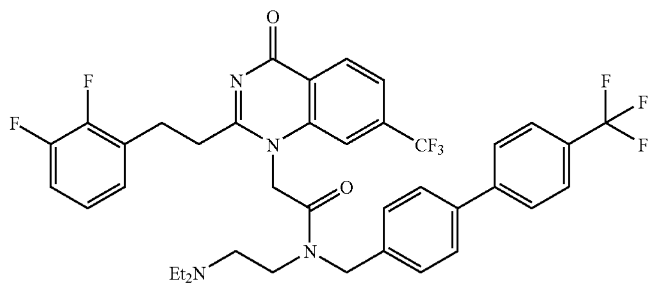 | N-(2-Diethylaminoethyl)-2-(2-(2-(2,3-difluorophenyl)-ethyl)-7-trifluoro-methyl-4-oxo-4H-quinazolin-1-yl)-N-(4'-trifluoromethyl-biphenyl-4-ylmethyl)acetamide bitartrate |
| 78 | C68 + D4 | 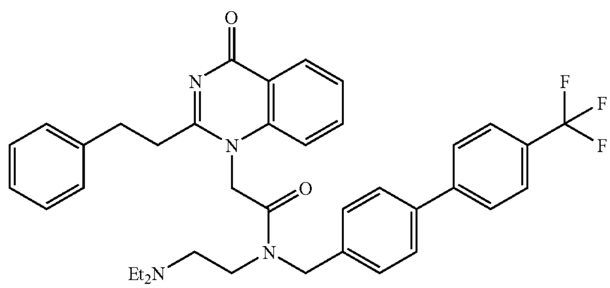 | N-(2-Diethylaminoethyl)-2-(2-(2-phenylethyl)-4-oxo-4H-quinazolin-1-yl)-N-(4'-trifluoromethyl-biphenyl-4-ylmethyl)acetamide bitartrate |
| 79 | C43 + D4 | 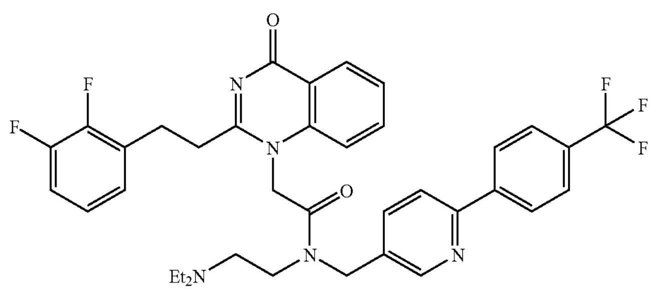 | N-(2-Diethylaminoethyl)-2-(2-(2-(2,3-difluorophenyl)-ethyl)-4-oxo-4H-quinazolin-1-yl)-N-(2-(4'-trifluoromethylphenyl)pyrid-5-yl-methyl)acetamide bitartrate |
| 80 | C43 + D3 | 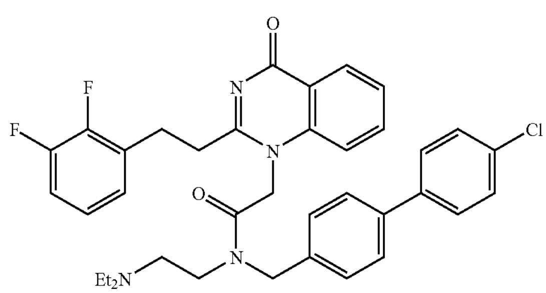 | N-(2-Diethylaminoethyl)-2-(2-(2-(2,3-difluorophenyl)-ethyl)-4-oxo-4H-quinazolin-1-yl)-N-(4'-chloro-biphenyl-4-ylmethyl)acetamide bitartrate |
| 81 | C43 + D32 | 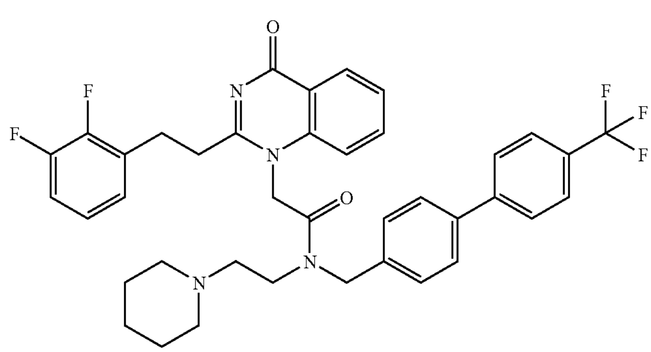 | N-(2-piperidin-1-ylethyl)-2-(2-(2-(2,3-difluorophenyl)-ethyl)-4-oxo-4H-quinazolin-1-yl)-N-(4'-trifluoro-biphenyl-4-ylmethyl)acetamide bitartrate |

| No. | Precursors | Structure | Name |
|---|---|---|---|
| 82 | C43 + D33 | 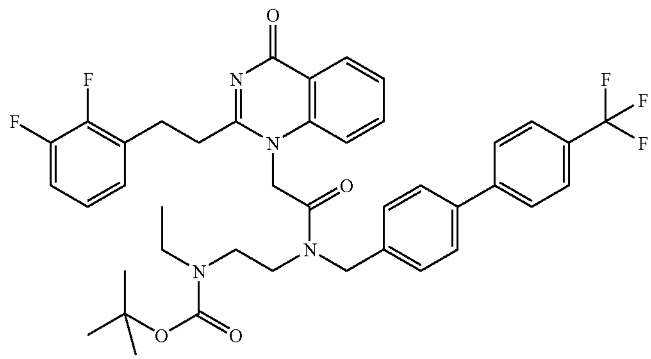 | N-(2-(N'-ethyl-t-butoxycarbonyl-amino)ethyl)-2-(2-(2-(2,3-difluoro-phenyl)ethyl)-4-oxo-4H-quinazolin-1-yl)-N-(4'-trifluoromethyl-biphenyl-4-ylmethyl)acetamide |
| 83 | C43 + D34 | 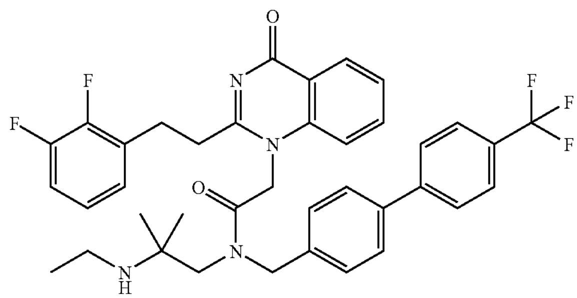 | N-(2-Ethylamino-2-methylpropyl)-2-(2-(2-(2,3-difluorophenyl)-ethyl)-4-oxo-4H-quinazolin-1-yl)-N-(4'-trifluoromethylbiphenyl-4-ylmethyl)-acetamide bitartrate |
| 84 | C43 + D35 | 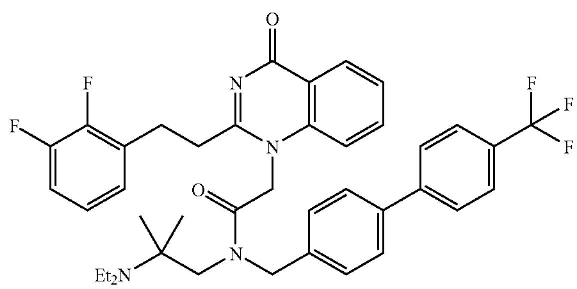 | N-(2-(Diethylamino)-2-methyl-propyl)-2-(2-(2-(2,3-difluorophenyl)-ethyl)-4-oxo-4H-quinazolin-1-yl)-N-(4'-trifluoromethyl-biphenyl-4-ylmethyl)acetamide bitartrate |
| 85 | C43 + D36 | 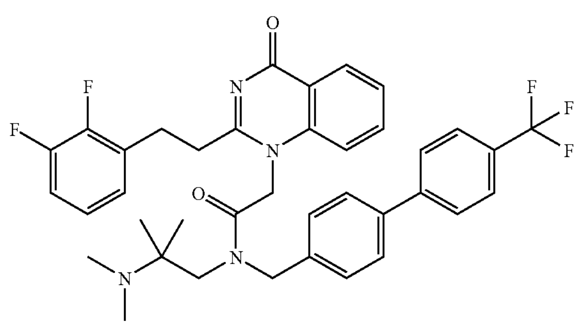 | N-(2-(Dimethylamino)-2-methyl-propyl)-2-(2-(2-(2,3-difluorophenyl)-ethyl)-4-oxo-4H-quinazolin-1-yl)-N-(4'-trifluoromethyl-biphenyl-4-yl-methyl)acetamide bitartrate |
| 86 | C43 + D37 | 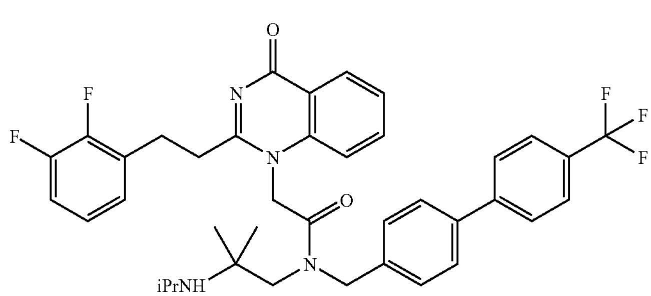 | N-(2-isopropylamino)-2-methyl-propyl)-2-(2-(2-(2,3-difluorophenyl)-ethyl)-4-oxo-4H-quinazolin-1-yl)-N-(4'-trifluoromethyl-biphenyl-4-ylmethyl)acetamide |

-continued

| No. | Precursors | Structure | Name |
|---|---|---|---|
| 87 | C43 + D38 | 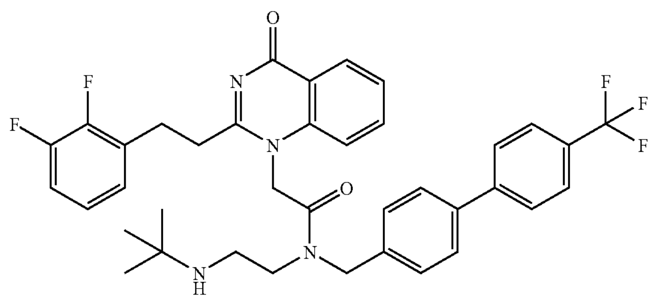 | N-(2-(t-butylamino)-ethyl)-2-(2-(2-(2,3-difluorophenyl)-ethyl)-4-oxo-4H-quinazolin-1-yl)-N-(4'-trifluoromethylbiphenyl-4-ylmethyl)acetamide |
| 88 | C43 + D39 | 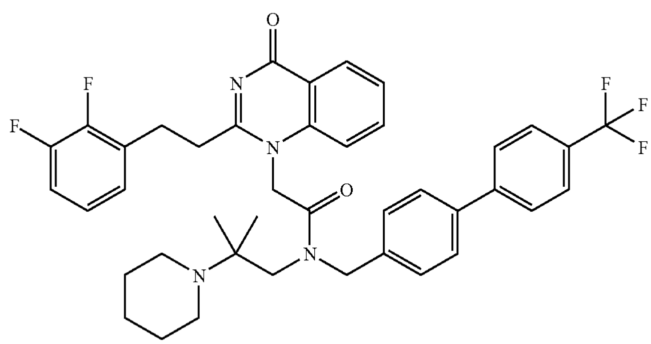 | N-(2-(piperidin-1-yl)-2-methyl-propyl)-2-(2-(2-(2,3-difluorophenyl)-ethyl)-4-oxo-4H-quinazolin-1-yl)-N-(4'-trifluoromethyl-biphenyl-4-yl-methyl)acetamide |
| 89 | C43 + D40 | 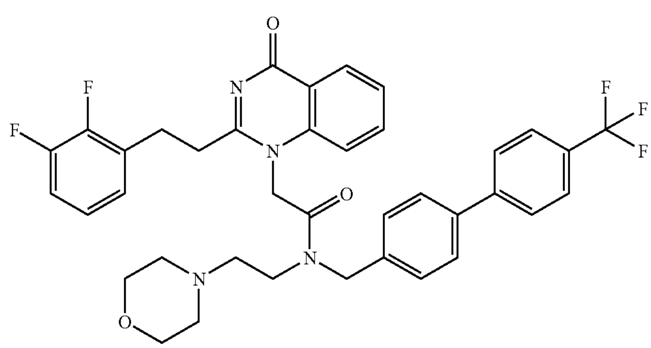 | N-(2-(morpholin-4-yl)-ethyl)-2-(2-(2-(2,3-difluorophenyl)-ethyl)-4-oxo-4H-quinazolin-1-yl)-N-(4'-trifluoromethylbiphenyl-4-ylmethyl)acetamide bitartrate |
| 90 | C43 + D41 | 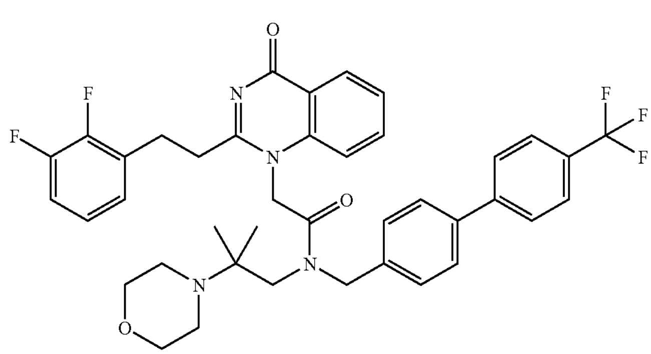 | N-(2-(morpholin-4-yl)-2-methyl-propyl)-2-(2-(2-(2,3-difluorophenyl)-ethyl)-4-oxo-4H-quinazolin-1-yl)-N-(4'-trifluoromethyl-biphenyl-4-yl-methyl)acetamide bitartrate |

| No. | Precursors | Structure | Name |
|---|---|---|---|
| 91 | C43 + D42 | 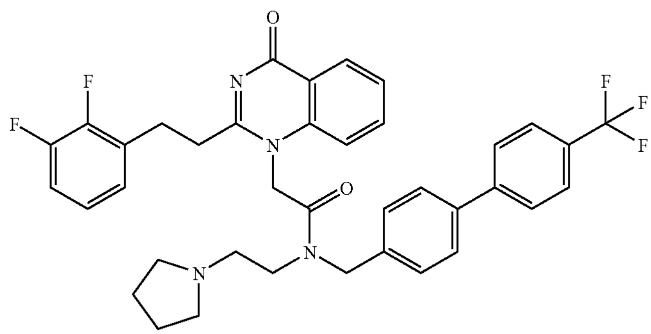 | N-(2-(pyrrolidin-1-yl)-ethyl)-2-(2-(2-(2,3-difluorophenyl)-ethyl)-4-oxo-4H-quinazolin-1-yl)-N-(4'-trifluoro-methylbiphenyl-4-ylmethyl)acetamide |
| 92 | C43 + D43 | 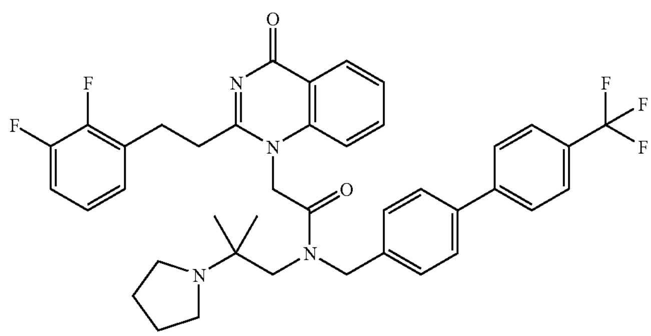 | N-(2-(pyrrolidin-1-yl)-2-methyl-propyl)-2-(2-(2-(2,3-difluorophenyl)-ethyl)-4-oxo-4H-quinazolin-1-yl)-N-(4'-trifluoromethyl-biphenyl-4-yl-methyl)acetamide |
| 93 | C43 + D44 | 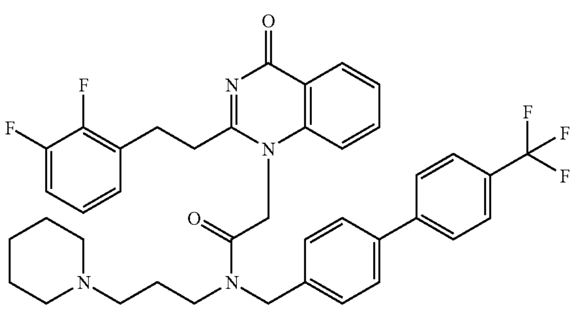 | N-(3-(piperidin-1-yl)-propyl)-2-(2-(2-(2,3-difluorophenyl)-ethyl)-4-oxo-4H-quinazolin-1-yl)-N-(4'-trifluoro-methylbiphenyl-4-ylmethyl)acetamide bitartrate |
| 94 | C43 + D45 | 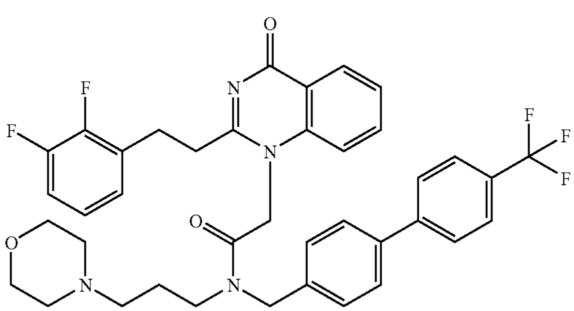 | N-(3-(morpholin-4-yl)-propyl)-2-(2-(2-(2,3-difluorophenyl)-ethyl)-4-oxo-4H-quinazolin-1-yl)-N-(4'-trifluoro-methylbiphenyl-4-ylmethyl)acetamide bitartrate |
| 95 | C43 + D46 | 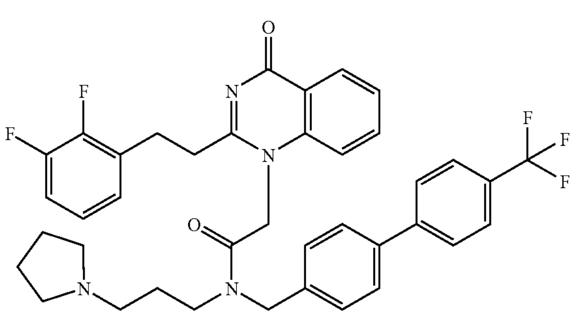 | N-(3-(pyrrolidin-1-yl)-propyl)-2-(2-(2-(2,3-difluorophenyl)-ethyl)-4-oxo-4H-quinazolin-1-yl)-N-(4'-trifluoro-methylbiphenyl-4-ylmethyl)acetamide bitartrate |

| No. | Precursors | Structure | Name |
|---|---|---|---|
| 96 | C43 + D47 | 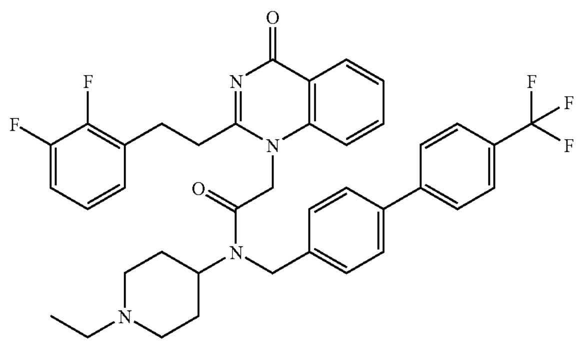 | N-(1-Ethyl-piperidin-4-yl)-2-(2-(2-(2,3-difluorophenyl)-ethyl)-4-oxo-4H-quinazolin-1-yl)-N-(4'-trifluoro-methylbiphenyl-4-ylmethyl)acetamide bitartrate |
| 97 | C43 + D48 | 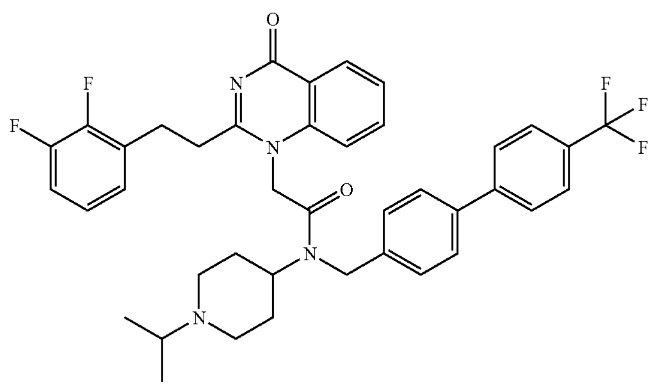 | N-(1-isopropyl-piperidin-4-yl)-2-(2-(2-(2,3-difluorophenyl)-ethyl)-4-oxo-4H-quinazolin-1-yl)-N-(4'-trifluoro-methylbiphenyl-4-ylmethyl)acetamide bitartrate |
| 98 | C43 + D49 | 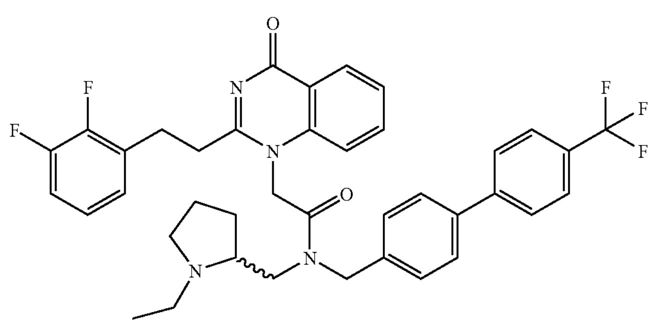 | (+/−)-N-(1-ethyl-pyrrolidin-2-yl-methyl)-2-(2-(2-(2,3-difluorophenyl)-ethyl)-4-oxo-4H-quinazolin-1-yl)-N-(4'-trifluoromethyl-biphenyl-4-yl-methyl)acetamide bitartrate |
| 99 | C43 + D50 | 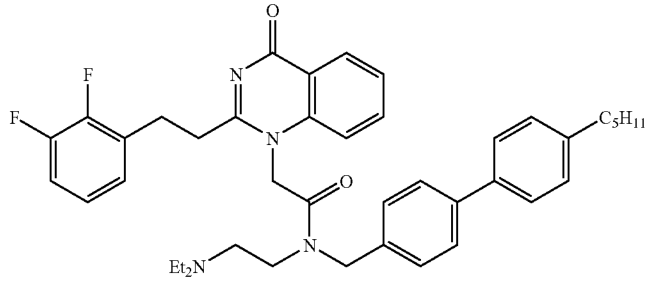 | N-(2-(diethylamino)ethyl)-2-(2-(2-(2,3-difluorophenyl)-ethyl)-4-oxo-4H-quinazolin-1-yl)-N-(4'-pent-1-yl-biphenyl-4-ylmethyl)acetamide bitartrate |

| No. | Precursors | Structure | Name |
|---|---|---|---|
| 100 | C43 + D51 | 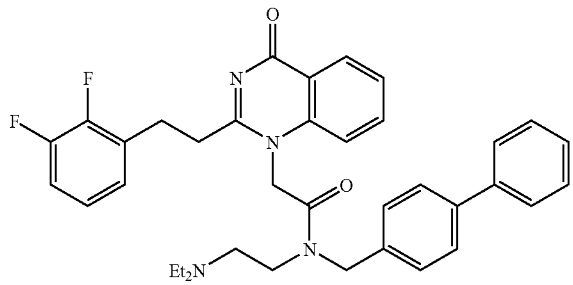 | N-(2-(diethylamino)ethyl)-2-(2-(2-(2,3-difluorophenyl)-ethyl)-4-oxo-4H-quinazolin-1-yl)-N-(biphenyl-4-ylmethyl)acetamide bitartrate |
| 101 | C43 + D53 | 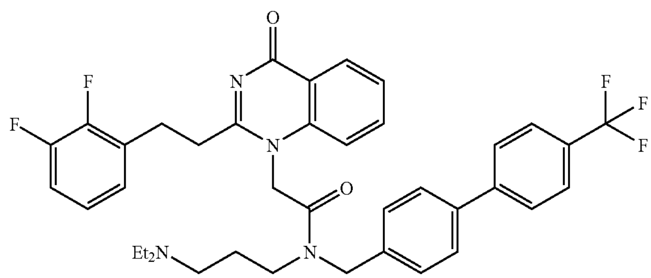 | N-(3-(diethylamino)propyl)-2-(2-(2-(2,3-difluorophenyl)-ethyl)-4-oxo-4H-quinazolin-1-yl)-N-(4'-trifluoro-methylbiphenyl-4-ylmethyl)acetamide bitartrate |
| 102 | C43 + D54 | 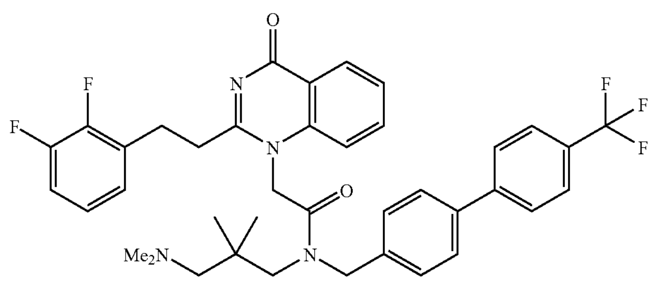 | N-(2,2-dimethyl-3-(dimethylamino)-propyl)-2-(2-(2-(2,3-difluorophenyl)-ethyl)-4-oxo-4H-quinazolin-1-yl)-N-(4'-trifluoromethyl-biphenyl-4-yl-methyl)acetamide |
| 103 | C68 + D4 | 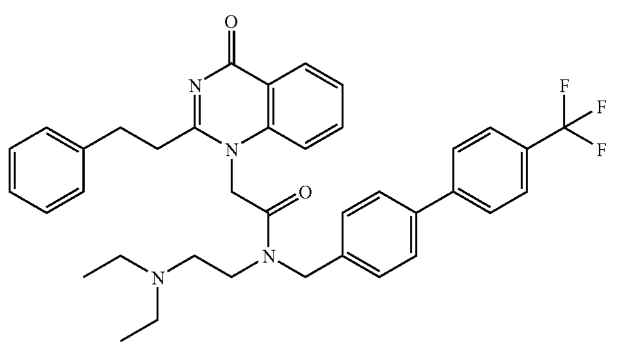 | N-(2-diethylaminoethyl)-2-(2-(2-phenylethyl)-4-oxo-4H-quinazolin-1-yl)-N-(4'-trifluoromethyl-biphenyl-4-ylmethyl)acetamide bitartrate |
| 105 | C75 + D4 | 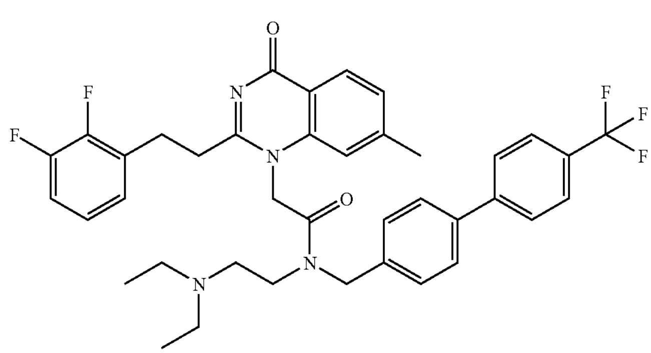 | N-(2-diethylaminoethyl)-2-(2-(2-(2,3-difluorophenyl)-ethyl)-7-methyl-4-oxo-4H-quinazolin-1-yl)-N-(4'-trifluoromethyl-biphenyl-4-ylmethyl)-acetamide bitartrate |

-continued

| No. | Precursors | Structure | Name |
|---|---|---|---|
| 106 | C76 + D4 | 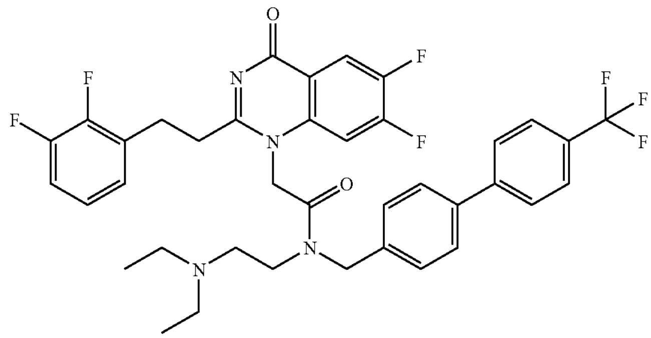 | N-(2-diethylaminoethyl)-2-(2-(2-(2,3-difluorophenyl)-ethyl)-6,7-difluoro-4-oxo-4H-quinazolin-1-yl)-N-(4'-trifluoromethyl-biphenyl-4-ylmethyl)-acetamide bitartrate |
| 107 | C77 + D4 | 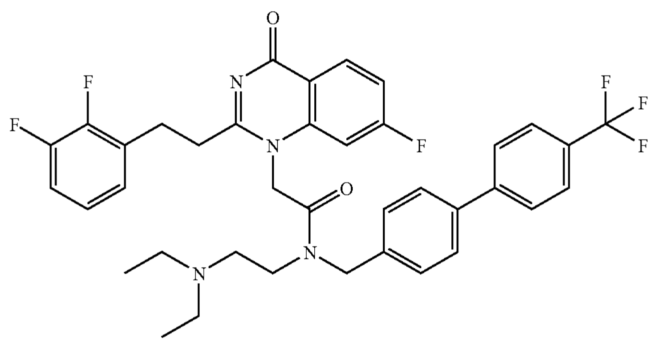 | N-(2-diethylaminoethyl)-2-(2-(2-(2,3-difluorophenyl)-ethyl)-7-fluoro-4-oxo-4H-quinazolin-1-yl)-N-(4'-trifluoromethyl-biphenyl-4-ylmethyl)-acetamide bitartrate |
| 108 | C78 + D4 | 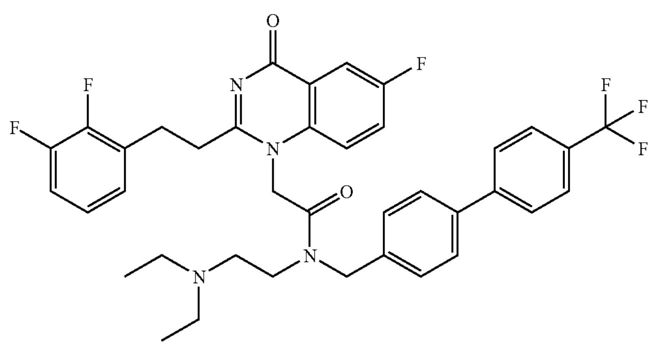 | N-(2-diethylaminoethyl)-2-(2-(2-(2,3-difluorophenyl)-ethyl)-6-fluoro-4-oxo-4H-quinazolin-1-yl)-N-(4'-trifluoromethyl-biphenyl-4-ylmethyl)-acetamide bitartrate |
| 109 | C35 + D47 | 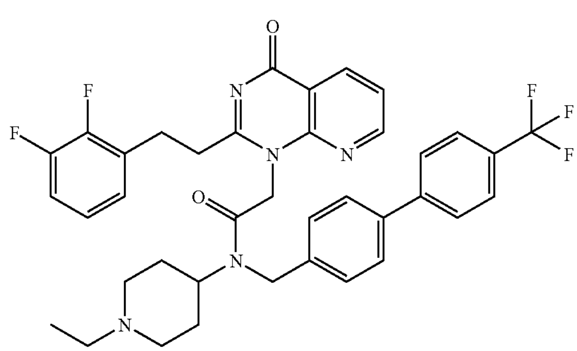 | N-(1-ethylpiperidin-4-yl)-2-(2-(2-(2,3-difluorophenyl)-ethyl)-4-oxo-4H-pyrido[2,3-d]pyrimidin-1-yl)-N-(4'-trifluoromethyl-biphenyl-4-yl-methyl)acetamide bitartrate |

-continued

| No. | Precursors | Structure | Name |
|---|---|---|---|
| 110 | C80 + D47 | 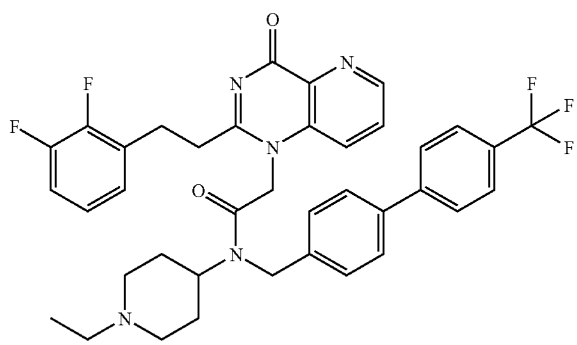 | N-(1-ethylpiperidin-4-yl)-2-(2-(2-(2,3-difluorophenyl)-ethyl)-4-oxo-4H-pyrido[3,2-d]pyrimidin-1-yl)-N-(4'-trifluoromethyl-biphenyl-4-yl-methyl)acetamide bitartrate |
| 111 | C43 + D80 | 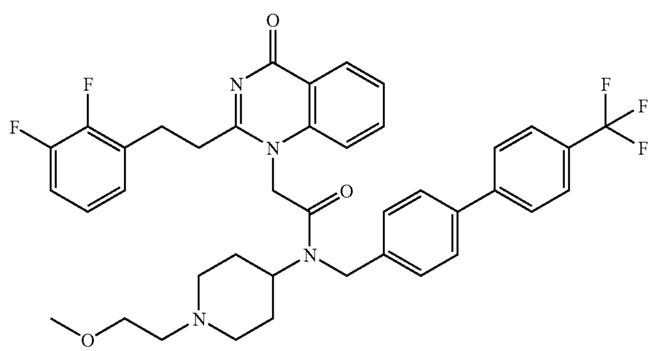 | N-(1-(2-methoxyethyl)piperidin-4-yl)-2-(2-(2-(2,3-difluorophenyl)-ethyl)-4-oxo-4H-quinazolin-1-yl)-N-(4'-trifluoromethyl-biphenyl-4-yl-methyl)acetamide bitartrate |
| 112 | C43 + D97 | 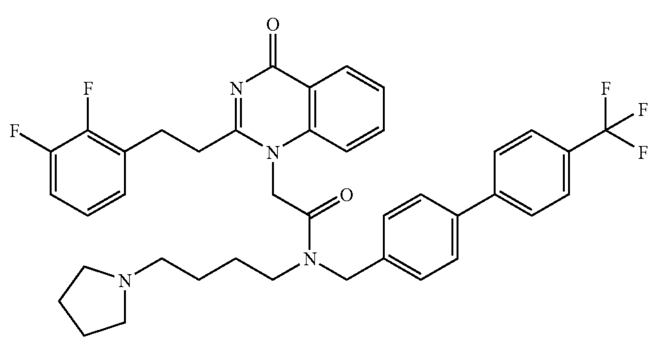 | N-(4-(pyrrolidin-1-yl)butyl)-2-(2-(2-(2,3-difluorophenyl)-ethyl)-4-oxo-4H-quinazolin-1-yl)-N-(4'-trifluoro-methylbiphenyl-4-ylmethyl)acetamide bitartrate |
| 113 | C43 + D5 | 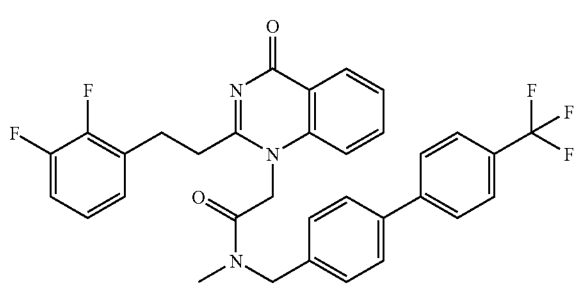 | N-methyl-2-(2-(2-(2,3-difluoro-phenyl)ethyl)-4-oxo-4H-quinazolin-1-yl)-N-(4'-trifluoromethyl-biphenyl-4-ylmethyl)acetamide |
| 114 | C43 + D78 | 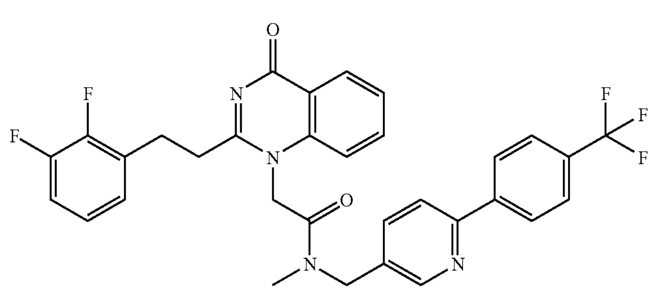 | N-methyl-2-(2-(2-(2,3-difluoro-phenyl)ethyl)-4-oxo-4H-quinazolin-1-yl)-N-(5-(4-trifluoromethylphenyl-pyrid-2-ylmethyl)acetamide |

| No. | Precursors | Structure | Name |
|---|---|---|---|
| 115 | C43 + D67 | 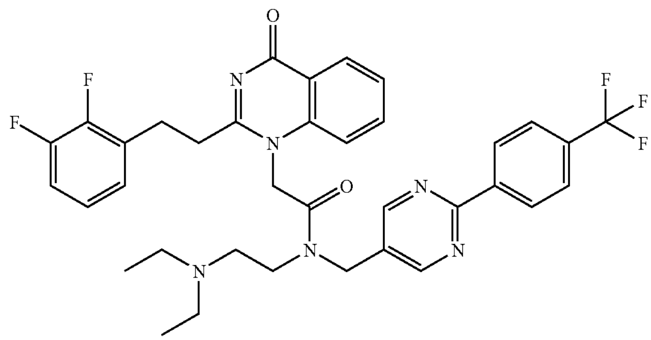 | N-(2-diethylaminoethyl)-2-(2-(2-(2,3-difluorophenyl)-ethyl)-4-oxo-4H-quinazolin-1-yl)-N-(2-(4-trifluoromethylphenyl)pyrimid-5-ylmethyl)-acetamide bitartrate |
| 116 | C43 + D55 | 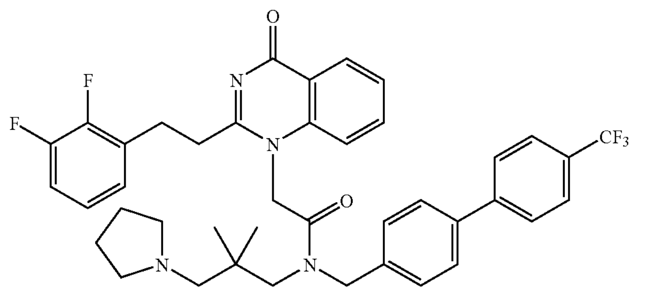 | N-(3-(pyrrolidin-1-yl)-2,2-dimethyl-propyl)-2-(2-(2-(2,3-difluorophenyl)-ethyl)-4-oxo-4H-quinazolin-1-yl)-N-(4'-trifluoromethyl-biphenyl-4-yl-methyl)acetamide bitartrate |
| 117 | C43 + D56 | 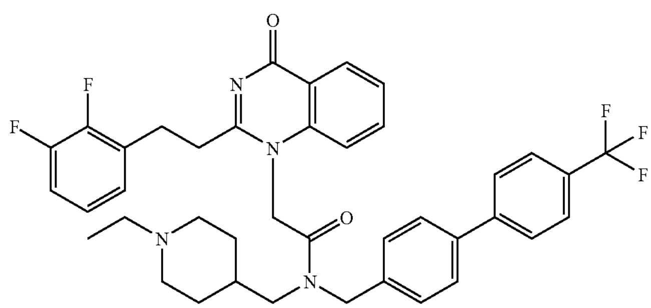 | N-(1-ethylpiperidin-4-ylmethyl)-2-(2-(2-(2,3-difluorophenyl)-ethyl)-4-oxo-4H-quinazolin-1-yl)-N-(4'-trifluoromethylbiphenyl-4-ylmethyl)acetamide bitartrate |
| 118 | C43 + D57 | 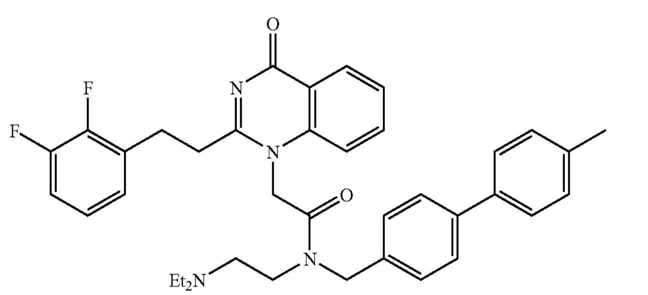 | N-(2-diethylaminoethyl)-2-(2-(2-(2,3-difluorophenyl)-ethyl)-4-oxo-4H-quinazolin-1-yl)-N-(4'-methyl-biphenyl-4-ylmethyl)acetamide bitartrate |
| 119 | C43 + D58 | 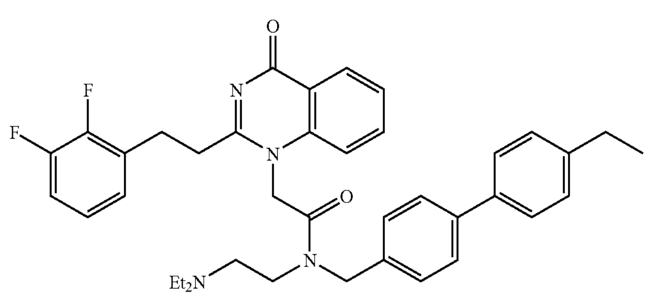 | N-(2-diethylaminoethyl)-2-(2-(2-(2,3-difluorophenyl)-ethyl)-4-oxo-4H-quinazolin-1-yl)-N-(4'-ethyl-biphenyl-4-ylmethyl)acetamide bitartrate |

| No. | Precursors | Structure | Name |
|---|---|---|---|
| 120 | C43 + D59 | 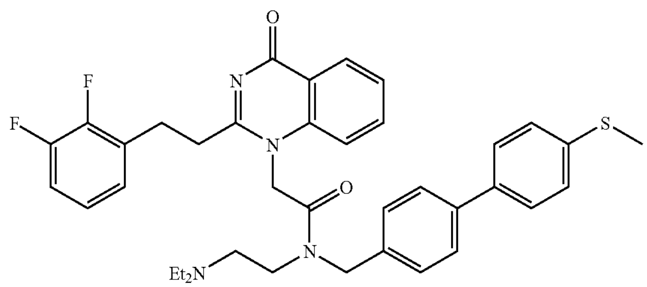 | N-(2-diethylaminoethyl)-2-(2-(2-(2,3-difluorophenyl)-ethyl)-4-oxo-4H-quinazolin-1-yl)-N-(4'-methylthio-biphenyl-4-ylmethyl)acetamide bitartrate |
| 121 | C43 + D60 | 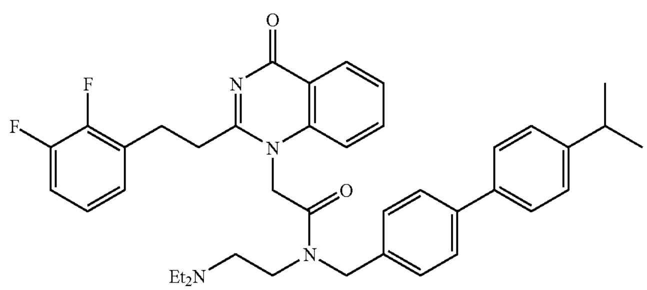 | N-(2-diethylaminoethyl)-2-(2-(2-(2,3-difluorophenyl)-ethyl)-4-oxo-4H-quinazolin-1-yl)-N-(4'-(prop-2-yl)-biphenyl-4-ylmethyl)acetamide bitartrate |
| 122 | C43 + D61 | 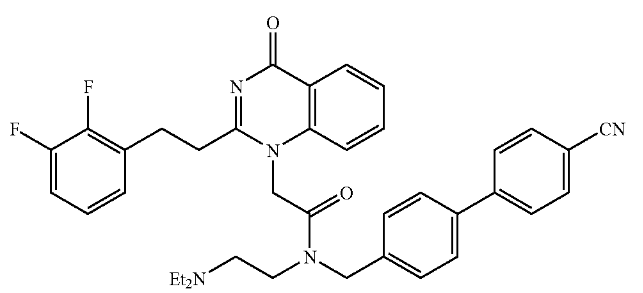 | N-(2-diethylaminoethyl)-2-(2-(2-(2,3-difluorophenyl)-ethyl)-4-oxo-4H-quinazolin-1-yl)-N-(4'-cyano-biphenyl-4-ylmethyl)acetamide bitartrate |
| 123 | C43 + D62 | 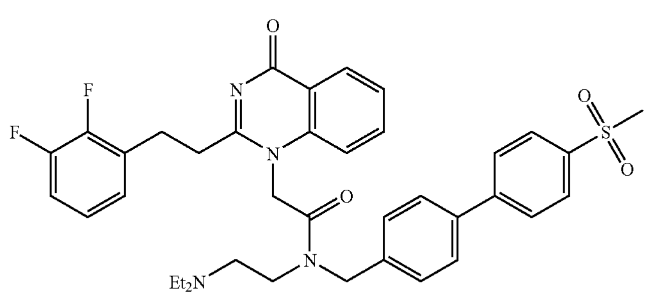 | N-(2-diethylaminoethyl)-2-(2-(2-(2,3-difluorophenyl)-ethyl)-4-oxo-4H-quinazolin-1-yl)-N-(4'-methyl-sulfonyl-biphenyl-4-ylmethyl)-acetamide bitartrate |
| 124 | C43 + D64 | 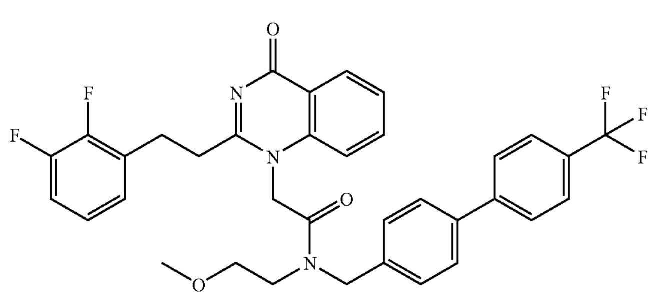 | N-(2-methoxyethyl)-2-(2-(2-(2,3-difluorophenyl)-ethyl)-4-oxo-4H-quinazolin-1-yl)-N-(4'-trifluoro-methyl-biphenyl-4-ylmethyl)-acetamide |

-continued

| No. | Precursors | Structure | Name |
|---|---|---|---|
| 125 | C43 + D68 | 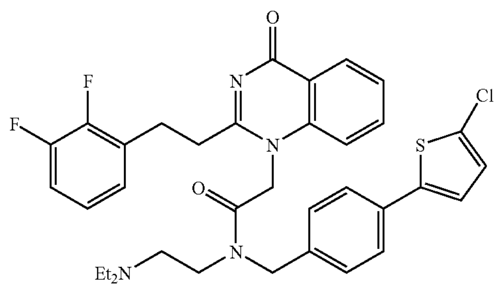 | N-(2-diethylaminoethyl)-2-(2-(2-(2,3-difluorophenyl)-ethyl)-4-oxo-4H-quinazolin-1-yl)-N-(4-(2-chlorothien-5-yl)phenylmethyl)acetamide bitartrate |
| 126 | C43 + D81 | 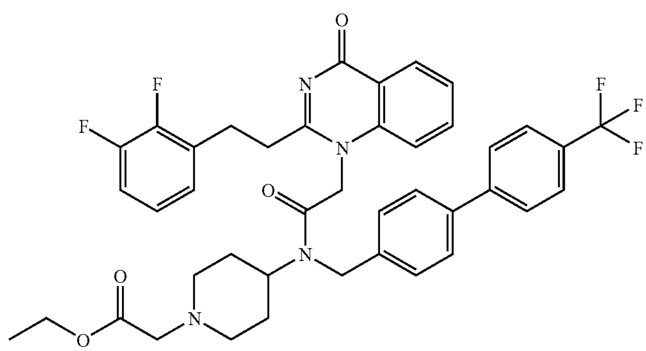 | N-(1-ethoxycarbonylmethylpiperidin-4-yl)-2-(2-(2-(2,3-difluorophenyl)-ethyl)-4-oxo-4H-quinazolin-1-yl)-N-(4'-trifluoromethyl-biphenyl-4-yl-methyl)acetamide bitartrate |
| 127 | C43 + D65 | 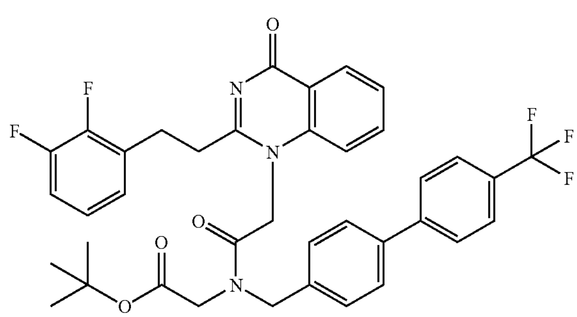 | N-(t-butoxycarbonylmethyl)-2-(2-(2-(2,3-difluorophenyl)-ethyl)-4-oxo-4H-quinazolin-1-yl)-N-(4'-trifluoro-methyl-biphenyl-4-ylmethyl)acetamide |
| 128 | C43 + D69 | 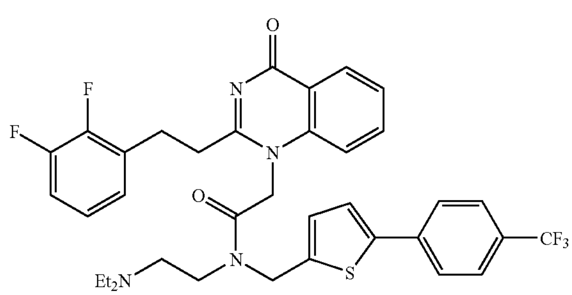 | N-(2-diethylaminoethyl)-2-(2-(2-(2,3-difluorophenyl)-ethyl)-4-oxo-4H-quinazolin-1-yl)-N-(2-(4-trifluoromethylphenyl)thien-5-ylmethyl)-acetamide bitartrate |
| 129 | C43 + D70 | 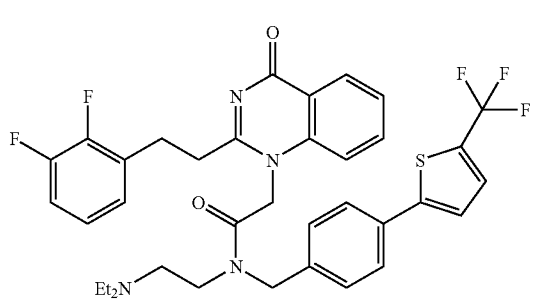 | N-(2-diethylaminoethyl)-2-(2-(2-(2,3-difluorophenyl)-ethyl)-4-oxo-4H-quinazolin-1-yl)-N-(4-(2-trifluoromethylthien-5-yl)phenylmethyl)-acetamide bitartrate |

-continued

| No. | Precursors | Structure | Name |
|---|---|---|---|
| 130 | C43 + D72 | 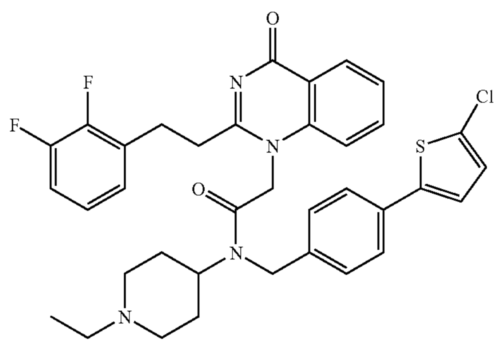 | N-(1-ethylpiperidin-4-yl)-2-(2-(2-(2,3-difluorophenyl)-ethyl)-4-oxo-4H-quinazolin-1-yl)-N-(4-(2-chlorothien-5-yl)phenylmethyl)-acetamide bitartrate |
| 131 | C43 + D73 | 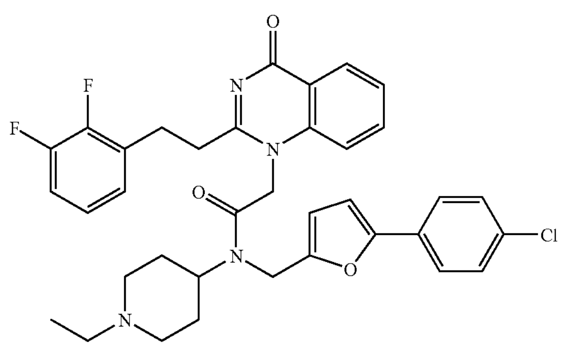 | N-(1-ethylpiperidin-4-yl)-2-(2-(2-(2,3-difluorophenyl)-ethyl)-4-oxo-4H-quinazolin-1-yl)-N-(2-(4-chlorophenyl)-fur-5-ylmethyl)-acetamide bitartrate |
| 132 | C43 + D74 | 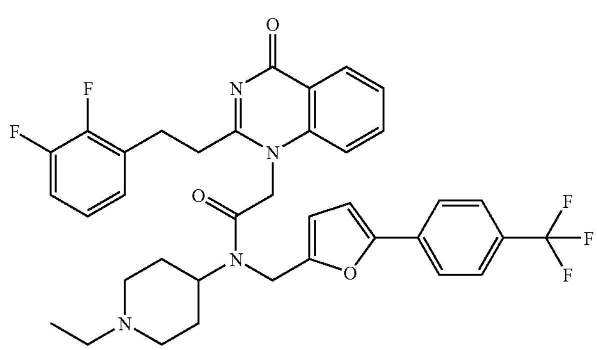 | N-(1-ethylpiperidin-4-yl)-2-(2-(2-(2,3-difluorophenyl)-ethyl)-4-oxo-4H-quinazolin-1-yl)-N-(2-(4-trifluoromethylphenyl)fur-5-yl-methyl)acetamide bitartrate |
| 133 | C43 + D63 | 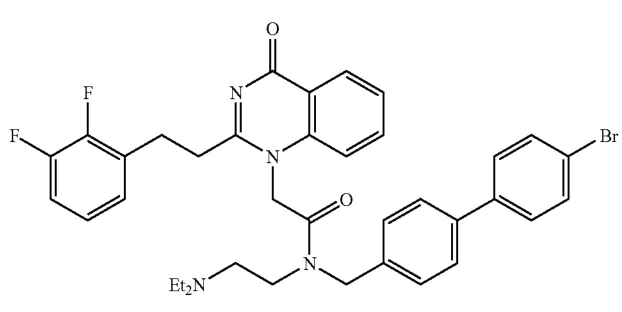 | N-(2-diethylaminoethyl)-2-(2-(2-(2,3-difluorophenyl)-ethyl)-4-oxo-4H-quinazolin-1-yl)-N-(4'-bromo-biphenyl-4-ylmethyl)acetamide bitartrate |

-continued

| No. | Precursors | Structure | Name |
|-----|------------|-----------|------|
| 134 | C43 + D75 | 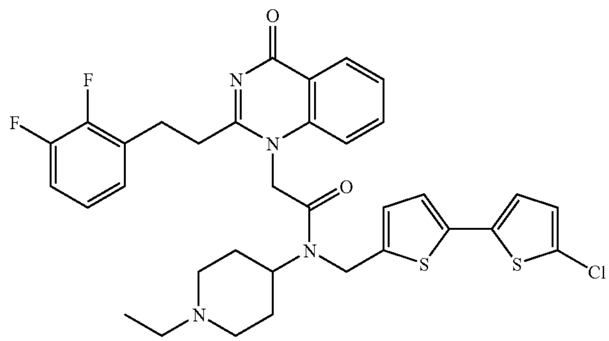 | N-(1-ethylpiperidin-4-yl)-2-(2-(2-(2,3-difluorophenyl)-ethyl)-4-oxo-4H-quinazolin-1-yl)-N-(2-(2-chlorothien-5-yl)thien-5-ylmethyl)-acetamide bitartrate |
| 135 | C43 + D82 | 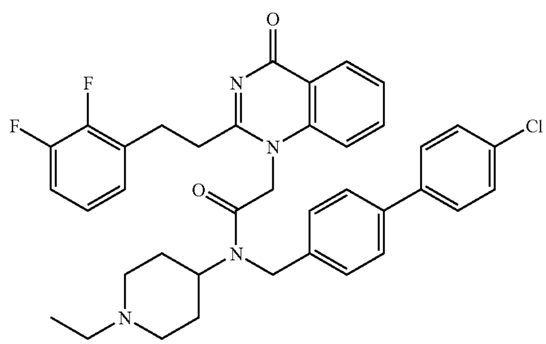 | N-(1-ethylpiperidin-4-yl)-2-(2-(2-(2,3-difluorophenyl)-ethyl)-4-oxo-4H-quninazolin-1-yl)-N-(4'-chloro-biphenyl-4-ylmethyl)acetamide bitartrate |
| 136 | C43 + D83 | 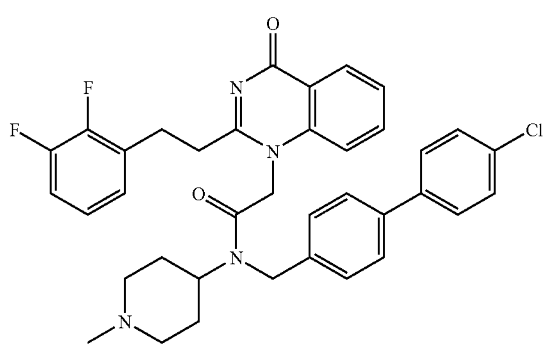 | N-(1-methylpiperidin-4-yl)-2-(2-(2-(2,3-difluorophenyl)-ethyl)-4-oxo-4H-quninazolin-1-yl)-N-(4'-chloro-biphenyl-4-ylmethyl)acetamide |
| 137 | C43 + D84 | 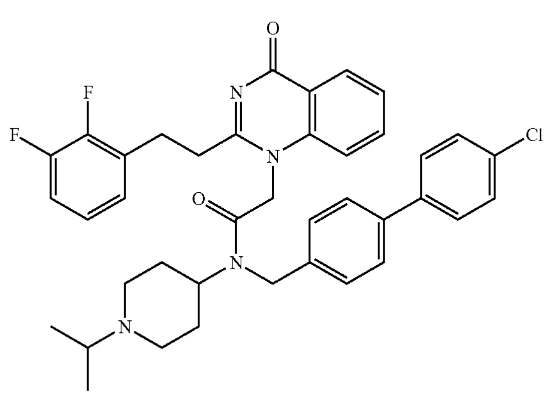 | N-(1-isopropylpiperidin-4-yl)-2-(2-(2-(2,3-difluorophenyl)-ethyl)-4-oxo-4H-quninazolin-1-yl)-N-(4'-chloro-biphenyl-4-ylmethyl)acetamide bitartrate |

| No. | Precursors | Structure | Name |
|---|---|---|---|
| 138 | C43 + D85 | 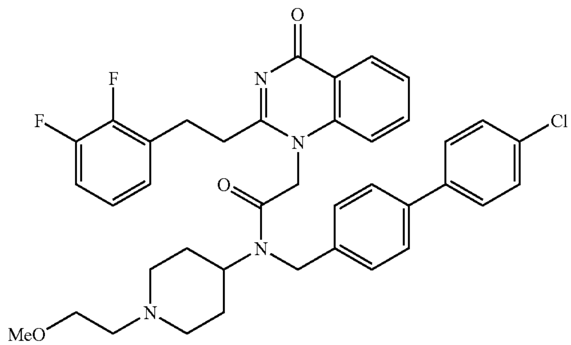 | N-(1-(2-methoxyethyl)piperidin-4-yl)-2-(2-(2-(2,3-difluorophenyl)-ethyl)-4-oxo-4H-quninazolin-1-yl)-N-(4'-chloro-biphenyl-4-ylmethyl)-acetamide bitartrate |
| 139 | C43 + D76 | 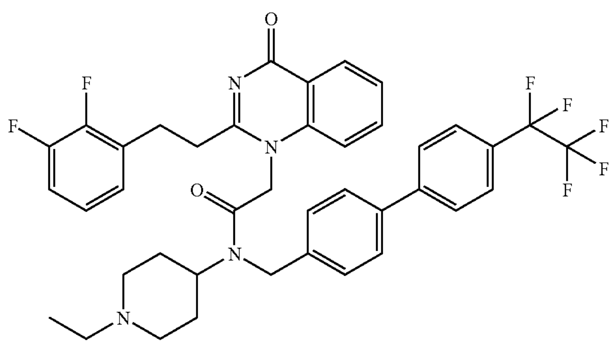 | N-(1-ethylpiperidin-4-yl)-2-(2-(2-(2,3-difluorophenyl)-ethyl)-4-oxo-4H-quninazolin-1-yl)-N-(4'-penta-fluoroethyl-biphenyl-4-ylmethyl)-acetamide bitartrate |
| 140 | C43 + D34 | 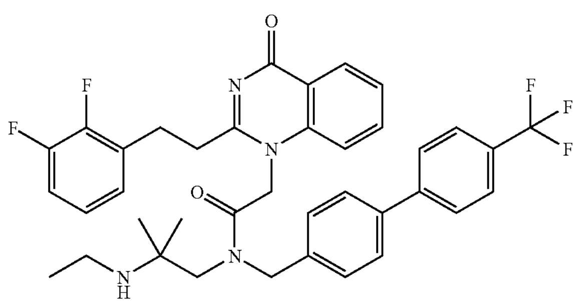 | N-(2-ethylamino-2-methylprop-1-yl)-2-(2-(2-(2,3-difluorophenyl)-ethyl)-4-oxo-4H-quinazolin-1-yl)-N-(4'-trifluoromethyl-biphenyl-4-ylmethyl)-acetamide |
| 141 | C43 + N-(2-hydroxyethyl)-4-(4-trifluoro-methylphenyl)-benzylamine (WO 00/66567) | 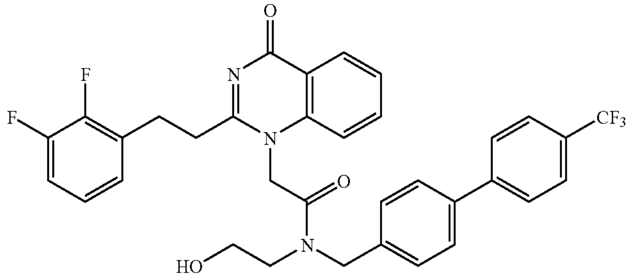 | N-(2-hydroxyethyl)-2-(2-(2-(2,3-difluorophenyl)-ethyl)-4-oxo-4H-quinazolin-1-yl)-N-(4'-trifluoromethyl-biphenyl-4-ylmethyl)acetamide |

-continued

| No. | Precursors | Structure | Name |
|-----|------------|-----------|------|
| 142 | C43 + D96 | 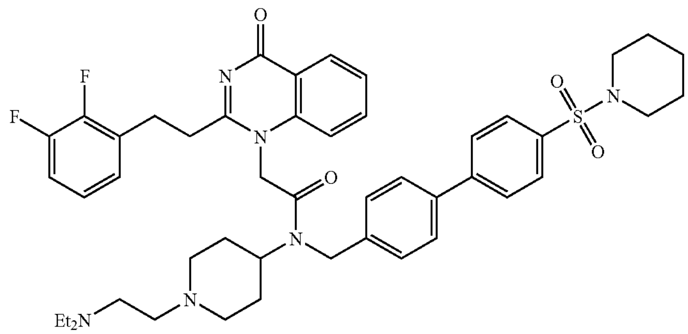 | N-(2-diethylaminoethyl)-2-(2-(2-(2,3-difluorophenyl)-ethyl)-4-oxo-4H-quinazolin-1-yl)-N-(4'-(piperidin-1-ylsulfonyl)-biphenyl-4-ylmethyl)-acetamide |
| 143 | C43 + D95 | 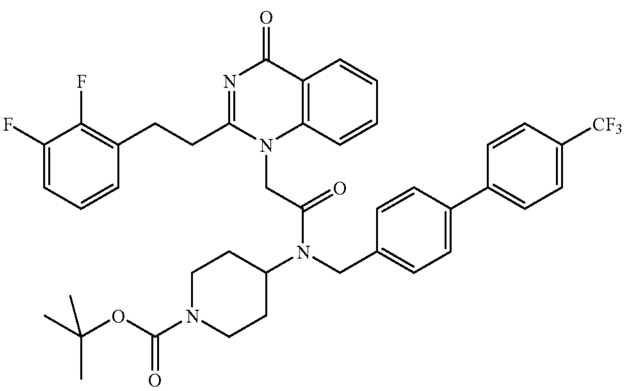 | N-(1-t-butoxycarbonylpiperidin-4-yl)-2-(2-(2-(2,3-difluorophenyl)-ethyl)-4-oxo-4H-quinazolin-1-yl)-N-(4'-trifluoromethyl-biphenyl-4-ylmethyl)acetamide |

The following compounds were prepared by the method of Intermediate C2

| No. | Precursors | Structure | Name |
|-----|------------|-----------|------|
| 144 | E127 | 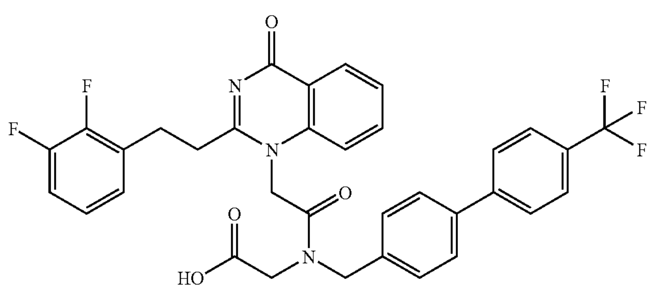 | N-(hydroxycarbonylmethyl)-2-(2-(2-(2,3-difluorophenyl)-ethyl)-4-oxo-4H-quinazolin-1-yl)-N-(4'-trifluoromethyl-biphenyl-4-ylmethyl)acetamide |
| 145 | E143 | 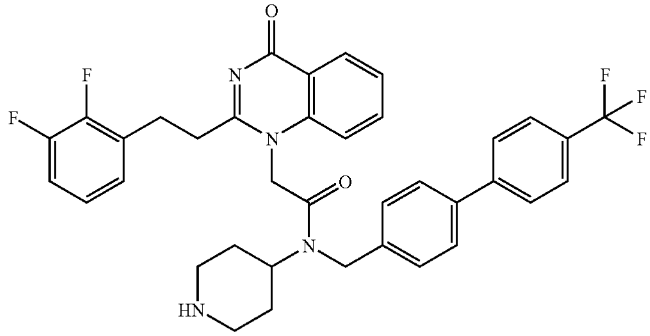 | N-(piperidin-4-yl)-2-(2-(2-(2,3-difluorophenyl)-ethyl)-4-oxo-4H-quinazolin-1-yl)-N-(4'-trifluoromethyl-biphenyl-4-ylmethyl)acetamide |

-continued

| No. | Precursors | Structure | Name |
|---|---|---|---|
| 146 | E82 | 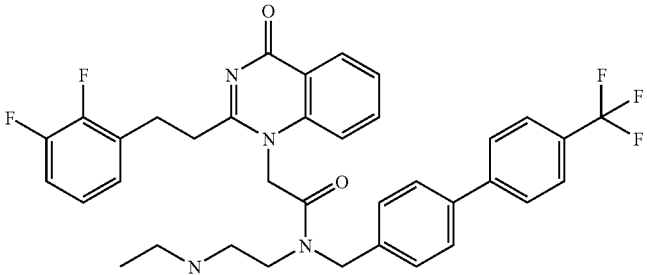 | N-(2-Ethylaminoethyl)-2-(2-(2-(2,3-difluorophenyl)-ethyl)-4-oxo-4H-quinazolin-1-yl)-N-(4'-trifluoromethyl-biphenyl-4-ylmethyl)acetamide bitartrate |

Biological Data

1. Screen for Lp-PLA$_2$ Inhibition.

Enzyme activity was determined by measuring the rate of turnover of the artificial substrate (A) at 37 C in 50 mM HEPES (N-2-hydroxyethylpiperazine-N'-2-ethanesulphonic acid) buffer containing 150 mM NaCl, pH 7.4.

(A)

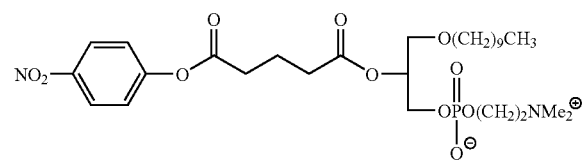

Assays were performed in 96 well titre plates.

Recombinant LpPLA2 was purified to homogeneity from baculovirus infected Sf9 cells, using a zinc chelating column, blue sepharose affinity chromatography and an anion exchange column. Following purification and ultra-filtration, the enzyme was stored at 6 mg/ml at 4° C. Assay plates of compound or vehicle plus buffer were set up using automated robotics to a volume of 170 μl. The reaction was initiated by the addition of 20 μl of 10× substrate (A) to give a final substrate concentration of 20 μM and 10 μl of diluted enzyme to a final 0.2 nM LpPLA2.

The reaction was followed at 405 nm and 37° C. for 20 minutes using a plate reader with automatic mixing. The rate of reaction was measured as the rate of change of absorbance.

Results

The compounds described in the Examples were tested as described above and had IC$_{50}$ values in the range <0.1 to 200 nM.

The invention claimed is:

1. A compound which is N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide

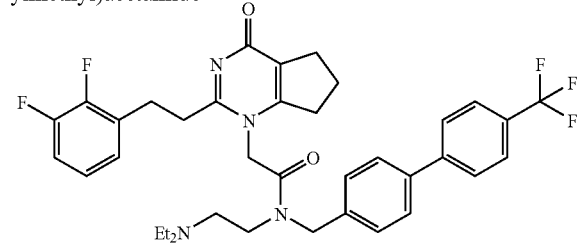

or a pharmaceutically acceptable salt thereof.

2. The compound of claim 1 in the form of its bitartrate salt.

3. A pharmaceutical composition comprising a compound according to claim 1, or a pharmaceutically acceptable salt thererof, and a pharmaceutically acceptable carrier.

4. A pharmaceutical composition according to claim 3 suitable for oral administration.

5. A pharmaceutical composition according to claim 4 which further comprises a therapeutically effective amount of a cholesterol lowering agent.

6. A pharmaceutical composition according to claim 5 wherein said cholesterol lowering agent is a statin.

7. A method of treating atherosclerosis comprising administrating a therapeutically effective amount of a compound according to claim 1 or a pharmaceutically acceptable salt thereof to a patient in need thereof, alone or in combination with a pharmaceutically acceptable carrier.

8. The method of claim 7 wherein the compound of claim 1 or a pharmaceutically acceptable salt thereof is administered with a cholesterol lowering agent.

9. The method of claim 8 wherein the cholesterol lowering agent is a statin.

10. A process for preparing a compound of claim 1 comprising: reacting a compound of formula (II):

(II)

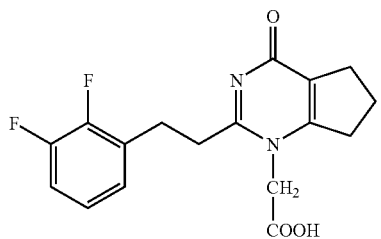

with a compound of formula (III):

(III)

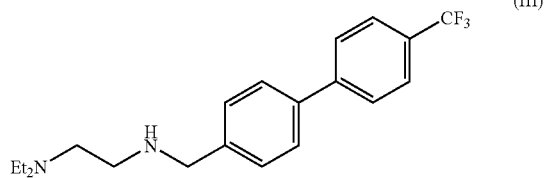

under amide forming conditions.

* * * * *